US007638128B2

(12) United States Patent
Dzau et al.

(10) Patent No.: US 7,638,128 B2

(45) Date of Patent: Dec. 29, 2009

(54) METHOD OF ENHANCING CARDIAC TISSUE REPAIR BY ADMINISTERING A SFRP POLYPEPTIDE

(75) Inventors: Victor Dzau, Durham, NC (US); Maria Mirotsou, Dresden (DE)

(73) Assignees: The Brigham and Women's Hospital, Inc., Boston, MA (US); Duke University, Durham, NC (US)

( * ) Notice: Subject to any disclaimer, the term of this patent is extended or adjusted under 35 U.S.C. 154(b) by 0 days.

(21) Appl. No.: 11/508,010

(22) Filed: Aug. 21, 2006

(65) Prior Publication Data

US 2007/0259425 A1 Nov. 8, 2007

Related U.S. Application Data

(60) Provisional application No. 60/710,028, filed on Aug. 19, 2005, provisional application No. 60/711,287, filed on Aug. 25, 2005.

(51) Int. Cl.
*C07K 14/435* (2006.01)
*A61K 38/17* (2006.01)

(52) U.S. Cl. ................. 424/185.1; 424/198.1; 530/350; 514/2; 514/12

(58) Field of Classification Search ....................... None
See application file for complete search history.

(56) References Cited

FOREIGN PATENT DOCUMENTS

| | | | |
|---|---|---|---|
| WO | WO 03/062376 | A2 | 7/2003 |
| WO | WO 2004/044142 | A2 | 5/2004 |
| WO | WO 2004/087874 | A2 | 10/2004 |

OTHER PUBLICATIONS

Skolnick et al. From genes to protein structure and function: novel applications of computational approaches in the genomic era. Trends in Biotech 18(1): 34-39, 2000.*

Bork, A. Powers and pitfalls in sequence analysis: the 70% hurdle. Genome Res 10: 398-400, 2000.*

Doerks et al. Protein annotation: detective work for function prediction. Trends in Genetics 14(6): 248-250, 1998.*

Smith et al. The challenges of genome sequence annotation or "The devil is in the details". Nature Biotech 15: 1222-1223, 1997.*

Brenner, S.E. Errors in genome function. Trends in Genetics 15(4): 132-133, 1999.*

Bork et al. Go hunting in sequence databases but watch out for the traps. Trends in Genetics. 12(10): 425-427, 1996.*

Wells. J.A. Additivity of mutational effects in proteins. Biochemistry 29 (37): 8509-8517, 1990.*

Ngo et al. Computational complexity, protein structure prediction, and the Levinthal paradox. The Protein Folding Problem and Tertiary Structure Prediction, pp. 492-495, 1994.*

Barandon et al. Frizzled A, a novel angiogenic factor: promises for cardiac repair. Eur J Cardiothoracic Surg 25(1): 76-83, 2004.*

Dufourq et al. FrzA, a secreted Frizzled related protein, induced angiogenic response. Circulation 106(24): 3097-3103, 2002.*

Mirotsou et al. Secreted frizzled related protein 2 (Sfrp2) is the key Akt-mesenchymal stem cell-released paracrine factor mediating myocardial survival and repair. Proc Natl Acad Sci USA 104(5): 1643-1648, 2007.*

Alvarez-Dolado et al. *Nature*, 425:968-973 (2003).

Barandon et al. *Circulation*, 108:2282-2289 (2003).

Beltrami et al. *Cell*, 114:763-776 (2003).

Bergmann et al. *J. Mol. Cell. Cardiol.*, 37:681-690 (2004).

Caplice et al. *Nat. Clin. Pract. Cardiovasc. Med.*, 1(2):90-95 (2004).

Dimmeler et al. *J. Clin. Invest.*, 115(3):572-583 (2005).

Fazel et al. *J. Clin. Invest.*, 116(7):1865-1877 (2006).

Gnecchi et al. *Nat. Med.*, 11(4):367-368 (2005).

Guo et al. *Circulation*, Abstract only, 114(18):515, Supplement II (Oct. 31, 2006).

Jones et al. *BioEssays*, 24:811-820 (2002).

Kawano et al. *J. Cell Sci.*, 116(13):2627-2634 (2003).

Kinnaird et al. *Circ. Res.*, 95:354-363 (2004).

Lee et al. *J. Biol. Chem.*, 279(15):14602-14609 (2004).

Li et al. *Genome Biol.*, 2(8):0032.1-0032.11 (2001).

Logan et al. *Annu. Rev. Cell Dev. Biol.*, 20 :781-810 (2004).

Mangi et al. *Nat. Med.*, 9(9):1195-1201 (2003).

Manji et al. *J. Clin. Psychiatry*, 61(Suppl. 9):82-96 (2000).

Melo et al. *Circulation*, 109:2386-2393 (2004).

Mercer et al. *EMBO J.*, 19(14):3597-3607 (2000).

Mirotsou et al. *Circulation*, Abstract only, 112(17):660, Supplement (Nov. 17, 2005).

Moon et al. *Science*, 296:1644-1646 (2002).

Nakamura et al. *Proc. Natl. Acad. Sci. USA*, 100(10):5834-5839 (2003).

Pandur et al. *Nature*, 418:636-641 (2002).

Schneider et al. *Genes Dev.*, 15:304-315 (2001).

Schumann et al. *Cardiovasc. Res.*, 45:720-728 (2000).

Uren et al. *J. Biol. Chem.*, 275(6):4374-4382 (2000).

Van Gijn et al. *Cardiovasc. Res.*, 55:16-24 (2002).

Wang et al. *Cancer Res.*, 65(19):8604-8607 (2005).

Xu et al. *Nat. Med.*, 3(9):997-1004 (1997).

GenBank Accession No. BC036503, Oct. 2003.

Han et al., "Secreted Frizzled-related Protein 1 (SFRP1) Protects Fibroblasts from Ceraminde-induced Apoptosis", *J. Biol. Chem.*, 279(4):2832-2840 (2004).

Database EBI, "Protein Factor Discovery Related Isolated Human Polypeptide", Tang et al., XP-002494344, Abstract only, Dec. 30, 2004.

* cited by examiner

*Primary Examiner*—Bridget E Bunner
(74) *Attorney, Agent, or Firm*—Mintz, Levin, Cohn, Ferris, Glovsky and Popeo, P.C.; Ingrid A. Beattie

(57) ABSTRACT

A purified paracrine factor of a mesenchymal stem cell, such as a Secreted frizzled related protein (Sfrp) is useful to reduce cell death an/or tissue injury associated with ischemic conditions.

4 Claims, 11 Drawing Sheets a Genes up-regulated by Sfrp2 under hypoxia (Superarray)
Fold changes
0
2
4
6
8
10
12
Bcl2a1
Bcl2
Bcl2l1
Foxa2
Birc3
Birc1b
b The effect of Sfrp2 on mRNA levels of Birc1b (RT-PCR)
Nor
Hypoxia
0 0 0 0.3 3 30 300 3000 pM
0 0 0 0.01 0.1 1 10 100 ng/ml
Birc1b
Birc3
C Beta-catenin levels upregulated by Sfrp2
Nor
Hypoxia
0 0 0.3 3 30 300 3000 pM
0 0 0.01 0.1 1 10 100 ng/ml
Nuclear beta-catenin
Total beta-catenin
GAPDH

His-h12 protein phosphorylates/activates Akt$^{Thr308}$ in cardiomyocytes at 30 min

Phosphorylation of GSK-3ß in cardiomyocytes at 30 min

Total Akt expression in cardiomyocytes

Expression of ß–tublin in cardiomyocytes as loading control

Inhibiton of cytochrome C release into cytosolic compartment by His-h12 protein during cardiomyocyte apoptosis

Stablizition of Mitochondrial Bcl-2 protein level by His-h12 protein during cardiomyocyte apoptosis

METHOD OF ENHANCING CARDIAC TISSUE REPAIR BY ADMINISTERING A SFRP POLYPEPTIDE

RELATED APPLICATIONS

This application claims priority to provisional patent application Ser. No. 60/710,028, filed on Aug. 19, 2005 and provisional patent application Ser. No. 60/711,287, filed on Aug. 25, 2005, the entire contents of each being hereby incorporated by reference.

STATEMENT AS TO FEDERALLY SPONSORED RESEARCH

This invention was made with U.S. government support under National Institutes of Health grant number HL073219. The government has certain rights in the invention.

FIELD OF THE INVENTION

The invention relates to cardiac disorders.

BACKGROUND OF THE INVENTION

Patient mortality and morbidity is increased by cell/tissue damage or death resulting from acute and chronic injury or disease of the heart muscle, such as myocardial infarction, cardiac failure, stroke, degenerative neurological disease, spinal injury, musculoskeletal diseases, hypertension, and diabetes.

SUMMARY OF THE INVENTION

The invention is based upon the surprising discovery that paracrine factors secreted from mesenchymal stem cells (MSC) confer a therapeutic benefit to bodily tissues. Thus, stem cells serve as a factory of biologic products that are purified and administered to subjects.

The paracrine factors are useful in cellular and tissue protection, repair, and regeneration. Mesenchymal stem cells or progenitor cells that secrete cytoprotective paracrine factors preferably comprise an Akt gene (Akt-MSC). One or more secreted compounds (e.g., and isolated compound or a mixture of secreted compounds such as a MSC culture supernatant) confers a clinical benefit to a variety of injured, compromised, or disease tissues.

A method of reducing cell death or enhancing tissue repair is carried out by contacting an injured or diseased tissue with a composition comprising a paracrine factor of a mesenchymal stem cell (MSC). The composition is administered to healthy tissue that is determined to be at high risk of injury or to injured tissue following the occurrence of an injury. Preferably, the factor is a Secreted frizzled related protein (Sfrp). Optionally, the composition contains one or more paracrine factors, e.g., two, three, five, ten or more factors. The factors provide cell reparative benefits in a synergistic manner. For example, the composition contains one or more Sfrp, e.g., Sfrp-1, Sfrp-2, and Sfrp-3. In one embodiment, Sfrp-1 comprises an amino acid sequence of SEQ ID NO:5, a mature processed form of SEQ ID NO:5, or a fragment thereof, in another embodiment, Sfrp-2 comprises an amino acid sequence of SEQ ID NO:7, a mature processed form of SEQ ID NO:7, or a fragment thereof; and in yet another embodiment, Sfrp-3 comprises an amino acid sequence of SEQ ID NO:9, a mature processed form of SEQ ID NO:9, or a fragment thereof. The amount of apoptotic cell death is reduced in the presence of a paracrine factor such as an Sfrp compared to in its absence.

Cytoprotective and cell reparative effects are conferred to many types of bodily tissues such as cardiac tissue. For example, in the case of a myocardial infarction, cardiac infarct size is reduced following contact of myocardial tissue with the paracrine factor.

Factors derived from Akt-MSCs, which have been genetically altered to contain a recombinant Akt gene sequence, confer a therapeutic benefit at each stage of a hypoxic cardiac event (early, middle, and late stage). Early on, factors confer a cell protective effect, followed by inotropy, angiogenesis, and cardiac remodeling.

The invention also features methods of inhibiting cell damage, inducing or enhancing cell repair or regeneration or inhibiting an ischemic or reperfusion related injury in a subject. Cell damage or injury is inhibited by administering to the subject or contacting a cell with a composition containing a purified cytoprotective compound such as a substantially pure polypeptide, or a mixture of substantially pure polypeptides such as the Sfrp proteins described above. Other purified proteins, e.g., h1, h5, h8, h12, and h13 are also useful to prevent or reduce cell damage. Accordingly, a method of reducing cell death is carried out by contacting an injured or diseased tissue with a composition comprising a purified paracrine factor of a mesenchymal stem cell selected from the group consisting of h1, h5, h8, h12 and h13 or fragment thereof. For example, h12 comprises a fragment of SEQ ID NO:17.

Similarly, cell repair or regeneration is induced by administering to the subject or contacting a cell with a composition containing a purified cytoprotective compound. Polypeptides or other compounds described herein are said to be "substantially pure" when they are within preparations that are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylaminde gel electrophoresis, or HPLC analysis. The polypeptide is purified from MSC culture media or recombinantly produced.

Cell or tissue damage is defined by a loss or diminution of cell function. Such loss or decrease in function leads to eventual cell death. The cell is a cardiac cell such as a cardiomyocyte, a kidney cell, a liver cell, a neurological (e.g., brain, spinal cord) cell, or a pancreatic cell. For example, a loss of cardiomyocyte function results in the loss of the contractile function of the cell. Cardiomyocytes that have lost their ability to contract form round cells rather that rod shaped cells when cultured. Ischemia causes irreversible cellular/tissue damage and cell death. Reperfusion exacerbates ischemic damage by activating inflammatory response and oxidative stress. Oxidative stress modifies membrane lipids, proteins and nucleic acids resulting in cellular/tissue damage or death, and depression of cardiac, endothelial and kidney function.

Also included in the invention are methods of regenerating an injured myocardial tissue by administered to the tissue a composition containing a cytoprotective compound. The cardiac muscle has been damaged by disease, such as a myocardial infarction. By regenerating an injured myocardial tissue is meant restoring ventricular function and/or decreasing infarct size. Ventricular function is measured by methods known in the art such as radionuclide angiography.

A cytoprotective compound is a compound, which is capable of inhibiting cell damage such as oxidative-stress induced cell death or apoptosis. In addition to Sfrps, cytoprotective compounds include for example adipsin, adrenomedullin, chemokine (C-C motif) ligand 2, cysteine rich protein 61, lysyl oxidase-like 2, or serine proteinase inhibitor.

The composition is administered to the subject prior to, at the time of, or shortly after (1, 5, 10, 15, 30, 60 minutes; 1.5, 2, 4, 6, 12, 18, 24, 48 hours) identification of cell damage or identification of a symptom of ischemia or reperfusion injury. For example the composition is administered to a subject prior to a cardiac event or ischemic-reperfusion injury. Such a subject is a risk candidate for an ischemic event or condition. Symptoms of a cardiac event include for example, chest pain, arm pain, fatigue and shortness of breath. For example, the composition is administered at the onset of symptoms, e.g., chest pain, associated with a cardiac event such as a myocardial infarction. The composition is administered systemically or locally. For example, the composition is administered directly, i.e., by myocardial injection to the cardiac tissue, or systemically, e.g., interperitoneally, orally, intravenously. In another example, administration of the composition is carried out by infusion into a coronary artery. Slow-release formulations, e.g., a dermal patch, in which diffusion of the composition from an excipient such as a polymeric carrier mediates drug delivery are also within the invention. Optionally, the subject is further administered VEGF or thyrosin beta 4.

The composition is administered at a dose sufficient to inhibit apoptotic death or oxidative stress-induced cell death. To determine whether the composition inhibits oxidative-stress induced cell death, the composition is tested by incubating the composition with a primary or immortalized cell such as a cardiomyocyte. A state of oxidative stress of the cells is induced (e.g., by incubating cells with $H_2O_2$), and cell viability is measured using standard methods. As a control, the cells are incubated in the absence of the composition and then a state of oxidative stress is induced. A decrease in cell death (or an increase in the number of viable cells) in the compound treated sample indicates that the composition inhibits oxidative-stress induced cell death. Alternatively, an increase in cell death (or an decrease in the number of viable cells) in the compound treated sample indicates that the composition does not inhibit oxidative-stress induced cell death. The test is repeated using different doses of the composition to determine the dose range in which the composition functions to inhibit oxidative-stress induced cell death.

A subject to be treated is suffering from or at risk of developing a condition characterized by aberrant cell damage such as oxidative-stress induced cell death (e.g., apoptotic cell death) or an ischemic or reperfusion related injury. A subject suffering from or at risk of developing such a condition is identified by the detection of a known risk factor, e.g., gender, age, high blood pressure, obesity, diabetes, prior history of smoking, stress, genetic or familial predisposition, attributed to the particular disorder, or previous cardiac event such as myocardial infarction or stroke.

Conditions characterized by aberrant cell damage or death include cardiac disorders (acute or chronic) such as stroke, myocardial infarction, chronic coronary ischemia, arteriosclerosis, congestive heart failure, dilated cardiomyopathy, restenosis, coronary artery disease, heart failure, arrhythmia, angina, atherosclerosis, hypertension, renal failure, kidney ischemia, ischemic hepatitis, hepatic vein thrombosis, cirrhosis, portal vein thrombosis, pancreatitis, ischemic colitis, or myocardial hypertrophy. Cardiac repair or regeneration is evaluated by detecting an improvement of symptoms such as chest pain or shortness of breath as well as by evaluation of heart function by standard methods such as cardiac magnetic resonance, echocardiography, and/or ventricular angiography.

Also within the invention is a cell culture or preservation media containing purified Sfrp2 and a method of maintaining inhibiting stem cell differentiation, e.g., inhibiting myogenesis, by contacting a population of isolated stem cells with purified Sfrp2. Isolated stem cells are selected from the group consisting of embryonic stem cells, mesenchymal stem cells, and hematopoetic stem cells. Stem cells are isolated from the tissue of origin by fractionation by cell surface markers or other distinguishing characteristics. Preferably, a population of isolated cells is at least 85% stem cells. More preferably, the population is 90, 95, 98, 99, 100% stem cells.

This factor is involved in the maintenance and self renewal of tissue specific and embryonic stem cells. For example, differentiation of stem cells, e.g., embryonic stem cells, is inhibited by Sfrp2. Myogenesis is inhibited by contacting stem cells with Sfrp2. In another example, bone marrow-derived hematopoetic stem are maintained in a stem cell state by contacting the cells with purified Sfrp2. Preservation of stem cells in this manner is useful in transport and storage of stem cells prior to transplantation into a subject for therapeutic purposes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1A shows levels of Sfrp1, Sfrp2 and Sfrp3 expression as estimated by microarray analysis and shows a nearly 10 fold upregulation of Sfrp2 in Akt-MSC compared to GFP-MSC. FIG. 1B shows a quantitative real-time RT-PCR validation of mRNA expression levels that demonstrates a 100 fold upregulation of Sfrp2 gene expression in Akt-MSC compared to GFP-MSC.

FIG. 5A is a photograph of an electrophoretic gel showing that Wnt3a mRNA expression as detected by RT-PCR is increased in hypoxic cardiomyocytes while expression of Wnt5 remains unchanged. The data indicate that hypoxic cardiomyocytes upregulate Wnt3a expression and that Sfrp2 blocks pro-apototic effects of Wnt3a.

FIG. 5B is a bar graph showing that Wnt3a (3 nM) increases caspase activity of cardiomyocytes undergoing hypoxia/reoxygenation injury; Sfrp2 at a similar concentration significantly attenuates Wnt3a induced caspase activity (*vs. normoxia, $p<0.05$; **vs. wnt+hypoxia/reoxygenation, $p<0.05$, n=6/group).

DETAILED DESCRIPTION

Figure 1:
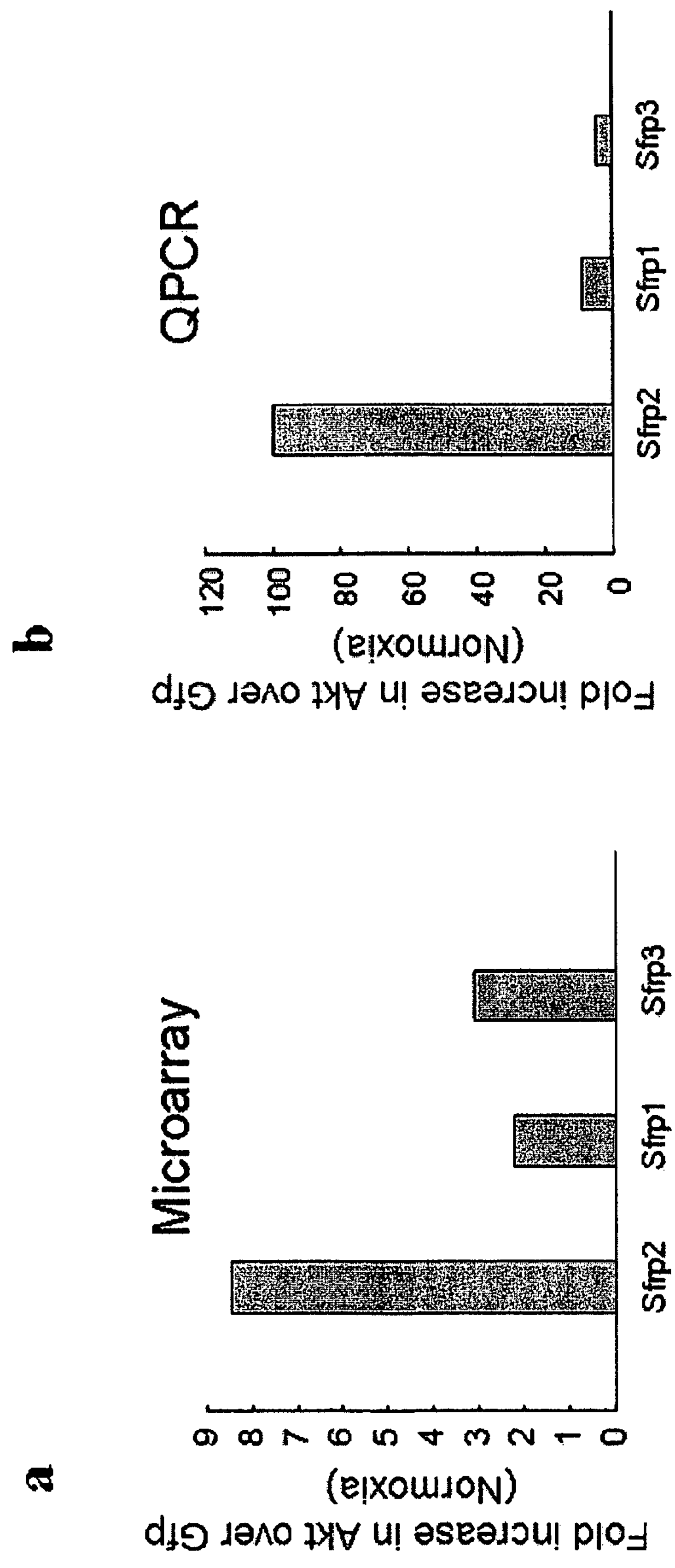
FIGS. 1A and 1B are bar graphs showing that Sfrps are expressed in mesenchymal stem cells.

The present invention is based upon the unexpected discovery of that MSC-secreted products confer a therapeutic benefit to injured or compromised tissues. Disclosed herein is a Akt-MSC mediated paracrine mechanism of organ protection and repair. More particularly, the invention provides purified polypeptides such as Srfps isolated from Akt-MSCs or recombinantly or synthetically produced and methods of using these polypeptides to prevent or reduce myocardial damage and ventricular dysfunction.

Akt Genes

Akt-MSCs are produced by introducing (e.g., by retrovirus-mediated transduction) into mesenchymal stem cells isolated from the bone marrow an Akt coding sequence or fragment, e.g., Akt-1, Ak-2 or Akt-3. The Akt nucleic acid is human, mouse, or rat.

Exemplary human Akt-1 polypeptides include GenBank Accession numbers NP_005154 and AAH00479. Exemplary human Akt-2 polypeptides includes for example GenBank Accession numbers P31751 and NP_001617. Exemplary human Akt-3 polypeptides includes for example GenBank Accession numbers Q9Y243 and NP_005456. Exemplary nucleic acids encoding Akt include human Akt-1 available at GENBANK™ Accession No. NM_005163 (SEQ ID NO:1), human Akt-2 available at GENBANK™ Accession No. NM_001626 (SEQ ID NO:2) and human Akt-3 available at GENBANK™ Accession No. AJ245709 (SEQ ID NO:3) (all of which are hereby incorporated by reference) or nucleic acids encoding the human Akt polypeptides described above. mRNA sequences and the corresponding coding region for human Akt are shown below.

| Akt-1 mRNA (SEQ ID NO: 1) |
|---|
| 1 atcctgggac agggcacagg gccatctgtc accaggggct tagggaaggc cgagccagcc |
| 61 tgggtcaaag aagtcaaagg ggctgcctgg aggaggcagc ctgtcagctg gtgcatcaga |
| 121 ggctgtggcc aggccagctg ggctcgggga gcgccagcct gagaggagcg cgtgagcgtc |
| 181 gcgggagcct cgggcaccat gagcgacgtg gctattgtga aggagggttg gctgcacaaa |
| 241 cgaggggagt acatcaagac ctggcggcca cgctacttcc tcctcaagaa tgatggcacc |
| 301 ttcattggct acaaggagcg gccgcaggat gtggaccaac gtgaggctcc cctcaacaac |
| 361 ttctctgtgg cgcagtgcca gctgatgaag acggagcggc cccggcccaa caccttcatc |
| 421 atccgctgcc tgcagtggac cactgtcatc gaacgcacct tccatgtgga gactcctgag |
| 481 gagcgggagg agtggacaac cgccatccag actgtggctg acggcctcaa gaagcaggag |

-continued

| Akt-1 mRNA (SEQ ID NO: 1) |
| --- |
| 541 gaggaggaga tggacttccg gtcgggctca cccagtgaca actcaggggc tgaagagatg |
| 601 gaggtgtccc tggccaagcc caagcaccgc gtgaccatga acgagtttga gtacctgaag |
| 661 ctgctgggca agggcacttt cggcaaggtg atcctggtga aggagaaggc cacaggccgc |
| 721 tactacgcca tgaagatcct caagaaggaa gtcatcgtgg ccaaggacga ggtggcccac |
| 781 acactcaccg agaaccgcgt cctgcagaac tccaggcacc ccttcctcac agccctgaag |
| 841 tactctttcc agacccacga ccgcctctgc tttgtcatgg agtacgccaa cgggggcgag |
| 901 ctgttcttcc acctgtcccg ggaacgtgtg ttctccgagg accgggcccg cttctatggc |
| 961 gctgagattg tgtcagccct ggactacctg cactcggaga agaacgtggt gtaccgggac |
| 1021 ctcaagctgg agaacctcat gctggacaag gacgggcaca ttaagatcac agacttcggg |
| 1081 ctgtgcaagg aggggatcaa ggacggtgcc accatgaaga ccttttgcgg cacacctgag |
| 1141 tacctggccc ccgaggtgct ggaggacaat gactacggcc gtgcagtgga ctggtggggg |
| 1201 ctgggcgtgg tcatgtacga gatgatgtgc ggtcgcctgc ccttctacaa ccaggaccat |
| 1261 gagaagcttt ttgagctcat cctcatggag gagatccgct tcccgcgcac gcttggtccc |
| 1321 gaggccaagt ccttgctttc agggctgctc aagaaggacc ccaagcagag gcttggcggg |
| 1381 ggctccgagg acgccaagga gatcatgcag catcgcttct ttgccggtat cgtgtggcag |
| 1441 cacgtgtacg agaagaagct cagcccaccc ttcaagcccc aggtcacgtc ggagactgac |
| 1501 accaggtatt ttgatgagga gttcacggcc cagatgatca ccatcacacc acctgaccaa |
| 1561 gatgacagca tggagtgtgt ggacagcgag cgcaggcccc acttccccca gttctcctac |
| 1621 tcggccagca gcacggcctg aggcggcggt ggactgcgct ggacgatagc ttggagggat |
| 1681 ggagaggcgg cctcgtgcca tgatctgtat ttaatggttt ttatttctcg ggtgcatttg |
| 1741 agagaagcca cgctgtcctc tcgagcccag atggaaagac gtttttgtgc tgtgggcagc |
| 1801 accctccccc gcagcggggt agggaagaaa actatcctgc gggttttaat ttatttcatc |
| 1861 cagtttgttc tccgggtgtg gcctcagccc tcagaacaat ccgattcacg tagggaaatg |
| 1921 ttaaggactt ctacagctat gcgcaatgtg gcattggggg gccgggcagg tcctgcccat |
| 1981 gtgtcccctc actctgtcag ccagccgccc tgggctgtct gtcaccagct atctgtcatc |
| 2041 tctctggggc cctgggcctc agttcaacct ggtggcacca gatgcaacct cactatggta |
| 2101 tgctggccag caccctctcc tgggggtggc aggcacacag cagcccccca gcactaaggc |
| 2161 cgtgtctctg aggacgtcat cggaggctgg gcccctggga tgggaccagg gatgggggat |
| 2221 gggccagggt ttacccagtg ggacagagga gcaaggttta aatttgttat tgtgtattat |
| 2281 gttgttcaaa tgcattttgg gggtttttaa tctttgtgac aggaaagccc tccccccttcc |
| 2341 ccttctgtgt cacagttctt ggtgactgtc ccaccggagc ctccccctca gatgatctct |
| 2401 ccacggtagc acttgacctt ttcgacgctt aacctttccg ctgtcgcccc aggccctccc |
| 2461 tgactccctg tgggggtggc catccctggg cccctccacg cctcctggcc agacgctgcc |
| 2521 gctgccgctg caccacggcg ttttttttaca acattcaact ttagtatttt tactattata |
| 2581 atataatatg gaaccttccc tccaaattct |
| Coding sequence = nucleotide 199-1641. |

| Akt-2 mRNA (SEQ ID NO: 2) |
|---|
| 1 gaattccagc ggcggcgccg ttgccgctgc cgggaaacac aaggaaaggg aaccagcgca |
| 61 gcgtggcgat gggcgggggt agagccccgc cggagaggct gggcggctgc cggtgacaga |
| 121 ctgtgccctg tccacggtgc ctcctgcatg tcctgctgcc ctgagctgtc ccgagctagg |
| 181 tgacagcgta ccacgctgcc accatgaatg aggtgtctgt catcaaagaa ggctggctcc |
| 241 acaagcgtgg tgaatacatc aagacctgga ggccacggta cttcctgctg aagagcgacg |
| 301 gctccttcat tgggtacaag gagaggcccg aggcccctga tcagactcta ccccccttaa |
| 361 acaacttctc cgtagcagaa tgccagctga tgaagaccga gaggccgcga cccaacacct |
| 421 ttgtcatacg ctgcctgcag tggaccacag tcatcgagag gaccttccac gtggattctc |
| 481 cagacgagag ggaggagtgg atgcgggcca tccagatggt cgccaacagc ctcaagcagc |
| 541 gggccccagg cgaggacccc atggactaca agtgtggctc ccccagtgac tcctccacga |
| 601 ctgaggagat ggaagtggcg gtcagcaagg cacgggctaa agtgaccatg aatgacttcg |
| 661 actatctcaa actccttggc aagggaacct ttggcaaagt catcctggtg cgggagaagg |
| 721 ccactggccg ctactacgcc atgaagatcc tgcgaaagga agtcatcatt gccaaggatg |
| 781 aagtcgctca cacagtcacc gagagccggg tcctccagaa caccaggcac ccgttcctca |
| 841 ctgcgctgaa gtatgccttc cagacccacg accgcctgtg ctttgtgatg gagtatgcca |
| 901 acgggggtga gctgttcttc cacctgtccc gggagcgtgt cttcacagag gagcgggccc |
| 961 ggttttatgg tgcagagatt gtctcggctc ttgagtactt gcactcgcgg gacgtggtat |
| 1021 accgcgacat caagctggaa aacctcatgc tggacaaaga tggccacatc aagatcactg |
| 1081 actttggcct ctgcaaagag ggcatcagtg acggggccac catgaaaacc ttctgtggga |
| 1141 ccccggagta cctggcgcct gaggtgctgg aggacaatga ctatggccgg gccgtggact |
| 1201 ggtgggggct gggtgtggtc atgtacgaga tgatgtgcgg ccgcctgccc ttctacaacc |
| 1261 aggaccacga gcgcctcttc gagctcatcc tcatggaaga gatccgcttc ccgcgcacgc |
| 1321 tcagccccga ggccaagtcc ctgcttgctg ggctgcttaa gaaggacccc aagcagaggc |
| 1381 ttggtggggg gcccagcgat gccaaggagg tcatggagca caggttcttc ctcagcatca |
| 1441 actggcagga cgtggtccag aagaagctcc tgccaccctt caaacctcag gtcacgtccg |
| 1501 aggtcgacac aaggtacttc gatgatgaat ttaccgccca gtccatcaca atcacacccc |
| 1561 ctgaccgcta tgacagcctg ggcttactgg agctggacca gcggacccac ttcccccagt |
| 1621 tctcctactc ggccagcatc cgcgagtgag cagtctgccc acgcagagga cgcacgctcg |
| 1681 ctgccatcac cgctgggtgg ttttttaccc ctgcc |
| Coding sequence = nucleotide 204-1649. |

| Akt-3 mRNA (SEQ ID NO: 3) |
|---|
| 1 gggagtcatc atgagcgatg ttaccattgt gaaagaaggt tgggttcaga agaggggaga |
| 61 atatataaaa aactggaggc caagatactt ccttttgaag acagatggct cattcatagg |
| 121 atataaagag aaacctcaag atgtggattt accttatccc ctcaacaact tttcagtggc |
| 181 aaaatgccag ttaatgaaaa cagaacgacc aaagccaaac acatttataa tcagatgtct |
| 241 ccagtggact actgttatag agagaacatt tcatgtagat actccagagg aaagggaaga |

-continued

| Akt-3 mRNA (SEQ ID NO: 3) |
|---|
| 301 atggacagaa gctatccagg ctgtagcaga cagactgcag aggcaagaag aggagagaat |
| 361 gaattgtagt ccaacttcac aaattgataa tataggagag gaagagatgg atgcctctac |
| 421 aacccatcat aaaagaaaga caatgaatga ttttgactat ttgaaactac taggtaaagg |
| 481 cacttttggg aaagttattt tggttcgaga gaaggcaagt ggaaaatact atgctatgaa |
| 541 gattctgaag aaagaagtca ttattgcaaa ggatgaagtg gcacacactc taactgaaag |
| 601 cagagtatta aagaacacta gacatccctt tttaacatcc ttgaaatatt ccttccagac |
| 661 aaaagaccgt ttgtgttttg tgatggaata tgttaatggg ggcgagctgt ttttccattt |
| 721 gtcgagagag cgggtgttct ctgaggaccg cacacgtttc tatggtgcag aaattgtctc |
| 781 tgccttggac tatctacatt ccggaaagat tgtgtaccgt gatctcaagt tggagaatct |
| 841 aatgctggac aaagatggcc acataaaaat tacagatttt ggactttgca aagaagggat |
| 901 cacagatgca gccaccatga agacattctg tggcactcca gaatatctgg caccagaggt |
| 961 gttagaagat aatgactatg gccgagcagt agactggtgg ggcctagggg ttgtcatgta |
| 1021 tgaaatgatg tgtgggaggt tacctttcta caaccaggac catgagaaac tttttgaatt |
| 1081 aatattaatg gaagacatta aatttcctcg aacactctct tcagatgcaa aatcattgct |
| 1141 ttcagggctc ttgataaagg atccaaataa acgccttggt ggaggaccag atgatgcaaa |
| 1201 agaaattatg agacacagtt tcttctctgg agtaaactgg caagatgtat atgataaaaa |
| 1261 gcttgtacct ccttttaaac ctcaagtaac atctgagaca gatactagat attttgatga |
| 1321 agaatttaca gctcagacta ttacaataac accacctgaa aaatatgatg aggatggtat |
| 1381 ggactgcatg gacaatgaga ggcggccgca tttccctcaa ttttcctact ctgcaagtgg |
| 1441 acgagaataa gtctctttca ttctgctact tcactgtcat cttcaattta ttactgaaaa |
| 1501 tgattcctgg acatcaccag tcctagctct tacacatagc aggggca |
| Coding sequence = nucleotide 11-1450 |

Intramyocardial transplantation of adult stem cells has been proposed as a therapy to repair and regenerate damaged myocardium and to restore cardiac function after acute myocardial infarction (MI). Given their multipotency, low immunogenicity, amenability to ex vivo expansion and genetic modification, autologous bone marrow derived MSCs are suitable for this purpose. Injection of MSCs reduces post-infarction ventricular remodeling and in some cases improves left ventricular function. However prior to the invention, mechanism(s) underlying these therapeutic effects have not been clearly defined. In situ differentiation of the transplanted MSCs into cardiomyocytes and other constituent cardiac cell types has been suggested. Intramyocardial transplantation of MSCs transduced with a retroviral vector overexpressing the survival gene Akt markedly improves the therapeutic efficacy of MSCs in preventing ventricular remodeling and restoring cardiac function.

The data described herein shows that therapeutic effects seen with the administration of cells occur in less than 72 hours after infarction. These early dramatic effects cannot be readily attributed to myocardial regeneration or neoangiogenesis, but rather indicate that Akt-MSCs release biologically active factors that exert paracrine actions on the ischemic cardiomyocytes. Under hypoxic stimulation, genetically-modified bone marrow derived MSCs overexpressing the Akt gene release paracrine factors that exert cytoprotective effects on isolated cardiomyocytes. Intramyocardial injection of these substances reduces infarct size, prevents left ventricular dysfunction, and decreases in the number of apoptotic cardiomyocytes in vivo. In addition, no increase in microvessel density was observed in is the treated groups compared to controls 72 hours after the injection of the conditioned medium Thus, a significant portion of the salutary effects of Akt-MSCs transplantation is attributable to protection and functional recovery of ischemic myocardium, instead of, or in addition to, de novo cardiac repair and regeneration. The ability of bone marrow derived MSCs, especially Akt-MSCs, to produce factor(s) capable of protecting cardiomyocytes from cell death has not been previously demonstrated.

Secreted Frizzled-Related Proteins

The GENBANK™ Accession numbers of human Sfrps include BCO36503 (Sfrp1), BC008666 (Sfrp2), and NM001463 (Sfrp3), hereby incorporated by reference. The amino acid sequence of exemplary Sfrp polypeptides and nucleotides encoding the polypeptides (coding sequences) are described below. The Sfrp polypeptides, mature processed forms, and/or fragments thereof are used in the cardioprotective and repair methods described herein.

Human SFRP1 mRNA sequence (SEQ ID NO: 4)

```
   1 cctgcagcct ccggagtcag tgccgcgcgc ccgccgcccc gcgccttcct gctcgccgca
  61 cctccgggag ccggggcgca cccagcccgc agcgccgcct ccccgcccgc gccgcctccg
 121 accgcaggcc gagggccgcc actggccggg gggaccgggc agcagcttgc ggccgcggag
 181 ccgggcaacg ctggggactg cgccttttgt ccccggaggt ccctggaagt ttgcggcagg
 241 acgcgcgcgg ggaggcggcg gaggcagccc cgacgtcgcg gagaacaggg cgcagagccg
 301 gcatgggcat cgggcgcagc gagggggggcc gccgcggggc agccctgggc gtgctgctgg
 361 cgctgggcgc ggcgcttctg gccgtgggct cggccagcga gtacgactac gtgagcttcc
 421 agtcggacat cggcccgtac cagagcgggc gcttctacac caagccacct cagtgcgtgg
 481 acatccccgc ggacctgcgg ctgtgccaca acgtgggcta caagaagatg gtgctgccca
 541 acctgctgga gcacgagacc atggcggagg tgaagcagca ggccagcagc tgggtgcccc
 601 tgctcaacaa gaactgccac gccggcaccc aggtcttcct ctgctcgctc ttcgcgcccg
 661 tctgcctgga ccggcccatc tacccgtgtc gctggctctg cgaggccgtg cgcgactcgt
 721 gcgagccggt catgcagttc ttcggcttct actggcccga gatgcttaag tgtgacaagt
 781 tccccgaggg ggacgtctgc atcgccatga cgccgcccaa tgccaccgaa gcctccaagc
 841 cccaaggcac aacggtgtgt cctccctgtg acaacgagtt gaaatctgag gccatcattg
 901 aacatctctg tgccagcgag tttgcactga ggatgaaaat aaaagaagtg aaaaaagaaa
 961 atggcgacaa gaagattgtc cccaagaaga agaagcccct gaagttgggg cccatcaaga
1021 agaaggacct gaagaagctt gtgctgtacc tgaagaatgg ggctgactgt ccctgccacc
1081 agctggacaa cctcagccac cacttcctca tcatgggccg caaggtgaag agccagtact
1141 tgctgacggc catccacaag tgggacaaga aaaacaagga gttcaaaaac ttcatgaaga
1201 aaatgaaaaa ccatgagtgc cccacctttc agtccgtgtt taagtgattc tcccgggggc
1261 agggtgggga gggagcctcg ggtggggtgg gagcgggggg gacagtgccc cgggaacccg
1321 gtgggtcaca cacacgcact gcgcctgtca gtagtggaca ttgtaatcca gtcggcttgt
1381 tcttgcagca ttcccgctcc cttccctcca tagccacgct ccaaacccca gggtagccat
1441 ggccgggtaa agcaagggcc atttagatta ggaaggtttt taagatccgc aatgtggagc
1501 agcagccact gcacaggagg aggtgacaaa ccatttccaa cagcaacaca gccactaaaa
1561 cacaaaaagg gggattgggc ggaaagtgag agccagcagc aaaaactaca ttttgcaact
1621 tgttggtgtg gatctattgg ctgatctatg cctttcaact agaaaattct aatgattggc
1681 aagtcacgtt gttttcaggt ccagagtagt ttctttctgt ctgctttaaa tggaaacaga
1741 ctcataccac acttacaatt aaggtcaagc ccagaaagtg ataagtgcag ggaggaaaag
1801 tgcaagtcca ttatgtaata gtgacagcaa agggaccagg ggagaggcat tgccttctct
1861 gcccacagtc tttccgtgtg attgtctttg aatctgaatc agccagtctc agatgcccca
1921 aagtttcggt tcctatgagc ccggggcatg atctgatccc caagacatgt ggaggggcag
1981 cctgtgcctg cctttgtgtc agaaaaagga aaccacagtg agcctgagag agacggcgat
2041 tttcgggctg agaaggcagt agttttcaaa acacatagtt aaaaaagaaa caaatgaaaa
2101 aaattttaga acagtccagc aaattgctag tcagggtgaa ttgtgaaatt gggtgaagag
2161 cttaggattc taatctcatg ttttttcctt ttcacatttt taaaagaaca atgacaaaca
2221 cccacttatt tttcaaggtt ttaaaacagt ctacattgag catttgaaag gtgtgctaga
2281 acaaggtctc ctgatccgtc cgaggctgct tcccagagga gcagctctcc ccaggcattt
```

-continued

```
2341 gccaagggag gcggatttcc ctggtagtgt agctgtgtgg ctttccttcc tgaagagtcc

2401 gtggttgccc tagaacctaa caccccctag caaaactcac agagctttcc gttttttttct

2461 ttcctgtaaa gaaacatttc ctttgaactt gattgcctat ggatcaaaga aattcagaac

2521 agcctgcctg tccccccgca ctttttacat atatttgttt catttctgca gatggaaagt

2581 tgacatgggt ggggtgtccc catccagcga gagagtttca aaagcaaaac atctctgcag

2641 tttttcccaa gtaccctgag atacttccca aagcccttat gtttaatcag cgatgtatat

2701 aagccagttc acttagacaa ctttaccctt cttgtccaat gtacaggaag tagttctaaa

2761 aaaaatgcat attaatttct tcccccaaag ccggattctt aattctctgc aacactttga

2821 ggacatttat gattgtccct ctgggccaat gcttataccc agtgaggatg ctgcagtgag

2881 gctgtaaagt ggccccctgc ggccctagcc tgacccggag gaaaggatgg tagattctgt

2941 taactcttga agactccagt atgaaaatca gcatgcccgc ctagttacct accggagagt

3001 tatcctgata aattaacctc tcacagttag tgatcctgtc cttttaacac ctttttttgtg

3061 gggttctctc tgacctttca tcgtaaagtg ctggggacct taagtgattt gcctgtaatt

3121 ttggatgatt aaaaaatgtg tatatatatt agctaattag aaatattcta cttctctgtt

3181 gtcaaactga aattcagagc aagttcctga gtgcgtggat ctgggtctta gttctggttg

3241 attcactcaa gagttcagtg ctcatacgta tctgctcatt ttgacaaagt gcctcatgca

3301 accgggccct ctctctgcgg cagagtcctt agtggagggg tttacctgga acattagtag

3361 ttaccacaga atacggaaga gcaggtgact gtgctgtgca gctctctaaa tgggaattct

3421 caggtaggaa gcaacagctt cagaaagagc tcaaaataaa ttggaaatgt gaatcgcagc

3481 tgtgggtttt accaccgtct gtctcagagt cccaggacct tgagtgtcat tagttacttt

3541 attgaaggtt ttagacccat agcagctttg tctctgtcac atcagcaatt tcagaaccaa

3601 aagggaggct ctctgtaggc acagagctgc actatcacga gcctttgttt ttctccacaa

3661 agtatctaac aaaaccaatg tgcagactga ttggcctggt cattggtctc cgagagagga

3721 ggtttgcctg tgatttccta attatcgcta gggccaaggt gggatttgta aagctttaca

3781 ataatcattc tggatagagt cctgggaggt ccttggcaga actcagttaa atctttgaag

3841 aatatttgta gttatcttag aagatagcat gggaggtgag gattccaaaa acattttatt

3901 tttaaaatat cctgtgtaac acttggctct tggtacctgt gggttagcat caagttctcc

3961 ccagggtaga attcaatcag agctccagtt tgcatttgga tgtgtaaatt acagtaatcc

4021 catttcccaa acctaaaatc tgtttttctc atcagactct gagtaactgg ttgctgtgtc

4081 ataacttcat agatgcagga ggctcaggtg atctgtttga ggagagcacc ctaggcagcc

4141 tgcagggaat aacatactgg ccgttctgac ctgttgccag cagatacaca ggacatggat

4201 gaaattcccg tttcctctag tttcttcctg tagtactcct cttttagatc ctaagtctct

4261 tacaaaagct ttgaatactg tgaaaatgtt ttacattcca tttcatttgt gttgtttttt
```

-continued 4321 taactgcatt ttaccagatg ttttgatgtt atcgcttatg ttaatagtaa ttcccgtacg 4381 tgttcatttt attttcatgc tttttcagcc atgtatcaat attcacttga ctaaaatcac 4441 tcaattaatc aatgaaaaaa aaaaa Human SFRP1 protein sequence (SEQ ID NO: 5)

MGIGRSEGGRRGAALGVLLALGAALLAVGSASEYDYVSFQSDIGPYQSGR

FYTKPPQCVDIPADLRLCHNVGYKKMVLPNLLEHETMAEVKQQASSWVPL

-continued

LNKNCHAGTQVFLCSLFAPVCLDRPIYPCRWLCEAVRDSCEPVMQFFGFY

WPEMLKCDKFPEGDVCIAMTPPNATEASKPQGTTVCPPCDNELKSEAIIE

HLCASEFALRMKIKEVKKENGDKKIVPKKKKPLKLGPIKKKDLKKLVLYL

KNGADCPCHQLDNLSHHFLIMGRKVKSQYLLTAIHKWDKKNKEFKNFMKK

MKNHECPTFQSVFK

Human SFRP2 mRNA sequence (SEQ ID NO: 6)

1 caacggctca ttctgctccc ccgggtcgga gcccccccgga gctgcgcgcg ggcttgcagc 61 gcctcgcccg cgctgtcctc ccggtgtccc gcttctccgc gccccagccg ccggctgcca 121 gcttttcggg gccccgagtc gcacccagcg aagagagcgg gcccgggaca agctcgaact 181 ccggccgcct cgcccttccc cggctccgct ccctctgccc cctcggggtc gcgcgcccac 241 gatgctgcag ggccctggct cgctgctgct gctcttcctc gcctcgcact gctgcctggg 301 ctcggcgcgc gggctcttcc tctttggcca gcccgacttc tcctacaagc gcagcaattg 361 caagcccatc cctgccaacc tgcagctgtg ccacggcatc gaataccaga acatgcggct 421 gcccaacctg ctgggccacg agaccatgaa ggaggtgctg gagcaggccg gcgcttggat 481 cccgctggtc atgaagcagt gccacccgga caccaagaag ttcctgtgct cgctcttcgc 541 ccccgtctgc ctcgatgacc tagacgagac catccagcca tgccactcgc tctgcgtgca 601 ggtgaaggac cgctgcgccc cggtcatgtc cgccttcggc ttcccctggc ccgacatgct 661 tgagtgcgac cgtttccccc aggacaacga cctttgcatc cccctcgcta gcagcgacca 721 cctcctgcca gccaccgagg aagctccaaa ggtatgtgaa gcctgcaaaa ataaaaatga 781 tgatgacaac gacataatgg aaacgctttg taaaaatgat tttgcactga aaataaaagt 841 gaaggagata acctacatca accgagatac caaaatcatc ctggagacca agagcaagac 901 catttacaag ctgaacggtg tgtccgaaag ggacctgaag aaatcggtgc tgtggctcaa 961 agacagcttg cagtgcacct gtgaggagat gaacgacatc aacgcgccct atctggtcat 1021 gggacagaaa cagggtgggg agctggtgat cacctcggtg aagcggtggc agaaggggca 1081 gagagagttc aagcgcatct cccgcagcat ccgcaagctg cagtgctagt cccggcatcc 1141 tgatggctcc gacaggcctg ctccagagca cggctgacca tttctgctcc gggatctcag 1201 ctcccgttcc ccaagcacac tcctagctgc tccagtctca gcctgggcag cttccccctg 1261 ccttttgcac gtttgcatcc ccagcatttc ctgagttata aggccacagg agtggatagc 1321 tgttttcacc taaaggaaaa gcccacccga atcttgtaga aatattcaaa ctaataaaat 1381 catgaatatt tttatgaagt ttaaaaatag ctcactttaa agctagtttt gaataggtgc 1441 aactgtgact tgggtctggt tggttgttgt ttgttgtttt gagtcagctg attttcactt 1501 cccactgagg ttgtcataac atgcaaattg cttcaatttt ctctgtggcc caaacttgtg -continued

```
1561 ggtcacaaac cctgttgaga taaagctggc tgttatctca acatcttcat cagctccaga
1621 ctgagactca gtgtctaagt cttacaacaa ttcatcattt tataccttca atgggaactt
1681 aaactgttac atgtatcaca ttccagctac aatacttcca tttattagaa gcacattaac
1741 catttctata gcatgatttc ttcaagtaaa aggcaaaaga tataaatttt ataattgact
1801 tgagtacttt aagccttgtt taaaacattt cttacttaac ttttgcaaat taaacccatt
1861 gtagcttacc tgtaatatac atagtagttt acctttaaaa gttgtaaaaa tattgcttta
1921 accaacactg taaatatttc agataaacat tatattcttg tatataaact ttacatcctg
1981 ttttacctat aaaaaaaaaa aaaaa
```

Human SFRP2 protein sequence (SEQ ID NO: 7)

```
MLQGPGSLLLLFLASHCCLGSARGLFLFGQPDFSYKRSNCKPIPANLQLC
HGIEYQNMRLPNLLGHETMKEVLEQAGAWIPLVMKQCHPDTKKFLCSLFA
PVCLDDLDETIQPCHSLCVQVKDRCAPVMSAFGFPWPDMLECDRFPQDND
```

-continued

```
LCIPLASSDHLLPATEEAPKVCEACKNKNDDDNDIMETLCKNDFALKIKV
KEITYINRDTKIILETKSKTIYKLNGVSERDLKKSVLWLKDSLQCTCEEM
NDINAPYLVMGQKQGGELVITSVKRWQKGQREFKRISRSIRKLQC
```

Human SFRP3 mRNA sequence (SEQ ID NO: 8)

```
   1 gttgggaaag agcagcctgg gcggcagggg cggtggctgg agctcggtaa agctcgtggg
  61 accccattgg gggaatttga tccaaggaag cggtgattgc cgggggagga gaagctccca
 121 gatccttgtg tccacttgca gcgggggagg cggagacggc ggagcgggcc ttttggcgtc
 181 cactgcgcgg ctgcaccctg ccccatcctg ccgggatcat ggtctgcggc agcccgggag
 241 ggatgctgct gctgcgggcc gggctgcttg ccctggctgc tctctgcctg ctccgggtgc
 301 ccggggctcg ggctgcagcc tgtgagcccg tccgcatccc cctgtgcaag tccctgccct
 361 ggaacatgac taagatgccc aaccacctgc accacagcac tcaggccaac gccatcctgg
 421 ccatcgagca gttcgaaggt ctgctgggca cccactgcag ccccgatctg ctcttcttcc
 481 tctgtgccat gtacgcgccc atctgcacca ttgacttcca gcacgagccc atcaagccct
 541 gtaagtctgt gtgcgagcgg gcccggcagg gctgtgagcc catactcatc aagtaccgcc
 601 actcgtggcc ggagaacctg gcctgcgagg agctgccagt gtacgacagg ggcgtgtgca
 661 tctctcccga ggccatcgtt actgcggacg gagctgattt tcctatggat tctagtaacg
 721 gaaactgtag aggggcaagc agtgaacgct gtaaatgtaa gcctattaga gctacacaga
 781 agacctattt ccggaacaat tacaactatg tcattcgggc taaagttaaa gagataaaga
 841 ctaagtgcca tgatgtgact gcagtagtgg aggtgaagga gattctaaag tcctctctgg
 901 taaacattcc acgggacact gtcaacctct ataccagctc tggctgcctc tgccctccac
 961 ttaatgttaa tgaggaatat atcatcatgg gctatgaaga tgaggaacgt tccagattac
1021 tcttggtgga aggctctata gctgagaagt ggaaggatcg actcggtaaa aaagttaagc
1081 gctgggatat gaagcttcgt catcttggac tcagtaaaag tgattctagc aatagtgatt
1141 ccactcagag tcagaagtct ggcaggaact cgaacccccg gcaagcacgc aactaaatcc
1201 cgaaatacaa aaagtaacac agtggacttc ctattaagac ttacttgcat tgctggacta
1261 gcaaaggaaa attgcactat tgcacatcat attctattgt ttactataaa aatcatgtga
1321 taactgatta ttacttctgt ttctcttttg gtttctgctt ctctcttctc tcaacccctt
1381 tgtaatggtt tgggggcaga ctcttaagta tattgtgagt tttctatttc actaatcatg
```

-continued

```
1441 agaaaaactg ttcttttgca ataataataa attaaacatg ctgttaccag agcctctttg

1501 ctggagtctc cagatgttaa tttactttct gcaccccaat tgggaatgca atattggatg

1561 aaaagagagg tttctggtat tcacagaaag ctagatatgc cttaaaacat actctgccga

1621 tctaattaca gccttatttt tgtatgcctt ttgggcattc tcctcatgct tagaaagttc

1681 caaatgttta taaaggtaaa atggcagttt gaagtcaaat gtcacatagg caaagcaatc

1741 aagcaccagg aagtgtttat gaggaaacaa cacccaagat gaattatttt tgagactgtc

1801 aggaagtaaa ataaatagga gcttaagaaa gaacattttg cctgattgag aagcacaact

1861 gaaaccagta gccgctgggg tgttaatggt agcattcttc ttttggcaat acatttgatt

1921 tgttcatgaa tatattaatc agcattagag aaatgaatta taactagaca tctgctgtta

1981 tcaccatagt tttgtttaat ttgcttcctt ttaaataaac ccattggtga aagtcccaaa

2041 aaaaaaaaaa aaaaaaaa
```

Human SFRP3 protein sequence (SEQ ID NO: 9)

```
MVCGSPGGMLLLRAGLLALAALCLLRVPGARAAACEPVRIPLCKSLPWNM

TKMPNHLHHSTQANAILAIEQFEGLLGTHCSPDLLFFLCAMYAPICTIDF

QHEPIKPCKSVCERARQGCEPILIKYRHSWPENLACEELPVYDRGVCISP

EAIVTADGADFPMDSSNGNCRGASSERCKCKPIRATQKTYFRNNYNYVIR

AKVKEIKTKCHDVTAVVEVKEILKSSLVNIPRDTVNLYTSSGCLCPPLNV

NEEYIIMGYEDEERSRLLLVEGSIAEKWKDRLGKKVKRWDMKLRHLGLSK

SDSSNSDSTQSQKSGRNSNPRQARN
```

Coronary Disorders

Many patients are either at risk for or have suffered from various types of heart failure, including myocardial infarction, symptomatic or unsymptomatic left ventricular dysfunction, or congestive heart failure (CHF). An estimated 4.9 million Americans are now diagnosed with CHF, with 400,000 new cases added annually. This year over 300,000 Americans will die from congestive heart failure. Without therapeutic invention, cardiac muscle does not normally have reparative potential. The ability to augment weakened cardiac muscle as described herein is a major advance in the treatment of cardiomyopathy and heart failure. Despite advances in the medical therapy of heart failure, the mortality due to this disorder remains high, where most patients die within one to five years after diagnosis.

Coronary disorders are categorized into at least two groups. Acute coronary disorders include myocardial infarction, and chronic coronary disorders include chronic coronary ischemia, arteriosclerosis, congestive heart failure, angina, atherosclerosis, and myocardial hypertrophy. Other coronary disorders include stroke, myocardial infarction, dilated cardiomyopathy, restenosis, coronary artery disease, heart failure, arrhythmia, angina, or hypertension.

Acute coronary disorders result in a sudden blockage of the blood supply to the heart which deprives the heart tissue of oxygen and nutrients, resulting in damage and death of the cardiac tissue. In contrast, chronic coronary disorders are characterized by a gradual decrease of oxygen and blood supply to the heart tissue overtime causing progressive damage and the eventual death of cardiac tissue.

Cytoprotective Compounds

A cytoprotective (i.e., cell protective or regenerative) compound is a compound that that is capable of inhibiting cell damage such as apoptosis induced or oxidative-stress induced cell death. Cytoprotective compounds also include compounds that induce cell repair and regeneration. A cytoprotective compound is a polypeptide or nucleic acid encoding the polypeptide, the expression of which is increased in MSC-Akt cells under hypoxic conditions as compared to normoxic condition. For example, a cytoprotective polypeptide includes Sfrp-1, 2, and/or 3, adipsin, adrenomedullin, chemokine (C-C motif) ligand 2, cysteine rich protein 61, lysyl oxidase-like 2, serine proteinase inhibitor or vascular endothelial growth factor or fragment thereof. Other proteins/polypeptides with cytoprotective and regenerative properties include h1, 5, 8, 12, and 13. In some aspects the compound is a nucleic acid that increases expression of a nucleic acid that encodes a polypeptide or an agonist of a cytoprotective polypeptide.

Therapeutic Methods

The invention provides methods of inhibiting cell or tissue damage and ischemic or reperfusion related injuries. Also included are methods of regenerating injured myocardial tissue. The therapeutic methods include administering to a subject, or contacting a cell or tissue with a composition containing a cytoprotective compound.

Cell/tissue damage is characterized by a loss of one or more cellular functions characteristic of the cell type which can lead to eventual cell death. For example, cell damage to a cardiomyocyte results in the loss contractile function of the cell resulting in a loss of ventricular function of the heart tissue. An ischemic or reperfusion related injury results in tissue necrosis and scar formation.

Injured myocardial tissue is defined for example by necrosis, scarring or yellow softening of the myocardial tissue. Injured myocardial tissue leads to one or more of several mechanical complications of the heart, such as ventricular dysfunction, decrease forward cardiac output, as well as inflammation of the lining around the heart (i.e., pericarditis). Accordingly, regenerating injured myocardial tissue results in histological and functional restoration of the tissue.

The cell is any cell subject to apoptotic or oxidative stress induced cell death. For example, the cell is a cardiac cell such as a cardiomyocyte, a liver cell or a kidney cell. Tissues to be treated include a cardiac tissue, a pulmonary tissue, or a hepatic tissue. For example, the tissue is an muscle tissue such as heart muscle. The tissue has been damaged by disease or deprivation of oxygen.

Cells or tissues are directly contacted with a cytoprotective compound, e.g. by direct injection into the myocardium. Alternatively, the cytoprotective compound is administered systemically. The cytoprotective compounds are administered in an amount sufficient to decrease (e.g., inhibit) apoptosis induced or oxidative stress induced cell death as compared to untreated cells or tissues. Cells undergoing apoptosis are identified by detecting cell shrinkage, membrane blebbing, caspase activation, chromatin condensation and fragmentation as is well know in the art. Cell undergoing oxidative stress are identified by detecting an increase production of reactive oxygen species (ROS). A decrease in cell death (i.e., an increase in cell viability) is measured by using standard cell viability measurements such as BrdU incorporation assay and trypan blue exclusion.

The methods are useful to alleviate the symptoms of a variety disorders, such as disorders associated with aberrant cell damage, ischemic disorders, and reperfusion related disorders. For example, the methods are useful in alleviating a symptom of stroke, myocardial infarction, chronic coronary ischemia, arteriosclerosis, congestive heart failure, dilated cardiomyopathy, restenosis, coronary artery disease, heart failure, arrhythmia, angina, atherosclerosis, hypertension, renal failure, kidney ischemia or myocardial hypertrophy. The disorders are diagnosed and or monitored, typically by a physician using standard methodologies. Alleviation of one or more symptoms of the disorder indicates that the compound confers a clinical benefit, such as a reduction in one or more of the following symptoms: shortness of breath, fluid retention, headaches, dizzy spells, chest pain, left shoulder or arm pain, and ventricular dysfunction Therapeutic Administration The invention includes administering to a subject a composition comprising a cytoprotective compound (also referred to herein as a "therapeutic compound").

An effective amount of a therapeutic compound administered systemically in the range of about 0.1 mg/kg to about 150 mg/kg. Proteins or peptides are administered directly into the heart by injection at a dose of 1-1000 μg. For example, 10, 20, 30, 40, 50, 60, 75, 100 μg are administered by myocardial injection. Effective doses vary, as recognized by those skilled in the art, depending on route of administration, excipient usage, and coadministration with other therapeutic treatments including use of other anti-apoptotic agents or therapeutic agents for treating, preventing or alleviating a symptom of a particular cardiac disorder. A therapeutic regimen is carried out by identifying a mammal, e.g., a human patient suffering from (or at risk of developing) an cardiac disorder, using standard methods.

The pharmaceutical compound is administered to such an individual using methods known in the art. Preferably, the compound is administered orally, nasally, topically or parenterally, e.g., subcutaneously, intraperitoneally, intramuscularly, and intravenously. The compound is administered prophylactically, or after the detection of an cardiac event such as a heart attack. The compound is optionally formulated as a component of a cocktail of therapeutic drugs to treat cardiac disorders. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The therapeutic compounds described herein are formulated into compositions for administration utilizing conventional methods. For example, cytoprotective compounds are formulated in a capsule or a tablet for oral administration. Capsules may contain any standard pharmaceutically acceptable materials such as gelatin or cellulose. Tablets are formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, a conventional filler, and a tableting agent. Other formulations include an ointment, suppository, paste, spray, patch, cream, gel, resorbable sponge, or foam. Such formulations are produced using methods well known in the art.

Cytoprotective compounds are effective upon direct contact of the compound with the affected tissue, e.g. heart muscle. Alternatively, cytoprotective compounds are administered systemically. Additionally, compounds are administered by implanting (either directly into an organ such as the heart or subcutaneously) a solid or resorbable matrix which slowly releases the compound into adjacent and surrounding tissues of the subject. For example, the compound is delivered to the cardiac tissue (i.e., myocardium, pericardium, or endocardium) by direct intracoronary injection through the chest wall or using standard percutaneous catheter based methods under fluoroscopic guidance for direct injection into tissue such as the myocardium or infusion of an inhibitor from a stent or catheter which is inserted into a bodily lumen. Any variety of coronary catheter, or a perfusion catheter, is used to administer the compound. Alternatively, the compound is coated or impregnated on a stent that is placed in a coronary vessel.

The present invention is further illustrated, but not limited, by the following examples.

Example 1

The Family of Secreted Frizzled Related Proteins Mediate Akt-MSC Cardiac Protection and Repair Through Paracrine Mechanisms Loss of myocardial tissue due to ischemia and infarction usually leads to inflammation, scarring and cardiac myocyte hypertrophy. However, since the myocardium has limited endogenous repair and regenerative capacity, these compensatory pathophysiological responses to myocardial damage are frequently inefficient to sustain cardiac function, resulting eventually in cardiac dilation and failure.

Cellular cardiomyoplasty has been proposed as a potential approach for reconstitution of infarcted myocardium and recuperation of cardiac function. Several cell-based strategies have evolved using a variety of alternatives, such as skeletal muscle myoblasts, embryonic stem cells, fetal cardiomyocytes, myocardial stem cells and marrow-derived mesenchymal stem cells (MSC). Among these methods, the use of MSCs has shown much promise for clinical applications.

Protection may result from differentiation of donor cells into cardiomyocytes, fusion of donor cells with host cardiomyocytes, or through enhanced myocardial perfusion. A significant mechanism by which cardiomyocyte survival/function is mediated by stem cells is through paracrine effects.

Intramyocardial transplantation of MSCs overexpressing the survival gene Akt (Akt-MSCs) resulted in reduced infarct size and volume, ventricular remodeling and cardiac dysfunction, 2 weeks after infarction, when compared to hearts transplanted with control MSCs alone. Moreover, conditioned medium from Akt-MSCs provided cytoprotection of cardiac myocytes exposed to hypoxia in vitro and once injected into infarcted hearts dramatically limited the infarct size and prevented ventricular dysfunction within 72 hours. Since this early effect cannot be readily explained by significant regeneration of cardiac myocytes from the donor cells or enhancement of angiogenesis, these data indicate that the observed effect is due to paracrine factors released by the Akt-MSCs that prevent myocyte loss.

Although it has been reported that native MSCs can secrete angiogenic factors and cytokines, the ability of bone marrow derived MSCs, especially Akt-MSCs, to produce factor(s) capable of acutely protecting the cardiomyocytes from cell death has not been previously documented. Given that apoptosis is the principal cause of myocytes loss in the acute phase of MI, therapeutic methods that prevent or reduce apoptotic cell death are effective in reducing the severity and extent of myocardial infarction. Paracrine factor(s) secreted by MSCs were identified, and biological evidence of their therapeutic potential is described below.

A strategy was developed that allows large-scale identification and functional screening of secreted factors that are responsible for the enhanced cytoprotective effect of the Akt-MSCs. First, microarray analysis of Akt-MSC and control MSC under normoxia and 6 h of hypoxia was performed. Approximately 62 transcripts that were differentially regulated between the Akt-MSC and control MSC under normoxia or hypoxia encode for known secreted proteins based on their annotation. Included in this list were three members of the secreted Frizzled-related protein (Sfrp) family, Sfr1, Sfrp2 and Sfrp3. Sfrps bind to Wnt ligands or their frizzled receptors and modulate Wnt signaling. All three factors are associated with regulation of cell fate, differentiation, and cell death and cell growth. The data described herein provide evidence that Akt-MSCs exert an early protection to the injured heart by secreting Sfrps, which then modulate the X pathway in cardiac myocytes to prevent cell death.

The following material and methods were used to generate the data described below.

Purification of Mesenchymal Stem Cells and Retroviral Transduction.

Bone marrow cells from 8-10 week-old wild type male C57BL/6J mice (Jackson Laboratory), were collected in a-modified minimum essential media supplemented with 17% fetal bovine serum; 100 units/ml penicillin, 100 mg/ml streptomycin; amphotericin B 0.25 mg/ml. Mononuclear cells were then isolated from aspirates by Ficoll-Paque (Amersham Biosciences) gradient centrifugation. For the retroviral transduction, murine Akt1cDNA tagged with a c-myc epitope by PCR-amplification was cloned into pMSCV-IRES-GFP vector. To overexpress Akt/GFP (Akt-MSC) or GFP alone (GFP-MSC), MSCs were infected with high-titer VSV-G pseudotyped retrovirus.

Gene Expression Profiling and RNA Validation

Eight micrograms of total RNA from mouse GFP-MSCs and Akt-MSCs (n=3 per group) under normoxia or hypoxia (6 hours) were used for microarray analysis. Affymetrix GeneChips of Mouse Genome 430 2.0 Arrays (Affymetrix. CA), which allows analysis of ~45000 transcrips, was performed in triplicate, and analyzed with Affymetrix Microarray Suite (MAS 5.0). For further analysis various Dhip was used. All possible comparisons (Akt-MSC normoxia vs. GFP-MSC normoxia, Akt-MSC hypoxia vs. GFP-MSC hypoxia, GFP-MSC hypoxia vs. GFP-MSC normoxia and Akt-MSC hypoxia vs. Akt-MSC normoxia) were tested. The transcripts were then annotated using various databases to compile a list of potent secreted candidates.

Gene expression profiling was determined by quantitative real-time RT-PCR (QPCR) for selected genes with appropriate primer mixtures (TaqMan® Gene Expression Assays, No. 4331182) from Applied Biosystems (Sfrp1, Mm00489161; Sfrp2, Mm00485986; Sfrp3(Frzb), Mm00441378; Gapdh, Mm99999915).

Conditioned Media Collection and Concentration

Passage 3 to 5 GFP-MSCs and Akt-MSCs reached to 90% confluence in 10 cm dishes. The cells were then left either into a standard incubator or the hypoxic chamber in the medium (αMEM+0.2% FBS+ITS) for 6 hours. Plates with medium only were also left at the same conditions as control-conditioned medium. The medium was concentrated up to 50× using a Millipore system with membrane (Amicon Ultra-15).

Western Blotting

Proteins from conditioned medium from MSCs were separated by SDS page gel (Invitrogen) and transferred to nitrocellulose membranes (Bio-Rad). The blots were incubated with Sfrp2 primary antibody (Santa Cruz Biotechnology, Inc.) and then with appropriate secondary antibody conjugated with horseradish peroxidase (Amersham Biosciences). Complexes were detected by chemiluminescence (LumiGLO, Cell Signaling).

Suppression of Secreted Factor Effect by siRNA

GFP-MSCs or Akt-MSCs were incubated overnight with OptiMEM medium containing 1 μM siRNA for Sfrps (Sfrp1, sense (5'→3'): CGGAUUGUAAAGAACUGCATT (SEQ ID NO:10), antisens (5'→3'): UGCAGUUCUUUACAAUCCGTT (SEQ ID NO:11); Sfrp2, sense (5'→3'): GGACGACAACGACAUCAUGTT (SEQ ID NO:12), antisense (5'→3'): CAUGAUGUCGUUGUCGUCCTC (SEQ ID NO:13); Sfrp3, sense (5'→3'): CCGUCAAUCUUUAUACCACTT (SEQ ID NO:14), antisense (5'→3'): GUGGUAUAAAGAUUGACGGTG (SEQ ID NO:15); Ambion). Rhodamine-labeled GFP siRNA (Qiagen) was used to assess the efficiency of transfection. Cells were incubated in normal medium for 48 hours, then exposed to a serum free medium (αMEM+0.2% FBS+ITS) at normoxia or hypoxia as described above. The medium was concentrated for further analysis. The efficiency of the siRNA-mediated reduction of Sfrps was assessed by QPCR using 18S as a control.

Adult Rat Ventricular Myocyte Isolation and Quantification of Apoptotic Cardiomyocytes Adult rat ventricular myocytes (ARVMs) were isolated by enzymatic dissociation. $1\times10^6$ cells were incubated in 10 cm dishes (Becton Dickinson) overnight with full 199 medium (0.2% albumin, 2 mM carnitine, 5 mM creatine, 5 mM taurine and 1 μg/ml of recombinant human insulin, Sigma). On the following day, the medium was replaced with optimal medium according to different assays. Hypoxic condition was created by incubating the cells at 37° C. into a hypoxia chamber with an atmosphere of 5% $CO_2$/95% $N_2$. Oxygen level into the chamber was controlled to 0.5%.

Apoptosis was determined by measuring the activity of cleaved-caspase 3 using a caspase-specific fluorogenic substrate according to the protocol for Caspase 3 assay kit (Sigma, St. Louis, Mo.). ARVMs were lysed after treatment with SFRPs for 24 hours under hypoxia. 5 ul of cell extract was incubated in reaction buffer at room temperature for 1 hour. The enzyme-catalyzed release of 7-amino-4-methyl coumarin (AMC) was measured by a fluorescence microplate reader. Fluorescent units were converted to pmole AMC/μl sample/min/μg protein, using a standard curve of AMC.

Quantitation of Morphologic Changes of ARVC Following Hypoxic Exposure

Isolated cardiomyocytes were seeded in multi-well plates (Becton Dickinson, Franklin Lakes, N.J., USA) precoated with laminin (1 $\mu g/cm^2$) and left overnight in standard growth medium (M199). One day later, the medium was replaced by serum-free medium with different doses of Sfrp2. The ARVCs were then placed in the hypoxia chamber. The viability of the ARVCs was evaluated on the basis of their morphology using a phase contrast microscope, and rod-shaped cardiomyocytes were considered viable. The number of round shaped cardiomyocytes was counted in 6 random high power fields and expressed as a percentage of total number of cells.

Myocardial Infarction Model and Determination of Infarct Size

Ligation of the left anterior descending coronary artery was performed on 170 to 200 grams female Sprague Dawley rats (Harlan World Headquarters, Indianapolis, Ind.). A left thoracotomy was performed under anesthesia, and the vessel was ligated with a silk suture at midway between the left atrium and the apex of the heart. The infarction was then assessed by the change of color and kinesis of the apex and the anterior-lateral wall. Thirty minutes later 250 μl conditioned media was injected in 5 different sites around the border zone. An equivalent amount of PBS was injected in the control group. Then the wound was sutured immediately.

Infarct size was analyzed by staining the tissue 5 min at 37° C. with planar morphometry in triphenyl tetrazolium chloride (TTC, Sigma Chemicals) followed by fixation of 12 hours in 10% phosphate-buffered formalin, and expressed as a percentage of the total ventricular area.

Akt Regulated Expression of Sfrps in MSCs

Since the secreted frizzled-related sequence, protein 2 (Sfrp2) appeared to be expressed highly only in Akt-MSCs, and two other members of the same family (Sfrp1 and Sfrp3) were also upregulated in these cells, efforts were focused on these molecules. First, MSCs-Akt and control Gfp-MSCs were cultured under normoxia or 6 hours of hypoxia and the RNA was collected and used to confirm the microarray data by quantitative PCR (Q-PCR). The expression pattern of all genes Sfrp1, Sfrp2 and Sfrp3 was consistent with the microarray results. Although both Sfrp1 and Sfrp3 exhibited a consistent trend ($P<0.1$) of being expressed higher in Akt-MSCs, the most dramatic and significant differences were shown in the Sfrp2 levels (almost undetectable in control cells as opposed to high levels in Akt-MSCs). No significant changes were observed in the levels of all three genes in regard to hypoxia treatment in either control MSC or Akt-MSCs.

To further validate the observations at the protein level and to evaluate the effect of Akt on Sfrp2 expression, control mouse MSCs and Akt-MSCs were cultured under normoxic or hypoxic conditions for 6 hours with PI3K inhibitor (LY294002 50 mM) or vehicle. The conditioned medium was then collected and concentrated for protein analysis. Sfrp2 was highly expressed in the conditioned medium from the Akt-MSC cells at both normoxia and hypoxia. The levels of Sfrp2 were low or undetectable in the supernatant from GFP-MSCs under normoxia or hypoxia. Furthermore, the expression of Sfrp2 in the Akt-MSC cells was dependent to the PI3K pathway since inhibition of the PI3K, also abolished Sfrp2 expression from the medium. Sfrp1 and Sfrp3 showed similar patterns of protein expression.

Akt-MSCs Promote Cardiac Myocyte Cell Survival After Injury Through Sfrp Mediated Paracrine Effects To determine whether Sfrps are a key mediator of the early cytoprotective effect of the conditioned medium in vitro, the effects of conditioned medium from cultured Akt-MSCs (Akt CM) and Akt-MSCs that did not express Sfrp1, Sfrp2 or Sfrp3 due to siRNA treatment (Akt-Sfrp2 CM) on the viability of adult rat cardiac myocytes (ARVCs) subjected to hypoxia were assessed. The conditioned media (CM) from Akt-MSCs of Gfp-MSCs was collected and concentrated after 6 hours of exposure to either normoxia or hypoxia. The CM was then added to ARVCs that were exposed to 24 h of hypoxia. The experimental conditions included ARVCs that were incubated with either control conditioned medium (Ctr CM), conditioned medium from Akt-MSCs or Gfp-MSCs (Akt CM and Gfp CM) and conditioned medium Akt-MSCs or Gfp-MSCs that did not express Sfrp2 due to siRNA treatment (Akt minus Sfrp2 CM and Gfp minus Sfrp2 CM respectively). The data showed that ARVCs maintained under normoxic conditions for 24 hours were viable and exhibited their typical rod-shaped appearance. Exposure of ARVCs to 24 hours of hypoxia in control conditioned medium (Ctr CM) resulted in a 200% increase in cell death as indicated by caspase activity assay. Moreover, as expected the addition of Gfp CM had no effect whereas addition of Akt CM resulted in a reduction of caspase activity (64% as compared to Ctr CM) to levels similar to normoxic conditions. However, exposure of hypoxic myocytes to Akt minus Sfrp2 CM resulted in increased caspase activity compared to Ctr CM indicating higher cell death levels. Finally, reduction of Sfrp2 expression in the Gfp CM did not have did not have any significant impact on its effect on hypoxic cardiac myocytes.

To examine the direct effect of Sfrps on ARVCs we also performed gain of function experiments in vitro. ARVCs were maintained in standard growth medium at normoxia or at 24 h hypoxia. Sfrp1, Sfrp2, Sfrp3 or vehicle was then added at various concentrations and apoptosis levels were assessed as before by measuring caspase activity. Treatment with as low as 0.1 ng/ml of Sfrp1 or Sfrp2 resulted in significant reduction in caspase activity (36% and 33% respectively). However, higher concentrations of Sfrp1 showed reduced protection. On the contrary, Sfrp2 mediated reduction of cell death was positive correlated to higher concentrations of the molecule and seemed to plateau around the concentration of 10 ng/ml (55% reduction in caspase activity). Sfrp3 treatment reduced caspase activity only in concentrations higher than 10 ng/ml and overall was less potent that the other molecules (54% reduction at 500 ng/ml).

Finally, to corroborate the results from the apoptosis assays, the relative number of healthy ARVCs after 24 hours of hypoxia was assessed based on their ATP synthesis levels. For this, again the cells were grown in normoxia or hypoxia with PBS or Akt CM, Akt-Sfrp2 CM, 10 ng/ml Sfrp2, or 500 ng/ml Sfrp3 for 24 h. Exposure of ARVCs to 24 h plus Akt CM increased cell viability by 35% whereas medium from Akt cells that did not express Sfrp2 increased cell viability only by 9%. Treatment with Sfrp2 and Sfrp3 resulted in 24% and 17% increase in viability respectively.

Sfrp Treatment Protects the Heart from Myocardial Injury

To elucidate the therapeutic potential of the Sfrps, we studied the direct effects of Sfrps on infarct size by intramyocardial injection of Sfrp1, Sfrp2 or Sfrp3 peptide. For this, 1 μg of Sfrp1, Sfrp2 or Sfrp3 were injected into 5 different sites in the heart at the infarct border zone 30 minutes after coronary artery occlusion. Additional groups included hearts injected with PBS as negative control, hearts injected with Akt CM as positive control and hearts injected with Akt minus Sfrp2 CM to provide further evidence of Sfrp2 role in the protective Akt-MSC CM mediated cardiac protection in vivo. Hearts were isolated 72 hours later and infarct size was estimated by TTC staining. Injection of Sfrp2 had an effect of 69% reduction of infarct size, while injection of the same concentration of Sfrp1 resulted in 50% reduction in infarct size and the same dose of Sfrp3 did not have any effect on infarct size. Since Sfrp2 have been shown to have the most potent effect from all the three Sfrps tested, its physiological significance in Akt-MSC mediated myocardial protection in vivo was also evaluated. Injection of Akt CM in infarcted hearts resulted in 71% reduction in the infarct size after MI within 72 hours, whereas injection Akt minus Sfrp2 CM did not show any significant protection. These results indicate that Sfrps secreted from Akt-MSCs protects the myocardium from injury.

Sfrps Mediate Cardioprotection

Despite vigorous efforts and the great potential of cell-based therapies for cardiac disease, the mechanisms underlying their therapeutic effect are still under debate. The data described herein indicates that MSCs exert an early protective effect in the injured myocardium by preventing myocyte cell death. This effect is enhanced by the overexpression of Akt and includes paracrine factors that regulate the Wnt signaling pathway in cardiac myocytes. Sfrp modulators of Wnt pathway protect from hypoxia cell death in vitro and result in reduction of infarct size in vivo.

Members of the Secreted frizzled-related protein (Sfrp) family act as modulators of the Wnt signaling pathway thereby influencing a range of biological processes, such as cell fate, cell adhesion, differentiation and survival. Sfrps are inhibitors of the Wnt signaling pathway. They act through binding of Wnts and altering their ability to bind to their frizzled receptors or by forming non functional complexes with the frizzled receptors themselves. However, some studies suggest that Sfrp1 at low concentrations may actually promote Wnt signaling. Furthermore, it has been reported that similar concentrations of Sfrp1 and Sfrp2 result in different cellular responses. For instance, Sfrp1 has been shown to sensitize cells to TNF induced apoptosis whereas Sfrp2 conferred resistance. A proposed explanation for these observations is that the Sfrp specific effects are closely dependent on the range of their Wnt partners present, the relative affinities of different Sfrps for Wnt or Frizzled receptors, tissues specific responses or biphasic responses to different concentrations of Sfrp. The present data support this mechanis, since the three different Sfrps tested confered variable degrees of protection to cardiac myocytes and these effect was dependent on their concentration levels.

Prior to the invention, little was known about the role of Sfrps in cardiac tissue. Sfrp1 has been associated with heart morphogeneiss, whereas Sfpr3 and Sfrp4 were found to be upregulated in volume overload induced hypertrophy. Evidence suggests that they are play a role during cardiac ischemia but again their role is diverse and not fully understood. For instance, overexpression of Sfrp1 seemed to protect the heart from injury in a model of coronary ligation but has been reported to alleviate it and reverse the benefit of preconditioning in a model of ischemia/reperfusion. Similarly few studies have been conducted in regard to the role of Wnt singaling in cardiac myocyte survival. The present data provides evidence that Sfrp activates/inhibits Wnt signaling.

The data do not exclude additional paracrine effects from other proteins secreted by the Akt-MSCs. Indeed, other secreted molecules are also expressed and are involved in different aspects of cardiac repair such as immunological responses, angiogenesis, recruitment/expansion of cardiac stem cells, regeneration and/or remodeling. For example, administration of vascular endothelial growth factor A (a growth factor with higher levels in Akt-MSCs) resulted in repaired myocardium by promoting angiogenesis and vascularization. Moreover, paracrine factors exert not only individual effects, but in some examples, one factor enhances the effect of another, i.e, a synergistic relationship is present between the different secreted factors expressed by the MSCs. In other examples, the presence of one factor inhibits the effects of one or more others.

Paracrine factors, e.g., Sfrps, contained in conditioned medium from Akt-MSCs are useful in therapeutic methods to prevent or reduce cell death, e.g., apoptotic cell death, of cardiac cells. The data indicates that simple administration of Sfrp2 alone or in combination with other molecules achieve cardioprotective results similar and in some cases better than those seen with stem cell based therapy. Methods that employ these paracrine factors have numerous advantages over cell based therapies. For example, many of the difficulties of stem cell based therapy such as availability of cells, laborious maintenance of cell lines, limited alternative administration methods as well as difficulties in successful delivery and survival of the cells can be avoided. Administration of a peptide or a cocktail of peptides to the injured myocardium is a simpler, delivery methods, and dosages are more easily modified to achieve higher efficiency with lower toxicity or side effects and does not involve any of the ethical concerns associated with cell therapy.

Example 2

Secreted Frizzled Related Protein 2 is the Key Stem Cell Paracrine Factor Mediating Myocardial Survival and Repair Using a comprehensive functional genomic strategy, Sfrp2 was shown to be a key stem cell paracrine factor that mediates myocardial survival and repair following ischemic injury. Sfrp2 modulates Wnt signaling, and cardiomyocytes treated with secreted frizzled related protein increase cellular β-catenin and up-regulate expression of anti-apoptotic genes. These findings demonstrate the key role played by Sfrp2 in mediating the paracrine effects of Akt mesenchymal stem cells on tissue repair and identify modulation of Wnt signaling as a strategy for treating heart disease.

Microarray data confirmed by Western blot analysis demonstrated that one of the most prominently expressed and secreted protein by Akt-MSC compared to native MSC is the Sfrp2. Quantitative PCR showed 100 fold up regulation of Sfrp2 mRNA in Akt-MSC compared to control MSC. Sfrps are secreted glycoprotein molecules that structurally resemble cell surface frizzled receptors but lack the transmembrane domain. They have been increasingly recognized as potent regulators of cellular Wnt signaling and have been implicated in diverse cellular processes such as regulation of cell fate, differentiation, proliferation and cell death.

Sfrp2 was found to play a major role in mediating the survival signal of Akt-MSC on the ischemic myocardium. The data shows that Sfrp2 exerted survival effects on ischemic cardiomyocytes and that the pro-survival effects of Akt-MSC were markedly attenuated upon knockdown of Sfrp2 using siRNA. Sfrp2 increased total cellular and nuclear β-catenin in cardiomyocytes in vitro. Stabilization of β-catenin has been demonstrated to protect neonatal rat cardiomyocytes against hypoxia/re-oxygenation induced apoptosis. The canonical Wnt, Wnt3a, was found to be up-regulated in ischemic cardiomyocytes in vitro, and Wnt3a induced apoptosis of cardiomyocytes. Sfrp2 blocked the pro-apoptotic effect of Wnt3a. The data indicate that Sfrp2 is a major paracrine mediator of Akt-MSC myocardial survival and reparative effects and indicate that modulators of Wnt signaling such as Sfrp2 are useful as therapeutic agents in the management of myocardial injury.

Experiments were carried out as described above. Further profiling of secreted factors to identify cytoprotective proteins is described below.

Profiling of Secreted Factors Expressed in MSCs

To identify potential Akt-MSC secreted candidate paracrine factors mediating myocardial cell survival following ischemic injury, Affymetrix GeneChip® Mouse Genome 430 2.0 Arrays, which allows analysis of approximately 45,000 transcripts was used. Expression levels and quality analysis were carried out with the Affymetrix MAS 5.0 software. Further analysis was performed using the dChip software based on the following filtering criteria: a) Transcripts expressed (P call) in at least one of the sample compared, b) Fold change: at least 1.2×, (90% lower bound confidence). Approximately 650 transcripts were differentially regulated between the Akt-MSC and the GFP-MSC. Included in this list were 169 transcripts with unassigned function. The set of 650 transcripts was queried for transcripts coding for secreted proteins. This analysis revealed 62 transcripts encoding for 51 unique genes that contribute to the paracrine effects of the MSC cells (Table 1).

TABLE 1

| Probe set | Gene Title | Gene Symbol | Fold change Akt vs. Gfp at normoxia | Fold change Akt vs. Gfp at hypoxia |
|---|---|---|---|---|
| 1426858_at | inhibin beta-B | Inhbb | −2.27 | −4.34 |
| 1423635_at | bone morphogenetic protein 2 | Bmp2 | −3.82 | −3.19 |
| 1456404_at | a disintegrin-like and metalloprotease (reprolysin type) with thrombospondin type 1 motif, 5 (aggrecanase-2) | Adamts5 | −1.22 | −3.08 |
| 1426152_a_c | kit ligand/stem cell factor | Kitl | −1.64 | −2.78 |
| 1427760_s_at | Proliferin | Plf | −3.15 | −2.61 |
| 1431056_a_at | lipoprotein lipase | Lpl | −2 | −2.58 |
| 1450658_at | a disintegrin-like and metalloprotease (reprolysin type) with thrombospondin type 1 motif, 5 (aggrecanase-2) | Adamts5 | −1.71 | −2.21 |
| 1449528_at | c-fos induced growth factor | Figf | −2.27 | −2.14 |
| 1438953_at | c-fos induced growth factor | Figf | −3.02 | −2.09 |
| 1415904_at | lipoprotein lipase | Lpl | −1.55 | −2.08 |
| 1418450_at | immunoglobulin superfamily containing leucine-rich repeat | Islr | −1.55 | −2.06 |
| 1426951_at | cysteine-rich motor neuron 1 | Crim1 | −2.41 | −2 |
| 1437218_at | fibronectin 1 | Fn1 | −1.89 | −1.97 |
| 1438954_x_at | c-fos induced growth factor | Figf | −3.03 | −1.96 |
| 1435603_at | secreted protein SST3 | SST3 | −1.12 | −1.93 |
| 1422561_at | a disintegrin-like and metalloprotease (reprolysin type) with thrombospondin type 1 motif, 5 (aggrecanase-2) | Adamts5 | −1.14 | −1.91 |
| 1418061_at | latent transforming growth factor beta binding protein 2 | Ltbp2 | −2.66 | −1.87 |
| 1451243_at | arginyl aminopeptidase (aminopeptidase B) | Rnpep | −1.34 | −1.86 |
| 1460302_at | thrombospondin 1 | Thbs1 | 1.03 | −1.84 |
| 1417234_at | matrix metalloproteinase 11 | Mmp11 | −1.59 | −1.82 |
| 1438936_s_at | Angiogenin | Ang | 1.18 | −1.82 |
| 1447862_x_at | thrombospondin 2 | Thbs2 | −1.33 | −1.8 |
| 1425985_s_at | mannan-binding lectin serine protease 1 | Masp1 | −1.72 | −1.79 |
| 1448117_at | kit ligand | Kitl | −1.23 | −1.79 |
| 1438937_x_at | Angiogenin | Ang | −1.22 | −1.76 |
| 1416164_at | fibulin 5 | Fbln5 | −1.35 | −1.72 |
| 1448823_at | chemokine (C-X-C motif) ligand 12 | Cxcl12 | −1.1 | −1.62 |
| 1415949_at | carboxypeptidase E | Cpe | −1.33 | −1.6 |
| 1416953_at | connective tissue growth factor | Ctgf | −6.01 | −1.57 |
| 1449187_at | platelet derived growth factor, alpha | Pdgfa | −2.33 | −1.55 |
| 1423396_at | Angiotensinogen | Agt | −2.48 | −1.51 |
| 1421228_at | chemokine (C-C motif) ligand 7 | Ccl7 | −3.4 | −1.25 |
| 1438133_a_at | cysteine rich protein 61 | Cyr61 | −3.93 | −1.18 |
| 1419662_at | Osteoglycin | Ogn | 2.19 | −1.07 |
| 1420380_at | chemokine (C-C motif) ligand 2 | Ccl2 | −6.73 | 1.01 |

TABLE 1-continued

| Probe set | Gene Title | Gene Symbol | Fold change Akt vs. Gfp at normoxia | Fold change Akt vs. Gfp at hypoxia |
|---|---|---|---|---|
| 1416039_x_at | cysteine rich protein 61 | Cyr61 | −4.61 | 1.04 |
| 1417130_s_at | angiopoietin-like 4 | Angptl4 | −1.04 | 1.02 |
| 1421991_a_at | insulin-like growth factor binding protein 4 | Igfbp4 | 2.32 | 1.19 |
| 1416371_at | apolipoprotein D | Apod | 1.88 | 1.34 |
| 1423294_at | mesoderm specific transcript | Mest | 2.21 | 1.34 |
| 1416594_at | secreted frizzled-related sequence protein 1 | Sfrp1 | 2.23 | 1.42 |
| 1450325_at | angiopoietin 4 | Agpt4 | 2.43 | 1.6 |
| 1417634_at | superoxide dismutase 3, extracellular | Sod3 | 4.31 | 1.61 |
| 1417256_at | matrix metalloproteinase 13 | Mmp13 | 2.21 | 1.74 |
| 1417633_at | superoxide dismutase 3, extracellular | Sod3 | 3.23 | 1.78 |
| 1429348_at | sema domain, immunoglobulin domain (Ig), short basic domain, secreted, (semaphorin) 3C | Sema3c | 2.61 | 1.92 |
| 1451866_a_at | hepatocyte growth factor | Hgf | 2.32 | 2.26 |
| 1429679_at | leucine rich repeat containing 17 | Lrrc17 | 2.36 | 2.35 |
| 1452436_at | lysyl oxidase-like 2 | Loxl2 | 1.8 | 2.62 |
| 1431591_s_at | interferon, alpha-inducible protein | G1p2 | 4.75 | 2.71 |
| 1448424_at | secreted frizzled-related sequence protein 3 | Sfrp3 | 3.15 | 3.14 |
| 1419043_a_at | interferon-inducible GTPase 1 | Iigp1 | 3.97 | 3.15 |
| 1419042_at | interferon-inducible GTPase 1 | Iigp1 | 4.61 | 3.55 |
| 1451959_a_at | vascular endothelial growth factor A | Vegfa | −1.07 | 3.64 |
| 1447839_x_at | Adrenomedullin | Adm | −3.72 | 4.03 |
| 1417867_at | Adipsin | Adn | 3.5 | 4.15 |
| 1448254_at | Pleiotrophin | Ptn | 5.21 | 4.48 |
| 1416211_a_at | Pleiotrophin | Ptn | 5.68 | 4.79 |
| 1416077_at | Adrenomedullin | Adm | −2.78 | 8.36 |
| 1419149_at | serine (or cysteine) proteinase inhibitor, clade E, member 1 | Serpine1 | −6.34 | 10.35 |
| 1448201_at | secreted frizzled-related sequence protein 2 | Sfrp2 | 10.04 | 11.66 |

Among these upregulated genes, Sfrp2 was the most dramatically upregulated. Other cytokines such as Vegf, Hgf and FGF were not differentially expressed between Akt-MSC and FP-MSC under normoxic conditions. The expression of Sfrp2 was Akt pathway dependent. The expression of the other Sfrp family members were minimally altered in Akt-MSC (FIG. 1A).

Akt Regulated Expression of Sfrps in MSCs

The results of microarray analysis was confirmed by quantitative PCR (Q-PCR). RNA was collected from cultured Akt-MSC and GFP-MSC that were cultured in vitro. As shown in FIG. 1B, the expression pattern of Sfrp1, Sfrp2 and Sfrp3 was consistent with the microarray results. Neither Sfrp1 and Sfrp3 was significantly upregulated in Akt-MSC vs GFP-MSC, whereas Sfrp2 expression was 100 fold higher in Akt-MSC.

Figure 2:
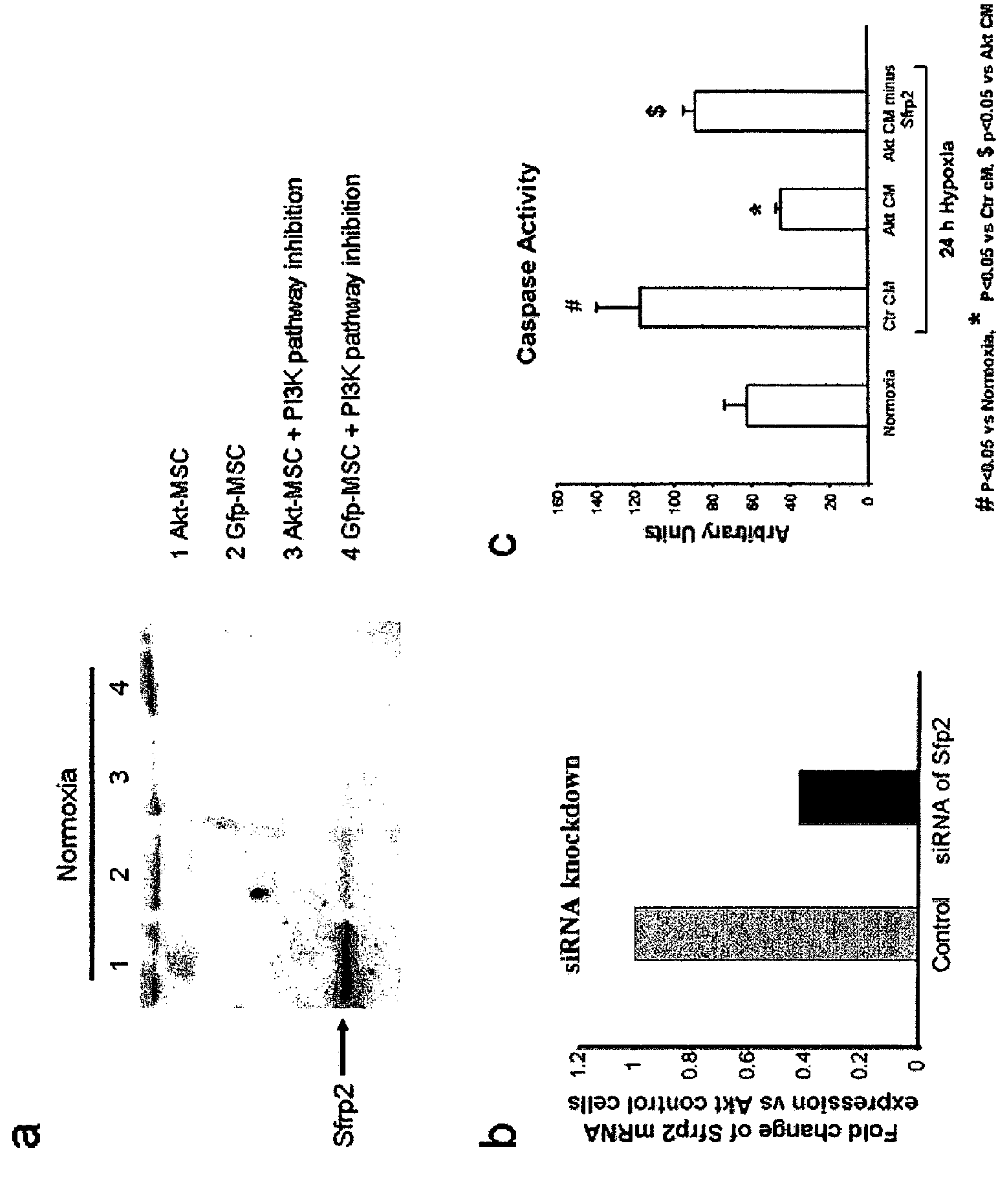
FIG. 2A is a photograph of results of a Western Blotting assay for Sfrp2. The data demonstrates presence of Sfrp2 protein in conditioned medium collected from AKT or GFP MSCs and inhibition of its accumulation in the medium in the presence of Pi3K inhibitor
FIG. 2B is a bar graph showing relative reduction in mRNA levels of Sfrp2 in Akt-MSC following knockdown of Sfrp2 with siRNA.
FIG. 2C is a bar graph showing the effect of conditioned medium on apoptosis in ARVCs. Caspase activity of ARVCs after 24 hours of hypoxia under different culture conditions (control conditioned medium, Ctr CM; Akt conditioned medium, Akt CM; Akt conditioned medium following Sfrp2 knockdown, Akt CM minus Sfrp2) demonstrates reduction of caspase activity following Akt-CM treatment and attenuation of this effect following treatment with Akt CM minus Sfrp2. These data demonstrate that paracrine factors from Akt-MSCs mediate the survival signaling on cardiomycytes.

To further validate our observations at the protein level and to evaluate the effect of Akt on Sfrp2 expression, control mouse MSCs and Akt-MSCs were cultured for 6 hours with PI3Kinase inhibitor (LY294002 50 mM) or vehicle. The conditioned medium was then collected and concentrated for Western blot protein analysis. As shown in FIG. 2A, Sfrp2 was secreted at high levels into the conditioned medium from the Akt-MSC cells (lanes 1). The levels of Sfrp2 were low or undetectable in the conditioned medium of GFP-MSCs (lanes 2). Furthermore, the expression/release of Sfrp2 in the Akt-MSC cells was dependent on the PI3K pathway since inhibition of the PI3K, abolished Sfrp2 accumulation in the medium (lanes 3).

Figure 3:
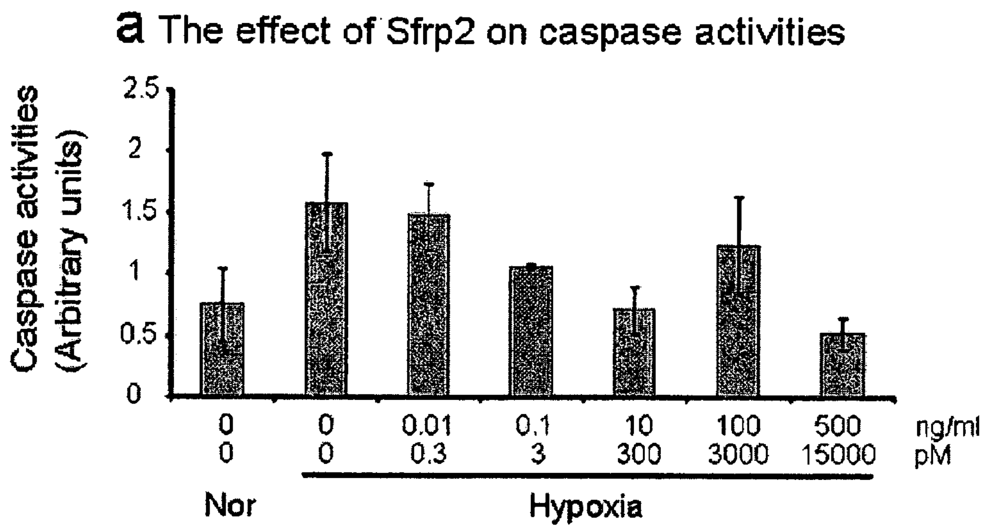
FIG. 3A is a bar graph showing the effect of Sfrp2 on caspase activity. Cleaved-caspase 3 activity as measured by a fluorometric assay demonstrated decreased caspase activity in hypoxic cardiomyocytes following Sfrp2 treatment in a dose dependent manner. The activity was calculated as fold changes with the same control.
FIG. 3B is a bar graph showing the number of round shaped cardiomyocytes that were counted in 6 random high power fields (40×) following 24 hour hypoxic exposure with/without Sfrp2 treatment. Data is expressed as a percentage of total number of cells present.
FIG. 3C is a series of representative high power field photographs demonstrating decreased number of round shaped cardiomyocytes following treatment with Sfrp2. Collectively, these data demonstrate that Sfrp2 decreases caspase 3 activity
Figure 3:
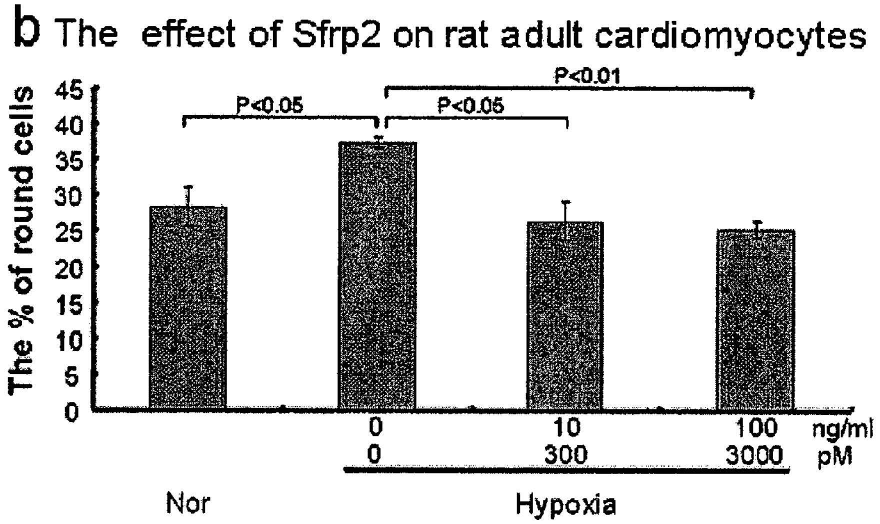
Figure 3:
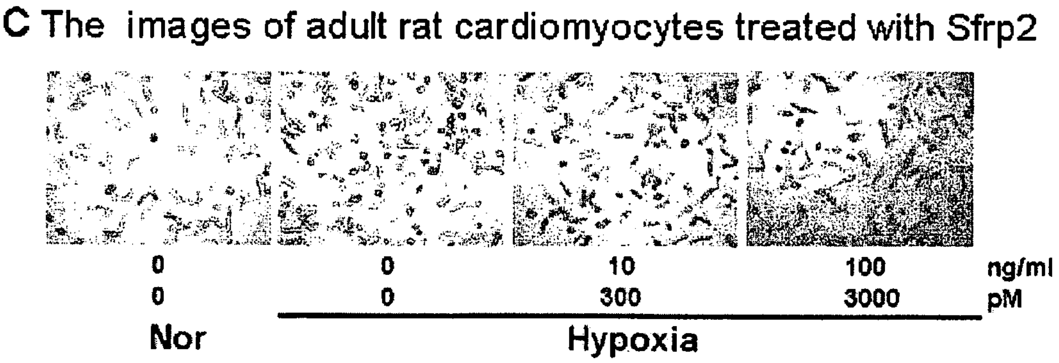

Akt-MSCs Promote Cardiomyocyte Cell Survival Through Paracrine Mechanisms Mediated by Sfrp To prove whether Sfrp2 is a key paracrine mediator of the survival signaling of Akt-MSC, the apoptotic response (caspase activity) of adult rat ventricular cardiomyocytes (ARVC) exposed to conditioned medium collected from Akt-MSC treated with siRNA (Akt-MSC minus Sfrp2 CM) against Sfrp2 was evaluated. ARVC were subjected to hypoxia for 24 hours in the presence of Akt-MSC CM, Akt-MSC minus Sfrp2 CM or standard growth medium (GM). (FIGS. 2B,C). ARVCs maintained in standard growth medium under normoxic conditions for 24 hours were viable and exhibited their typical rod-shaped appearance while ARVC grown in the same medium and subjected to 24 hour hypoxia exhibited a 82% increase in caspase activity (FIG. 2C). Compared to hypoxic ARVC maintained in standard growth medium, hypoxic ARVC exposed to Akt-MSC CM exhibited a 40% reduction in caspase activity (FIG. 3B). Moreover, exposure of hypoxic cardiomyocytes to Akt minus Sfrp2 CM resulted in a significant increase in caspase activity compared to hypoxic ARVC treated with Akt CM. A 33% increase in caspase activity was observed in hypoxic ARVC following knockdown of Sfrp2 expression in Akt-MSC. These observations demonstrate the key role played by Sfrp2 in mediating survival effects of Akt-MSC CM on cardiomyocytes.

To examine the direct effect of Sfrp2 on ARVCs, gain of function experiments were carried out. ARVCs were maintained in standard growth medium at normoxia or subjected to 24 h hypoxia. Sfrp2 or vehicle was then added at various concentrations and apoptosis levels were assessed by measuring caspase activity. Treatment with Sfrp2 resulted in significant reduction in caspase activity, and a dose dependent cytoprotective response was observed with increasing Sfrp2 concentrations up to 15 nM (FIG. 3A).

The cytoprotective effects of Sfrp2 on cardiomyocytes was confirmed by observing changes in cardiomyocyte cell morphology following exposure to hypoxia. ARVC following exposure to 24 hour hypoxia, lose their typical rod shaped morphology, become round in shape, subsequently detach and die. Hypoxia alone increased the number of round shaped cardiomyocytes by approximately 36% (FIGS. 3B, C). However when ARVC were treated with Sfrp2 (3 nM), the number of round shaped cardiomyocytes was decreased by approximately 31% compared to untreated controls (FIGS. 3B, C). The data strongly indicate that Sfrp2 promotes cardiomyocyte survival and protects cardiomyocytes from hypoxic injury.

Suppression of Sfrp2 Expression in Akt-MSCs Reduces the Paracrine Protection of Myocardial Injury In Vivo.

Figure 4:
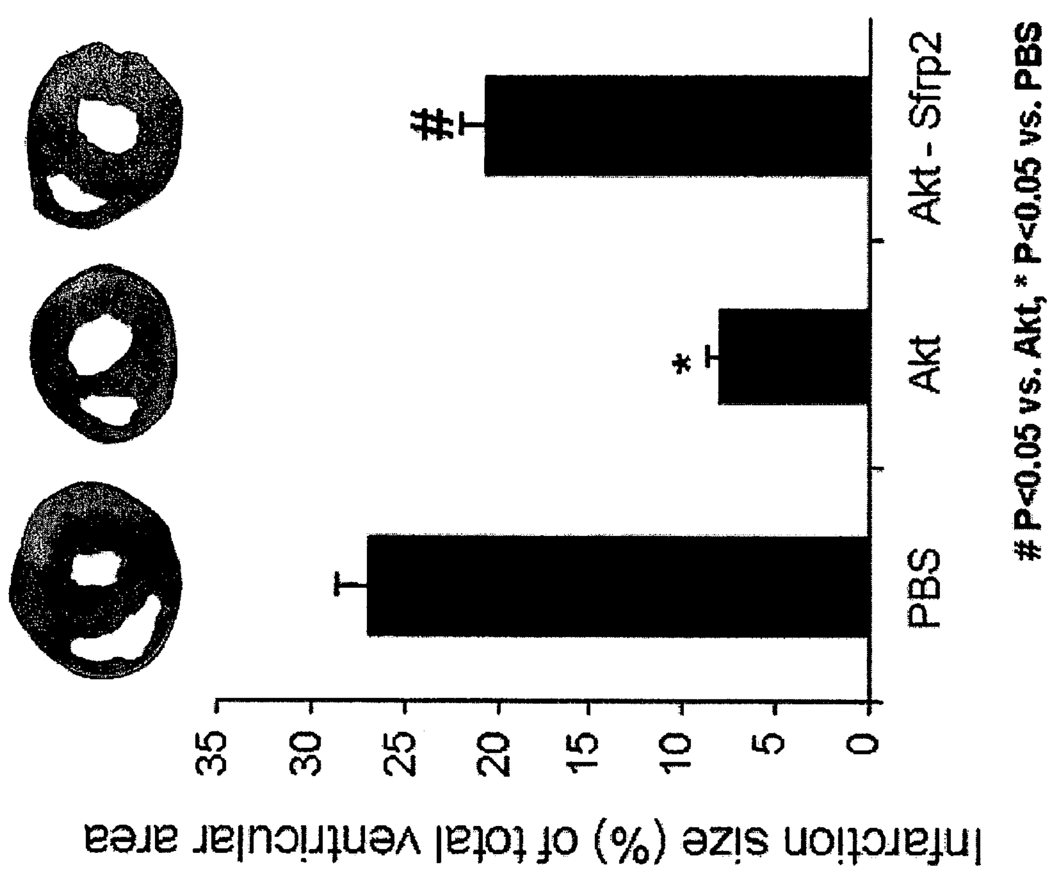
FIG. 4 is a bar graph showing that Sfrp2 decreased cardiac infarct size. Above each bar, is a photograph of TTC staining showing bi-ventricular sections of similar thickness perpendicular to the long axis of the heart. The staining data deomonstrates decreased infarct size with Akt-CM and Sfrp2 and attenuation of reduction in infarct size with Akt-Sfrp2. Infarct size is expressed as a percentage of the total ventricular area. Rat hearts were treated with PBS as control, Akt-MSCs CM (Akt), CM form Akt-MSCs that did express reduced levels of sfrp2 due to siRNA treatment (Akt-Sfrp2).

Experiments were carried out to evaluate the physiological significance of Sfrp2 in Akt-MSC mediated paracrine myocardial protection in vivo. To demonstrate the importance of Sfrp2 as a key paracrine factor mediating prosurvival effects of injected Akt-MSC, in vivo effects of conditioned medium collected from Akt-MSC treated with siRNA against Sfrp2 were compared with those of untreated Akt-MSC CM. Akt-MSC treated with siRNA against Sfrp2 had a 60% decrease in Sfrp2 mRNA expression following 48 hours of exposure to siRNA (FIG. 2B). The conditioned medium either from untreated or siRNA treated cells was collected, concentrated and then injected into 5 different sites at the infarct border zone 30 minutes after coronary artery ligation (a standard model for MI). Hearts were then isolated 72 hours later and infarct size was estimated by TTC staining. The results were analyzed by an investigator blinded to the treatment groups. As shown (FIGS. 4A, B) injection of Akt CM in infarcted hearts resulted in 71% reduction in the infarct size after MI within 72 hours, whereas injection of conditioned medium from siRNA treated Akt-MSC did not show any significant protection. Collectively, these results indicate that Sfrp2 possesses cell survival signaling properties and mediates myocardial protective effects following myocardial infarction.

Sfrp2 Leads to Upregulation of βCatenin in Hypoxic Cardiomyocytes

Figure 5:
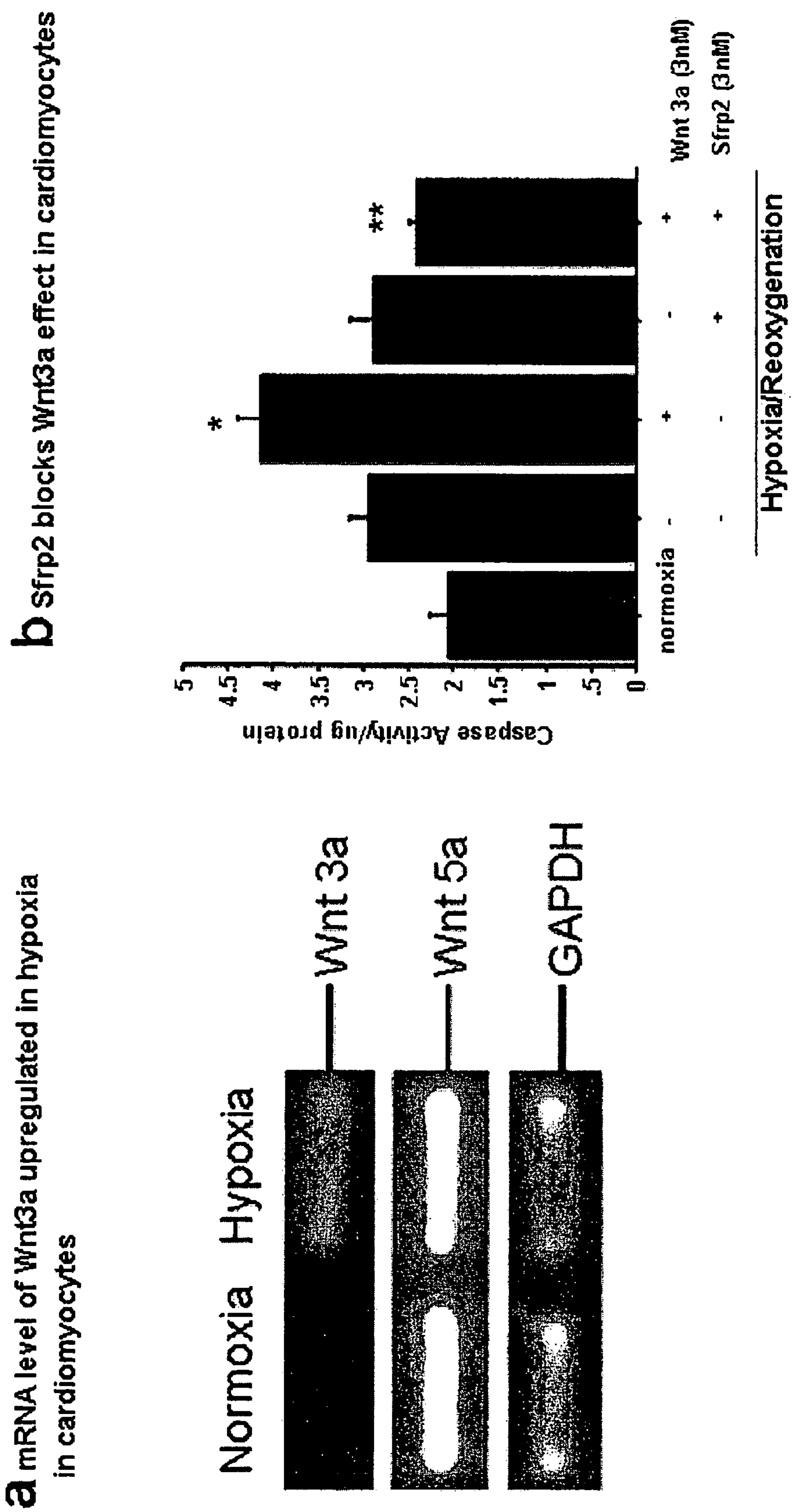

Sfrp2 is an antagonist of Wnt signaling. Unlike Sfrp1 which can potentiate Wnt signaling under certain conditions, Sfrp2 has not been known to activate Wnt signaling. However, evidence described herein indicates that Sfrp2 increases total cellular as well as nuclear β catenin mimicking canonical Wnt signaling. Using Western blotting, Sfrp2 was found to induce a dose dependent increase in nuclear as well as total cellular β catenin levels in cardiomyocytes exposed to hypoxia (FIG. 5C). Increased β catenin within cardiomyocytes is associated with increased cellular protection against ischemic injury in vitro. These data indicate that Sfrp2 promotes the survival of cardiomyocytes against hypoxia induced apoptosis via potentiation of canonical signaling.

Experiments were then carried out to determine if Wnts are up-regulated in cardiomyocytes exposed to 24 hour hypoxia. The data indicated that Wnt3a was expressed at very low levels in normoxic cells but increased in hypoxic cells (FIG. 5A). Cardiomyocytes were incubated both under normoxia and hypoxia/reoxygenation with Wnt3a alone and in combination with Sfrp2. The data demonstrated that under normoxic conditions, as compared to control cardiomyocytes Wnt3a treatment resulted in a modest increase in caspase 3 activity which was attenuated by Sfrp2 treatment. Furthermore, under hypoxia/reoxygenation conditions, Wnt3a treatment resulted in a significant increase in caspase activity which was inhibited by the addition of Sfrp2 (FIG. 5B).

Figure 6:
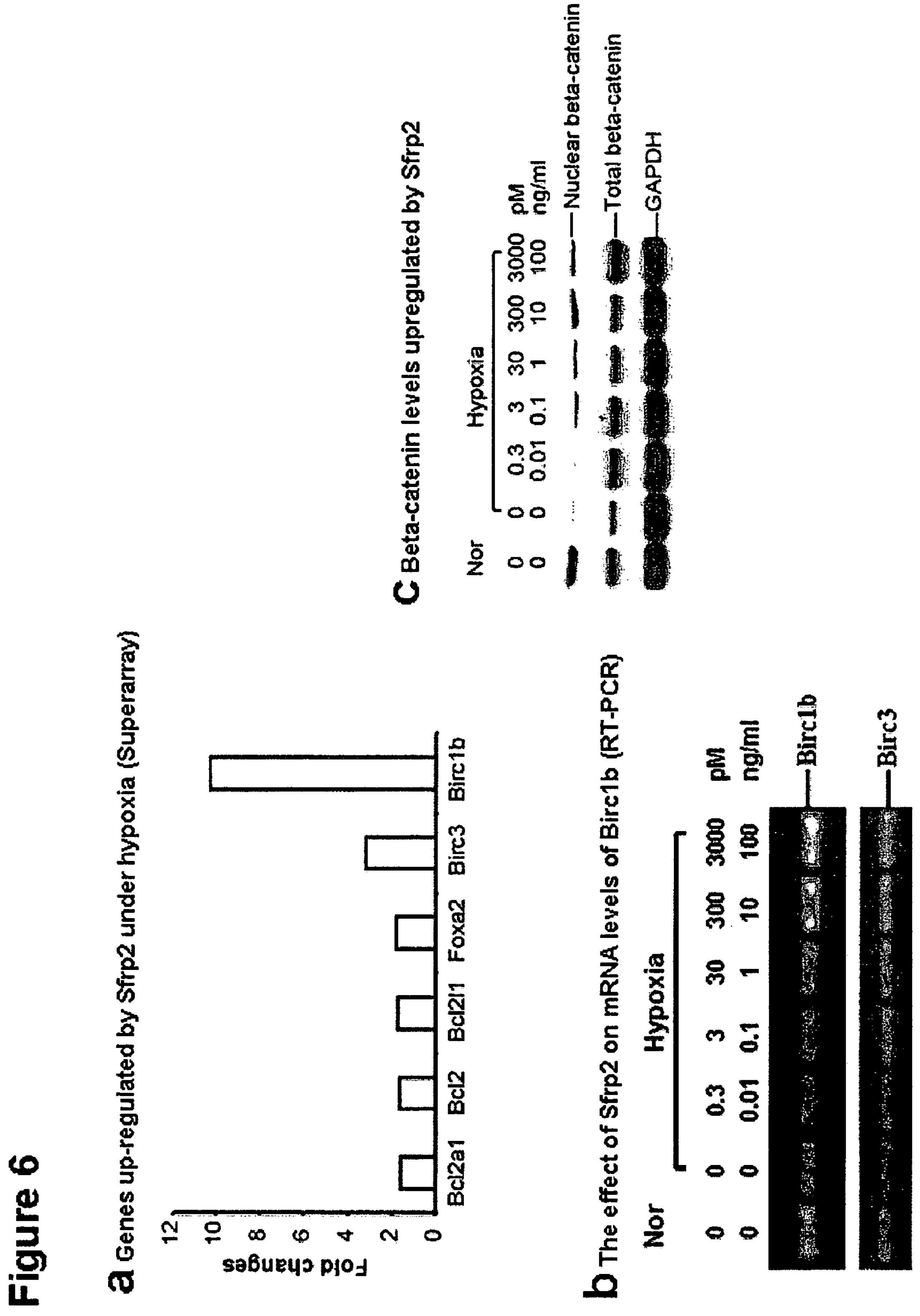
FIG. 6A is a bar graph showing genes upregulated by Sfrp2 under hypoxia. Microarray analysis demonstrates Sfrp2 mediated upregulation of Birc1b gene expression in hypoxic cardiomyocytes.
FIG. 6B is a photograph of an electrophoretic gel showing the effect of Sfrp2 on mRNA levels on Birc1b. RT-PCR confirmed increased Birc1b expression in hypoxic cardiomyocytes following Sfrp2 treatment.
FIG. 6C is a photograph of results of a Western Blot showing that beta-catenin levels are increased by Sfrp2. Western blotting for nuclear and total βcatenin expression in ARVCs demonstrates a reduction of βcatenin following hypoxia and upregulation following treatment with Sfrp2.

Sfrp2 Upregulates Expression of Anti-Apoptotic Gene Birc1b in Hypoxic Cardiomyocytes To further investigate the molecular mechanism by which Sfrp2 protects cardiomyocytes from cell death, RNA from hypoxic cardiomyocytes following Sfrp2 treatment (10 ng/mL) was collected and expression of multiple genes involved in cell survival/death pathways was determined using microarray analysis. Using an oligo GE Array for rat signal transduction pathways, gene expression of 95 marker genes associated with 18 different signaling pathways was analyzed. In this analysis, 43 genes showed differential expression between the Sfrp2 treated and the control cardiomyocytes. Sfrp2 upregulated the expression of Birc1b, an anti-apoptotic gene belonging to the neuronal apoptosis inhibitory protein (NAIP) family. Expression of other cytoprotective genes such as Bcl2 were only minimally increased in hypoxic cardiomyocytes in the presence of Sfrp2 (FIGS. 6A, B).

Sfrp-Based Therapy for Cardiac Disorders

Sfrp2 was identified as an Akt-MSC secreted protein exerting prosurvival effects on the myocardium. Several lines of evidence support the role of Sfrp2 as a principal mediator of anti apoptotic effects exerted on the myocardium by Akt-MSC. First, Sfrp2 expression is dramatically upregulated (100×) in Akt-MSC compared to GFP-MSC and its expression/secretion is dependent on the PI3 kinase/Akt pathway. Secondly, Sfrp2 conferred prosurvival effects on hypoxic cardiomyocytes. Moreover, knockdown of Sfrp2 expression resulted in the attenuation of the prosurvival action of Akt-MSC conditioned medium both in vitro and in vivo.

Sfrp2 is a secreted glycoprotein molecule that structurally resembles cell surface Frizzled receptors but lacks the latter's transmembrane domains. Sfrps compete with the frizzled receptor for Wnt ligands by direct binding of Wnts thus preventing activation of Wnt signaling in the cell. The Wnt family currently comprises 19 different proteins. Wnts are known to regulate organogenesis during embryonic development and in mammals and in other species such as amphibians and birds have been implicated in cardiac morphogenesis as well. They regulate diverse cellular processes such as proliferation, differentiation and apoptosis, but the role of the Wnts in regulating such processes in the post natal heart was not known. Although various Wnts such as Wnt10b and several frizzled receptors are expressed in the human heart, it was not known whether they play a role in cardiac homeostasis. The data described herein indicates that Sfrp2, a known modulator of Wnt signaling exerts prosurvival action on cardiomyocytes. The data demonstrate that Sfrp2 increases as well as nuclear βcatenin within the hypoxic cardiomyocyte in a dose dependent manner. βcatenin when activated translocates to the nucleus and initiates transcription of a wide variety of genes; thus the nuclear fraction represents a more accurate measure of activated βcatenin. Sfrp1 has previously been shown to potentiate Wnt signaling by directly binding to Frizzled receptors. In hypoxic cardiomyocytes, Sfrp2 binds locally present Wnts and alters the balance of intracellular Wnt signaling within a cardiomyocyte to favor a canonical pathway. Wnt3a was found to be upregulated in hypoxic cardiomyocytes. Wnt3a increases cardiomyocyte apoptosis and Sfrp2 blocks this effect of Wnt3a. Sfrp2 may also bind directly to frizzled receptor on cardiomyocytes activating the canonical pathway. The data indicate that Sfrp2 by increasing cellular and nuclear βcatenin enhances the survival response of cardiomyocytes against hypoxia induced apoptosis. Sfrp2 also upregulated expression of Birc1b, an anti-apoptotic gene belonging to the NAIP family. Sfrp2 mediated increased βcatenin activates transcription of anti-apoptotic genes such as Birc1b in hypoxic cardiomyocytes. Indeed, pharmacologic inhibition of GSK3β, resulting in increased βcatenin has been found to upregulate expression of anti-apoptotic genes such as Bcl2. Sfrp2 is involved in regulating cardiomyocyte cell survival and preserving cardiac function following myocardial infarction. Sfrp2 also plays a role as an important paracrine factor mediating beneficial effects of stem cell therapy. Sfrp2 alters the local milieu around the infarct zone to favor cardiomyocyte cell survival. Simple administration of Sfrp2 protein or fragments that modulate the Wnt-βcatenin pathway achieve results similar to stem cell based cardiac therapy, and a protein based therapy has advantages over cell based cardiac therapy for acute myocardial infarction and other ischemic cardiac disorders.

Example 3

Sfrp2 Maintains Cells in a Stem Cell State

Sfrp2 was found to be strongly expressed by mouse embryonic stem cells (e.g., P19CL6 cell line which readily differentiates into cardiomyocytes under certain conditions). Sfrp2 was found to strongly inhibit differentiation of the murine embryonic P19C16 cell line. Overexpression of Sfrp2 or addition of recombinant Sfrp2 protein inhibited differentiation of these cells. This data indicates that Sfrp2, by inhibiting differentiation of stem cells and maintaining them in the undifferentiated state, plays a role in maintenance of a stem cell phenotype and self renewal of stem cells. When added to P19CL6 cells, purified Sfrp2 prevented these cells from differentiating into cardiomyocytes. This result indicates that Sfrp2 by inhibiting differentiation of embryonic stem cells and maintaining them in the undifferentiated state preserves a stem cell phenotype of such cells. Maintenance of stemness is a fundamental and essential property of stem cells. It is not only of essential biological importance but great clinical significance. For example, bone marrow transplantation involves selection and administration of hematopoietic stem cells. A composition, e.g., Sfrp2 or other paracrine factor, that maintain the stemness of embryonic and adult stem cells is useful to preserve and maintain stem cells for tissue repair and regeneration.

Example 4

Identification of Protective Factors Secreted by Akt-MSC

Microarray analysis of Akt-MSC and control MSC under normoxia or hypoxia was performed to identify transcripts that were differentially regulated between these conditions. Using this approach, 61 proteins of know paracrine function were identified, e.g., pleiotrophin, chemokine ligands 2 and 7 and various angiogenic factors such as VEGFa, angiopoietin 4 and HGF. Upregulated transcripts with unassigned function were subjected to genomic analysis using a combination of bioinformatic software programs that allows predictions of potential secreted peptides. Putative secreted proteins thus identified were then screened using siRNA technologies in a high throughout cell-based assays to examine key physiological mechanisms involved in the cardioprotective effects of Akt-MSCs. Using this approach, secreted proteins were identified that are overexpressed in Akt-MSCs. One of these was highly expressed in Akt-MSCs but nearly undetectable in control MSCs. Permanent clones of Akt-siRNA knock down were then established for each of these genes and conditioned medium from these cells was compared to conditioned medium from Akt-MSCs for its cytoprotective effect in cardiac myocytes in vitro by apoptosis and cell viability assays.

Subsequently, the open reading frames of these novel transcripts were cloned and expressed in *E. coli* as maltose binding protein (MBP) fusion proteins. Compared with MBP alone, one of the MBP-novel fusion proteins (Protein #12; "h12") significantly reduced the $H_2O_2$-induced apoptosis in H9C2 myocytes. Protein 12 was re-cloned into pET vector to allow rapid purification as a 6×His tagged recombinant protein. Since Protein 12 is cysteine rich, purification was performed under denaturing condition and the protein was refolded by dialysis with a redox pair to promote disulfide bond formation. To test the cardioprotective effects of Protein 12, the effects of addition of this protein on $H_2O_2$-induced apoptosis in H9C2 myocytes was evaluated. Myocytes were treated with 100 μM $H_2O_2$ or vehicle and the levels of apoptosis was assessed by FACS analysis following Annexin V/PI staining. $H_2O_2$ induced high levels of early apoptosis, yielding approximately 30% Annexin V positive cells with less than 5% necrotic cells (PI positive). Pre-treatment of the cells with 10 nM of Protein 12 for 30 min reduced early apoptosis by nearly 50%. This protein significantly reduced $H_2O_2$ induced caspase 9 activity in adult rat cardiomyocytes by 38.5%, dramatically inhibited the mitochondrial release of cytochrome C and increased the total survival rate by 28%. The data indicate that this cysteine-rich Protein 12 possesses cardio-protective effects of Akt-MSCs.

A total of 5 transcripts with previously undefined function were found to account account for myocardial protection of AKT-MSCs. The open reading frame of these novel transcripts were subsequently cloned, expressed and purified from *E. coli*, as either fusion proteins of maltose binding protein-novel proteins or as 6×His tagged recombinant proteins. Protein No. 12, which is a cysteine-rich insoluble protein when expressed in *E. coli*., was then purified under denaturing condition and refolded by dialysis with a redox pair to promote disulfide bond formation. This No. 12 protein was used in various assays for oxidative stress induced apoptosis in cardiomyocytes and was found to have a strong cardio-protective effect.

For Human No. 12, the coding sequence without the predicted N-terminal signal region (1158 base pairs) were amplified and cloned in-frame of protein translation into pMal-C vector to generate a fusion protein of maltose binding protein-Human No. 12, designated as MBP-h12 (~80 KDa). Expression was induced by IPTG in *E. coli*. and purification of MBP-h12 was done by standard affinity chromatography according to New England Biolab's instructions. MBP-h12 was further purified by FPLC system. Compared with control MBP alone, this MBP-h12 fusion protein significantly prevents $H_2O_2$-induced early apoptosis in H9C2 myocytes (~30% reduction of apoptosis), by Annexin V/PI double staining with FACS analysis. To gain further insight of protein No. 12' function in cardiovascular biology, same coding region (1158 base pairs) were re-amplified and cloned in-frame into pET 15b vector to generate 6×His-tagged recombinant protein, designated as His-h12 (~40 KDa). Protein was first purified under denaturing condition and refolded by dialysis with gradually decreasing amount of dithiothreital. Oxidized and reduced of glutathione as the 'redox pair' was added in the final step to promote disulfide bond formation. Refolded His-h12 proteins were dialyzed extensively in PBS and were used in subsequent apoptosis assays.

Figure 7:
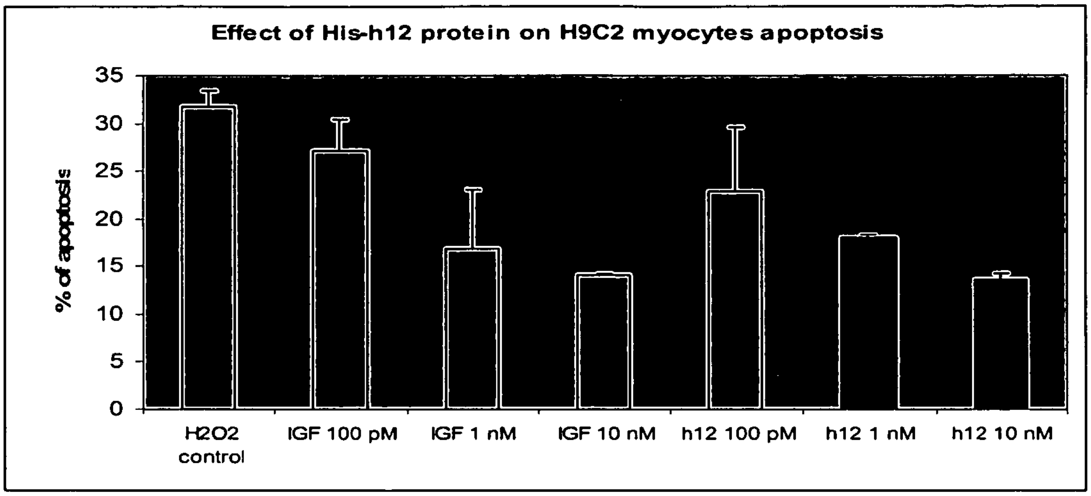
FIG. 7 is a bar graph showing the effect of cytoprotective factor h12 compared to IGF-1 on myocyte apoptosis.

FIG. 7 shows the results of Annexin V/PI staining with FACS analysis in H9C2 myocytes for early apoptosis. H9C2 myoctyes were seeded at $1\times10^4$ per well in 6-well plate one day before experiment. Recombinant His-h12 proteins were added to the cells at different concentration for 30 min first and then the cells were challenged with 100 μM of $H_2O_2$ for 2 hours to induce apoptosis. The apoptotic cells were calculated as the percentage of Annexin V positive cells in total cells in FACS analysis. Recombinant human IGF-1 proteins were used as a positive control. Pre-incubation of this His-h12 recombinant protein dramatically reduced subsequent $H_2O_2$-induced early apoptosis in H9C2 myocytes, resulting in a ~50% reduction in annexin V positive cells, P<0.001. The effect of Human No. 12 is equivalent to human recombinant IGF-1 protein at the same dose, 10 nM.

Figure 8:
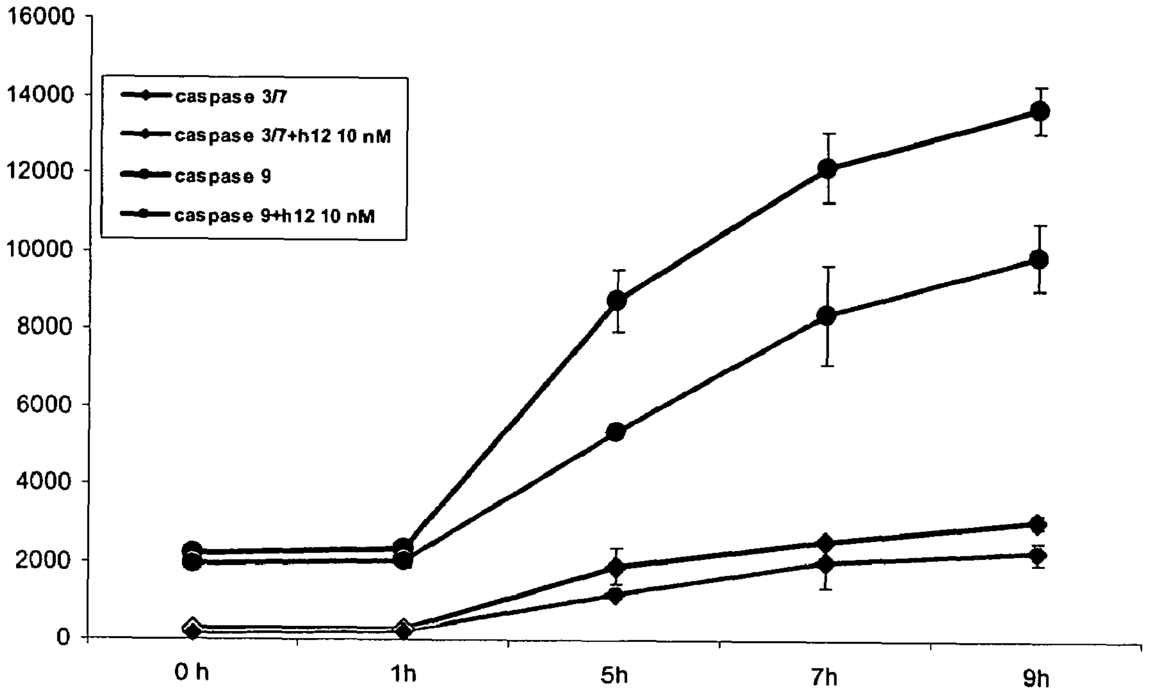
FIG. 8 is a line graph showing caspase inhibition in cardiomyocytes by h12.

An assay was carried out to evaluate caspase inhibition by recombinant His-h12 protein in adult rat cardiomyocytes (FIG. 8). Adult rat cardiomyocytes were pre-incubated with 10 nM of recombinant His-h12 protein for 30 min and then challenged with 100 μM of $H_2O_2$ for different time points. Cell lysates were used for the measurement of relative amount of active caspase with Promega's Caspase-Glo kits. His-h12 protein significantly reduced caspase 9 activity starting from 5 hours onward, reaching highest inhibition (~40% inhibition) at 9 hour, p<0.001. The absolute amount of active Caspase 3/7 is relatively lower than that of Caspase 9 in there cells, however, His-h12 protein also significantly reduced caspase 3/7 activity at 9 hours, p<0.01.

Figure 9:
FIG. 9 is a series of photographs electrophoretic gels showing that h12 phosphorylates/activates AKT in cardiomyocytes
Figure 9:
Figure 9:
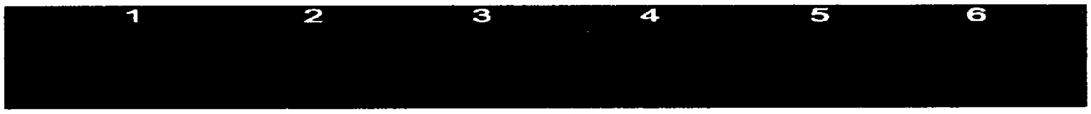
Figure 9:
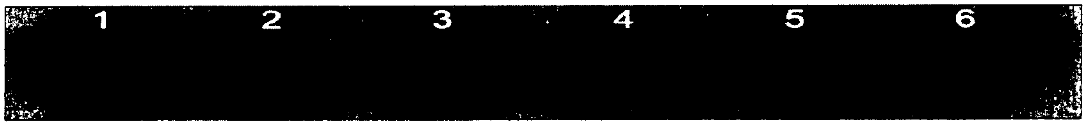

Survival signaling mechanism of His-h12 protein on cardiomyocytes was also evaluated. Experiments were carried out to determine whether His-h12 exerts its protective effect for $H_2O_2$-induced apoptosis of cardiomyocytes, in a paracrine fashion mainly through intracellular survival signaling transduction, which positively regulates the whole machinery of apoptosis network. The expression of apoptosis-related genes was studied in rat adult cardiomyocytes after incubation of His-h12 protein at 10 nM at various time points. Adult rat cardiomyocytes were incubated with recombinant His-h12 protein at 10 nM final concentration for 10 min, 30 min, 1 h, 2 h and 3 h. Whole cell lysates were separated on 10% SDS-PAGE gels and probed with phosphor-Akt antibodies, total Akt antibody and GSK-3β antibody (FIG. 9). Lane 1, vehicle PBS control treatment; Lane 2-6, 10 min, 30 min, 1 h, 2 h and 3 h incubation of cardiomyoctyes with His-h12 protein respectively. Compared with lane 1 vehicle PBS control treatment, incubation of His-h12 protein dramatically activates phosphor $Akt^{Thr308}$ at 30 min, with the concurrent phosphorylation of Akt's substrate-GSK-3β, at the same time point. No significant changes were found in total Akt and β-tublin as loading controls.

Figure 10:
FIG. 10 is a photograph showing inhibition of cytochrome C release by h12.

FIG. 10 shows the results of an assay to evaluate cytochrome C release. Adult rat cardiomycytes were pre-incubated with recombinant His-h12 protein at 10 nM for 30 min, then challenged with 100 μM of $H_2O_2$ for 6 h to induce apoptosis. Cytosolic proteins were separated by 15% SDS-PAGE gel and probed with anti-cytochrome C antibodies. Lane 1-2, vehicle PBS control treatment; Lane 3-4, $H_2O_2$ treatment of cardiomyocytes for 6 h; Lane 5-8, cardiomyoctyes pre-incubated with His-h12 protein for 30 min and then challenged with $H_2O_2$ for 6 h. Compared with Lane 1-2 controls, $H_2O_2$ treatment of Lane 3-4 resulted in a dramatic release of cytochrome C into cytosolic compartment of cardiomyocytes. However, pre-incubation of His-h12 protein with cardiomyocytes for 30 min significantly prevented the release of cytochrome C.

Figure 11:
FIG. 11 is a photograph of an electrophoretic gel showing mitochondrial Bcl-2 protein stabilization by h12.

FIG. 11 shows stabilization of mitochondrial Bcl-2 protein level by His-h12 protein during cardiomyocyte apoptosis. Adult rat cardiomycytes were pre-incubated with recombinant His-h12 protein at 10 nM for 30 min, then challenged with 100 μM of $H_2O_2$ for 6 h to induce apoptosis. Mitochondrial proteins were separated by 12.5% SDS-PAGE gel and probe with anti-Bcl-2 antibody. Lane 1, no treatment control; Lane 2, cardiomyocytes challenged with 100 μM of $H_2O_2$ for 6 h; Lane 3-6, cardiomyocytes pre-incubated with 10 nM of His-h12 for 30 min and then challenged with 100 μM of $H_2O_2$ for 6 h. Compared with Lane 1 control, $H_2O_2$ treatment of Lane 2 resulted in a modest decrease of mitochondrial Bcl-2. Pre-incubation of cardiomyocytes with His-h12 protein stabilized the mitochondrial Bcl-2 protein level.

Sequences and GenBank Accession Number of His-h12

No. 12 has a GenBank designation human BC037293. This gene product is also know as chromosome 3 open reading frame 58 (c3orf58). Mouse No. 12 homologous gene is currently unknown. The cDNA of human No. 12 clone was purchased from ATCC, coding region were amplified to make the expression construct, N-terminal signal deletion coding sequence of human No. 12 were amplified and clone into pMal-C vector for fusion protein expression and purification, which were used in the initial screening studies. Human No. 12 was further expressed as 6×His tagged recombinant protein for cardio-protection studies.

```
Human No.12 full-length mRNA sequence (h12; SEQ ID NO16)
  1 gccggagtcg gagggcgggg agctaggagg agggagctcg agagttgtgg agactagtga

 61 ctgggagaag tcgcagcccg ctcaggcccg cgccttcccg ctccccgtct tcctctctca

121 cacacctact ccgccctccg ccccagcccg cgcgctagct ccttctctcg cccggggttc

181 ctgccggtag ctctccgggt cttggcgcgg cgggggcgcc ccgggggtgc cctcgccctc

241 ccgttgcggg cgggcgggcg gtatgtggcg cctggtgccc ccgaagctgg gccgcctgtc

301 ccgctcgctg aagctggcgg cgctgggcag cctgttggtg ctgatggtgc tgcactcgcc

361 gtcgctgctc gcctcttggc agcgcaacga actgaccgac cggcgcttcc tgcagctcaa
```

-continued

```
 421 taagtgcccg gcgtgcttcg gcacgagctg gtgccgccgc ttcctcaacg ggcaggtggt
 481 attcgaggcg tggggccgct tgcgcctgct ggacttcctc aacgtgaaga acgtgtactt
 541 cgcgcagtac ggcgagcccc gcgagggcgg ccgccgccga gtggtgctca agcgcctcgg
 601 ctcgcagcgc gagctggcgc agctcgacca gagcatctgc aagcgggcca ccggccggcc
 661 ccgctgcgac ctgctgcagg ccatgccccg gaccgagttc gcgcgcctca acggcgacgt
 721 gcgtctgctc acgcccgagg cggtggaggg ctggtcggac ctggtgcact gcccctcgca
 781 gcgccttctc gaccgcctgg tgcgccgcta cgcggagacc aaggactcgg gcagcttcct
 841 gcttcgcaac ctcaaggact cggagcgcat gcagctgctg ctgaccctgg ccttcaaccc
 901 cgagccgctg gtgctacaga gttttccgtc tgatgaaggt tggccatttg caaagtatct
 961 tggagcttgt ggaagaatgg tggctgtaaa ttatgttgga gaagaactgt ggagttactt
1021 taatgcgcca tgggaaaaac gagttgacct cgcttggcaa ttaatggaaa tagcagaaca
1081 gcttacaaac aatgactttg aatttgcact ctacctcctg gacgtcagct ttgacaattt
1141 tgcagttggt cctagagatg ggaaggtaat cattgtggat gctgaaaatg ttttggttgc
1201 tgacaaaaga ttaattagac aaaataaacc tgaaaattgg gatgtatggt atgaaagcaa
1261 gtttgatgac tgtgataagg aggcttgctt atcattttca aaagaaattc tttgtgctcg
1321 tgccactgtg gaccacaatt actatgctgt ttgtcagaac ctcttatcca gacatgccac
1381 ctggcgtggc acttctggag gactccttca tgatccacca agtgaaattg ccaaagatgg
1441 ccggctcgag gccttgctgg atgagtgtgc caacccaaag aagcgctatg gcagattcca
1501 ggctgcaaaa gaactgcgtg aatacctagc acaattaagt aacaacgtga ggtagtctat
1561 ggtgaacttt tctttttttc tccatttaaa cagcactggc taaaactaaa ccaccaaaaa
1621 acgatctgaa aaaatgaaat ttggaagtgt tacattcaga ggatgataaa cttgcactga
1681 tagatcttaa tgttaacatc catcaaaata agacattact tcaaaaatca catgatgctt
1741 ctgcaaataa gtatgttctt atactttgga ggcttgagct gtcatcagct gctccccact
1801 accccggaat gcttgagtgg attaatgaat attgttaagc tattggaaat gagtctgata
1861 gtacattggc ttgtgtatca aagggtactt ggtacttagt ttgcatttac tatcatgatt
1921 ttgtgaatct cttgcattta ctttgaatgt caagtcagat tggtctgttt tataggccgc
1981 tttttccttc tgatgtgtag ggtttttttcc cccttttttt ttttaattaa attttgaaaa
2041 ttcaggttac tgtaggtgtt catttaaatt tttaatagtt gtcattcagt gctatttggt
2101 acatatttac tgttagggca ggattcccag gtttactgtg ttttttttt ttttttttta
2161 aagaaagcta aatattacat tatgtaaata cttcttttca ccaacttctg tagtttcacc
2221 attgcatggt gtcatttcag gttatttaac agttatatcc ctctatgcca ataattagaa
2281 gtgtacacta aacatgaagt ttggcatatg ttgcaaaatg tcattttatc tttctaaagg
2341 ctttaagaag aatatactag aatctatata ttgatgttaa ttttgattca gaaaaaaaat
2401 acaacccagt atctaaaaag tgttaactag tccaagatag taatgcatat gccaaagaaa
2461 tattacacct aatctcatgt ttagaattta aaatagaatt ggtcagctac ttattcttac
2521 caccctactt ccagtatttt agctctgtca ttattaaatt cagatcttcc tgattatttt
2581 ttctgttgaa agttaaacta ctgctttcaa gtaatttaaa gttatcctac cttttattca
2641 tgggtagttt tgcaaaatta acatggtagc cattgtttga atttaatcgg gcatcataac
2701 ttttcattta ttgaggaact aatcattatt actataaagc atacaaatta gccagtcagc
2761 acactttggt cttctttacc taagggttaa acatcagaac atcaaattta attatttgca
```

-continued

```
2821 tagaaatgtg tgggctcttt atataagttg actatcacta acaggtaata tttttctgtt
2881 tgaagttgtt acttttgttt acagcaaagt ttgatgtagt gtgcagtagt gagctctaga
2941 ctgatctttt tctaaatcag aaagtgatta aagtatgcac aaccaaaggc aggtttttct
3001 ttttcattta ttcagcaact atttattaag catcaactct gtgccaggca cgttactagc
3061 tgctacatac tgtctgaaca tgacatacgg ttaagtaact ttacaattat tatcaaatac
3121 ttcaatgtag atatttctta agttgaaata gcattaacta ggataatgct ttcatgttat
3181 tttattgtct tgtgatagaa attcaacttg taccatctaa aactaggttg ctataaaaat
3241 aggaggatga agtcaataaa gtttatgcca gtttaaaaac tggaaggaaa aggtaagagc
3301 tctccattat aaaatagttg cattcggtta atttttacac attagtgcat tgcgtatatc
3361 aactggccct caatgaagca tttaagtgct tggaatttta ctaaactgac tttttttgcaa
3421 ctttgggaga tttttgaggg gagtgttgaa aattgccaaa cactcacctc ttactcaaaa
3481 cttcaaataa aatacacatt ttcaagaggg agcacctttt atatttgata agttttcatt
3541 ataaacctta taataccagt cacaaagagg ttgtctgtct atggtttagc aaacatttgc
3601 ttttcttttt ggaagtgtga ttgcaattgc agaacagaaa gtgagaaaac actgccagcg
3661 gtgattgcta cttgaggtag ttttttacaa ctaccatttc ccctccatga aattatgtga
3721 aatttatttt atctttggga aaagttgaga agatagtaaa agaattagga atttaaaatt
3781 acagggaaaa atatgtaagt gaaaagcaat aaatattttg ttcactttgc tatcaagatg
3841 ttcactatca gatatttatt atatggcagc aatttatatt tttaatcatt gcccattaat
3901 agacgcagta aaatattttt gaatcagaca tttggggttt gtatgtgcat taaaattgtc
3961 ttttgtactg taagttactg ttaatttgaa tattttattg aactgtctcc ctgtgccttt
4021 ataatataaa gttgtttcta caacttttaa tgatcttaat aaagaatact ttaggaaaaa
4081 aaaaaaaaaa a
```

Human No.12 protein sequence (sequence in underlined type was used to generate recombinant His-h12 protein) (h12; SEQ ID NO: 17)

MWRLVPPKLGRLSRSLKLAALGSLLVLMVLHSPSLLASWQRNEL<u>TDRRFL</u>

<u>QLNKCPACFGTSWCRRFLNGQVVFEAWGRLRLLDFLNVKNVYFAQYGEPR</u>

<u>EGGRRRVVLKRLGSQRELAQLDQSICKRATGRPRCDLLQAMPRTEFARLN</u>

<u>GDVRLLTPEAVEGWSDLVHCPSQRLLDRLVRRYAETKDSGSFLLRNLKDS</u>

<u>ERMQLLLTLAFNPEPLVLQSFPSDEGWPFAKYLGACGRMVAVNYVGEELW</u>

-continued

<u>SYFNAPWEKRVDLAWQLMEIAEQLTNNDFEFALYLLDVSFDNFAVGPRDG</u>

<u>KVIIVDAENVLVADKRLIRQNKPENWDVWYESKFDDCDKEACLSFSKEIL</u>

<u>CARATVDHNYYAVCQNLLSRHATWRGTSGGLLHDPPSEIAKDGRLEALLD</u>

<u>ECANPKKRYGRFQAAKELREYLAQLSNNVR</u>

Other genes and gene products, the function and activity of which have previously not been known, have now been identified as having cardioprotective activity. The nucleic acid and amino acid sequences of these factors are described below.

Human No.1 mRNA sequence (h1: SEQ ID NO: 18)

```
  1 gcatcttggc agggtccggg gacgtggact atttcgcaca ccacaccacg gggagggatt
 61 tttttctatt ttccctacga aaaacagatc tttttaagga tggtgctgct ccactggtgc
121 ctgctgtggc tcctgtttcc actcagctca aggacccaga agttacccac ccgggatgag
181 gaactttttc agatgcagat ccgggacaag gcatttttttc atgattcgtc agtaattcca
241 gatggagctg aaattagcag ttatctcttt agagatacac ctaaaaggta tttctttgtg
301 gttgaagaag acaatactcc attatcagtc acagtgacgc cctgtgatgc gcctttggag
361 tggaagctga gcctccagga gctgccagag gacaggagcg gggaaggctc aggtgatctg
```

-continued

```
 421 gaacctcttg agcagcagaa gcagcagatc attaatgagg aaggcactga gttattctcc
 481 tacaaaggca atgatgttga gtattttata tcgtctagtt ccccatccgg tttgtatcag
 541 ttggatcttc tttcaacaga gaaagacaca catttcaaag tatatgccac cacaactcca
 601 gaatctgatc agccataccc tgagttaccc tatgacccaa gagtagatgt gacctcactg
 661 gggcgcacca cggtcacttt ggcctggaaa ccaagcccca ctgcctcttt gctgaaacaa
 721 cccattcagt actgtgtggt catcaacaaa gagcacaatt tcaaaagtct ctgtgcagtg
 781 gaagcaaaac tgagtgcaga tgatgctttt atgatggcac cgaaacctgg tctggacttc
 841 agcccctttg actttgccca ctttggattt ccttctgata attcaggtaa agaacgcagt
 901 ttccaggcaa agccttctcc aaaactgggg cgtcatgtct actccaggcc caaggttgat
 961 attcagaaaa tctgcatagg aaacaagaac atcttcaccg tctctgatct gaaacccgac
1021 acgcagtact actttgatgt atttgtggtc aacatcaaca gcaacatgag caccgcttat
1081 gtaggtacct ttgccaggac caaggaagaa gccaaacaga agacagtcga gctaaaagat
1141 gggaagataa cagatgtatt tgttaaaagg aagggagcaa agtttctacg gtttgctcca
1201 gtctcttctc accaaaaagt caccttcttt attcactctt gtctggatgc tgtccaaatc
1261 caagtgagaa gagatgggaa acttcttctg tctcagaatg tggaaggcat tcagcagttt
1321 cagcttagag gaaaacctaa agctaaatac ctcgttcgac tgaaaggaaa caagaaagga
1381 gcatctatgt tgaaaattct agctaccaca aggcctacta agcagtcatt tccctctctt
1441 cctgaagaca caagaatcaa agcctttgac aagctccgta cctgttcctc ggccaccgtg
1501 gcttggctag gcactcagga aaggaacaag ttttgcatct acaaaaaaga agtggatgat
1561 aactacaatg aagaccagaa gaaaagagag caaaaccaat gtctaggacc agatataagg
1621 aagaagtcag aaaaggtcct ctgtaaatat ttccacagtc aaaacttgca gaaagcagtg
1681 accacagaaa caattaaagg tcttcagcct ggcaaatctt acctgctgga tgtttatgtc
1741 ataggacatg gggggcactc tgtaaagtat cagagtaagg ttgtgaaaac tagaaagttc
1801 tgttagttac cttcttatag agatatatta tgtagaactc caggagggac attaaatcac
1861 tttaagtata aactgactac tcccacagtt gagagaagtt gtgacctgta cttgtactat
1921 ggaaggaagg atatcaacgt gtgtatattg atgtttatat aagtaactct tgaaggagac
1981 ttgttctagc gtgccccatg gtacctagtg tgtgtctgat gccggttggt gtcaaagata
2041 gagggcttct tgaaggaact tgccattcct tgctttgacc actgcatgaa ctgcttctaa
2101 attattttat tacctaaaaa tttaaaatat gccattcatt gcacacaccc acaaatgcaa
2161 atcattcctc tctatagatg ctaggatata tataaattat tttataaatt cttgttttaa
2221 atgtcagtgt ttctatgatt gtaaactatt aaattctttt cctattaaag tacagatcta
2281 atctaagtat tattaagttg atagccctct agtcagttat attgctattg taaattcttg
2341 tttgttgagt aaaatgttta aatactatat gtatctcatg tacaaagttg acatacatta
2401 tattcatgta cataaaatta aagagattag attataa
```

Human No.1 protein sequence (h1: SEQ ID NO: 19)
MVLLHWCLLWLLFPLSSRTQKLPTRDEELFQMQIRDKAFFHDSSVIPDGA

EISSYLFRDTPKRYFFVVEEDNTPLSVTVTPCDAPLEWKLSLQELPEDRS

GEGSGDLEPLEQQKQQIINEEGTELFSYKGNDVEYFISSSSPSGLYQLDL

LSTEKDTHFKVYATTTPESDQPYPELPYDPRVDVTSLGRTTVTLAWKPSP

TASLLKQPIQYCVVINKEHNFKSLCAVEAKLSADDAFMMAPKPGLDFSPF

DFAHFGFPSDNSGKERSFQAKPSPKLGRHVYSRPKVDIQKICIGNKNIFT

-continued

VSDLKPDTQYYFDVFVVNINSNMSTAYVGTFARTKEEAKQKTVELKDGKI

TDVFVKRKGAKFLRFAPVSSHQKVTFFIHSCLDAVQIQVRRDGKLLLSQN

VEGIQQFQLRGKPKAKYLVRLKGNKKGASMLKILATTRPTKQSFPSLPED

TRIKAFDKLRTCSSATVAWLGTQERNKFCIYKKEVDDNYNEDQKKREQNQ

CLGPDIRKKSEKVLCKYFHSQNLQKAVTTETIKGLQPGKSYLLDVYVIGH

GGHSVKYQSKVVKTRKFC

Human No.5 mRNA sequence (h5; SEQ ID NO: 20

1 agcgggatag cccgcggccg cgcctgcccg ctcgcacccc tctcccgcgc ccggttctcc 61 ctcgcagcac ctcgaagtgc gcccctcgcc ctcctgctcg cgccccgccg ccatggctgc 121 ctcccccgcg cggcctgctg tcctggccct gaccgggctg gcgctgctcc tgctcctgtg 181 ctggggccca ggtggcataa gtggaaataa actcaagctg atgcttcaaa aacgagaagc 241 acctgttcca actaagacta aagtggccgt tgatgagaat aaagccaaag aattccttgg 301 cagcctgaag cgccagaagc ggcagctgtg ggaccggact cggcccgagg tgcagcagtg 361 gtaccagcag tttctctaca tgggctttga cgaagcgaaa tttgaagatg acatcaccta 421 ttggcttaac agagatcgaa atggacatga atactatggc gattactacc aacgtcacta 481 tgatgaagac tctgcaattg gtccccggag cccctacggc tttaggcatg gagccagcgt 541 caactacgat gactactaac catgacttgc cacacgctgt acaagaagca aatagcgatt 601 ctcttcatgt atctcctaat gccttacact acttggtttc tgatttgctc tatttcagca 661 gatcttttct acctactttg tgtgatcaaa aaagaagagt taaaacaaca catgtaaatg 721 ccttttgata tttcatggga atgcctctca tttaaaaata gaaataaagc attttgttaa 781 aaagaaaaaa aaaaaaaaaa Human No.5 protein sequence (h5; SEQ ID NO: 21)

MAASPARPAVLALTGLALLLLLCWGPGGISGNKLKLMLQKREAPVPTKTK

-continued

VAVDENKAKEFLGSLKRQKRQLWDRTRPEVQQWYQQFLYMGFDEAKFEDD

ITYWLNRDRNGHEYYGDYYQRHYDEDSAIGPRSPYGFRHGASVNYDDY

Human No.8 mRNA sequence (h8; SEQ ID NO: 22)

```
   1 cactgggaga cagtccactt aaatgcagct ccagggttgc gaggcaccca ccagcatcat
  61 tccccatgcg aggtggcaaa tgcaacatgc tctccagttt ggggtgtcta cttctctgtg
 121 gaagtattac actagccctg ggaaatgcac agaaattgcc aaaaggtaaa aggccaaacc
 181 tcaaagtcca catcaatacc acaagtgact ccatcctctt gaagttcttg cgtccaagtc
 241 caaatgtaaa gcttgaaggt cttctcctgg gatatggcag caatgtatca ccaaaccagt
 301 acttccctct tcccgctgaa gggaaattca cagaagctat agttgatgca gagccgaaat
 361 atctgatagt tgtgcgacct gctccacctc caagtcaaaa gaagtcatgt tcaggtaaaa
 421 ctcgttctcg caaacctctg cagctggtgg ttggcactct gacaccgagc tcagtcttcc
 481 tgtcctgggg tttcctcatc aacccacacc atgactggac attgccaagt cactgtccca
 541 atgacagatt ttatacaatt cgctatcgag aaaaggataa agaaaagaag tggattttc
 601 aaatctgtcc agccactgaa acaattgtgg aaaacctaaa gcccaacaca gtttatgaat
 661 ttggagtgaa agacaatgtg gaaggtggaa tttggagtaa gattttcaat cacaagactg
 721 ttgttggaag taaaaaagta aatgggaaaa tccaaagtac ctatgaccaa gaccacacag
 781 tgccagcata tgtcccaagg aaactaatcc caataacaat catcaagcaa gtgattcaga
 841 atgttactca caaggattca gctaaatccc cagaaaaagc tccactggga ggagtgatac
 901 tagtccacct tattattcca ggtcttaatg aaactactgt aaaacttcct gcatccctaa
 961 tgtttgagat ttcagatgca ctcaagacac aattagctaa gaatgaaacc ttggcattac
1021 ctgccgaatc taaaacacca gaggttgaaa aaatctcagc acgacccaca acagtgactc
1081 ctgaaacagt tccaagaagc actaaaccca ctacgtctag tgcattagat gtttcagaaa
1141 caacactggc ttcaagtgaa aagccatgga ttgtgcctac agctaaaata tctgaagatt
1201 ccaaagttct gcagcctcaa actgcaactt atgatgtttt ctcaagccct acaacatcag
1261 atgagcctga gatatcagat tcctacacag caacaagtga tcgtattctg gattctatcc
1321 cacctaaaac ttctagaact cttgaacagc caagggcaac actggctcca agtgaaacac
1381 catttgttcc tcaaaaactg gaaatcttta ccagtccaga aatgcagcct acgacacctg
1441 ctccccagca aactacatct atcccttcta cacctaaacg acgcccccgg cccaaaccgc
1501 caagaaccaa acctgaaaga accacaagtg ccggaacaat tacacctaaa atttctaaaa
1561 gccctgaacc tacatggaca acaccggctc ccggtaaaac acaatttatt tctctgaaac
1621 ctaaaatccc tctcagccca gaagtgacac acaccaaacc tgctcccaag cagacaccac
1681 gtgctcctcc taagccaaaa acatcaccac gcccaagaat cccacaaaca caaccagttc
1741 ctaaggtgcc ccagcgtgtt actgcaaaac caaaaacgtc accaagtcca gaagtgtcat
1801 acaccacacc tgctccaaaa gatgtgctcc ttcctcataa accataccct gaggtctctc
1861 agagcgaacc tgctcctcta gagacacgag gcatcccttt tatacccatg atttccccaa
1921 gtcctagtca agaggaacta cagaccactc tggaagaaac agaccaatcc acccaagaac
1981 ctttcacaac taagattcca cgaacaactg aactagcaaa gacaactcag gcgccacaca
2041 gattttatac tactgtgagg cccagaacat ctgacaagcc acacatcaga cctggggtca
2101 agcaagcacc caggccatca ggtgctgata gaaatgtatc agtggactct acccacccca
```

-continued

```
2161 ctaaaaagcc agggactcgc cgcccaccct tgccacccag acctacacac ccacgaagaa
2221 aacctttacc accaaataat gtcactggaa agccaggaag tgcaggaatc atttcatcag
2281 gcccaataac tacaccaccc ctgaggtcaa cacccaggcc tactggaact ccccttggaga
2341 gaatagagac agatataaag caaccaacag ttcctgcctc tggagaagaa ctggaaaata
2401 taactgactt tagctcaagc ccaacaagag aaactgatcc tcttgggaag ccaagattca
2461 aaggacctca tgtgcgatac atccaaaagc ctgacaacag tccctgctcc attactgact
2521 ctgtcaaacg gttccccaaa gaggaggcca cagaggggaa tgccaccagc ccaccacaga
2581 acccacccac caacctcact gtggtcaccg tggaagggtg cccctcattt gtcatcttgg
2641 actgggaaaa gccactaaat gacactgtca ctgaatatga agttatatcc agagaaaatg
2701 ggtcattcag tgggaagaac aagtccattc aaatgacaaa tcagacattt tccacagtag
2761 aaaatctgaa accaaacacg agttatgaat tccaggtgaa acccaaaaac ccgcttggtg
2821 aaggcccggt cagcaacaca gtggcattca gtactgaatc agcggaccca agagtgagtg
2881 agccagtttc tgcaggaaga gatgccatct ggactgaaag acccctttaat tcagactctt
2941 actcagagtg taagggcaaa caatatgtca aaaggacatg gtataaaaaa tttgtaggag
3001 tgcagctgtg caactctctc agatacaaga tttacttgag cgactccctc acaggaaaat
3061 tttataacat aggtgatcag aggggccatg gagaagatca ctgccagttt gtggattcat
3121 ttttagatgg acgcactggg cagcaactca cttctgacca gttaccaatc aaagaaggtt
3181 atttcagagc agttcgccag gaacctgtcc aatttggaga aataggtggt cacacccaaa
3241 tcaattatgt tcagtggtat gaatgtggga ctacaattcc tggaaaatgg tagatgctgc
3301 acaaagttac cttctgtttc atcattgcaa acaaaaatca ttgaaaatac tatgccgcat
3361 tcatttaaag ctattttgtt tactatgtat aaaagtctac aatctaatta atagcaatac
3421 tagatgttta ttattagaaa agattgctga gagtatttat caggttttac aaagtcattt
3481 taagaaagca agatactgat gttaacagaa taacattttt ggggaagctg gctccctatt
3541 catggtattt taagagatca tttgtatatt atttatcaca ctgttgtaat gatgttttga
3601 gatactttta taacaaaatt aacatcaaaa aggtatatac tttttaaaaa aaatttactt
3661 ttattgatgt gtactcttcc tattgatgag ttaattccat aaatctctac ttagtttaac
3721 ttattggatc aaattatctt cagcatgtat atctggggaa aaaaggtccg aattttcaca
3781 tttatattta aacttcaatt ttttatattt aaacttcaat tttttagcaa cagctgaata
3841 gctttgcgga ggagtttaat agttacacat tcatgctaat atacatttcc tttaaacatc
3901 cacaaattct taaaaagatt gaatcagtaa atttcatttc agctaaaaat ggagtctaat
3961 atattgtttc aaaagataca tttttaccca ccataaatgt tacaatatct gaatatgctt
4021 tgtcaaacta tccctttatg caatcgtctt catattgttt ttatgattct aatcaagctg
4081 tatgtagaga ctgaatgtga agtcaagtct gagcacaaaa agataatgca caatgagatt
4141 gcctaccatt ttataggata tttactatgt atttatacgt taagacctct atgaatgaat
4201 gtatcagaga atgtctttgt aactaactgt ttaattcaat ctgtaataaa aatctaacta
4261 actaactcat ttatttctat taaaaaggta ttgtccttta ggcggggaat gggaatcctt
4321 gctgcactgt tgcagtcatt ctgaaaggac ctttccctgt acttaccttt caacatgctt
4381 caatcttatc aacgctacat tttgtatttt tcaaacaggt ataaattctg caataaagag
4441 atgtagtttt tttttaaaaa aaaaaaaaaa aaaaaaaaaa aaaaaaaaaa aaaaaaaaaa
4501 aaaaaaaaaa aaaaaaaaaa aaaaaaaaaa aaa
```

Human No.8 protein sequence (h8; SEQ ID NO: 23)

MRGGKCNMLSSLGCLLLCGSITLALGNAQKLPKGKRPNLKVHINTTSDSI

LLKFLRPSPNVKLEGLLLGYGSNVSPNQYFPLPAEGKFTEAIVDAEPKYL

IVVRPAPPPSQKKSCSGKTRSRKPLQLVVGTLTPSSVFLSWGFLINPHHD

WTLPSHCPNDRFYTIRYREKDKEKKWIFQICPATETIVENLKPNTVYEFG

VKDNVEGGIWSKIFNHKTVVGSKKVNGKIQSTYDQDHTVPAYVPRKLIPI

TIIKQVIQNVTHKDSAKSPEKAPLGGVILVHLIIPGLNETTVKLPASLMF

EISDALKTQLAKNETLALPAESKTPEVEKISARPTTVTPETVPRSTKPTT

SSALDVSETTLASSEKPWIVPTAKISEDSKVLQPQTATYDVFSSPTTSDE

PEISDSYTATSDRILDSIPPKTSRTLEQPRATLAPSETPFVPQKLEIFTS

PEMQPTTPAPQQTTSIPSTPKRRPRPKPPRTKPERTTSAGTITPKISKSP

EPTWTTPAPGKTQFISLKPKIPLSPEVTHTKPAPKQTPRAPPKPKTSPRP

RIPQTQPVPKVPQRVTAKPKTSPSPEVSYTTPAPKDVLLPHKPYPEVSQS

-continued

EPAPLETRGIPFIPMISPSPSQEELQTTLEETDQSTQEPFTTKIPRTTEL

AKTTQAPHRFYTTVRPRTSDKPHIRPGVKQAPRPSGADRNVSVDSTHPTK

KPGTRRPPLPPRPTHPRRKPLPPNNVTGKPGSAGIISSGPITTPPLRSTP

RPTGTPLERIETDIKQPTVPASGEELENITDFSSSPTRETDPLGKPRFKG

PHVRYIQKPDNSPCSITDSVKRFPKEEATEGNATSPPQNPPTNLTVVTVE

GCPSFVILDWEKPLNDTVTEYEVISRENGSFSGKNKSIQMTNQTFSTVEN

LKPNTSYEFQVKPKNPLGEGPVSNTVAFSTESADPRVSEPVSAGRDAIWT

ERPFNSDSYSECKGKQYVKRTWYKKFVGVQLCNSLRYKIYLSDSLTGKFY

NIGDQRGHGEDHCQFVDSFLDGRTGQQLTSDQLPIKEGYFRARQEPVQFG

EIGGHTQINYVQWYECGTTIPGKW

Human No.13 mRNA sequence (h13; SEQ ID NO: 24)

1 ctccggtgag ttttgtggcg ggaagcttct gcgctggtgc ttagtaaccg actttcctcc 61 ggactcctgc acgacctgct cctacagccg gcgatccact cccggctgtt cccccggagg 121 gtccagaggc ctttcagaag gagaaggcag ctctgtttct ctgcagagga gtagggtcct 181 ttcagccatg aagcatgtgt tgaacctcta cctgttaggt gtggtactga ccctactctc 241 catcttcgtt agagtgatgg agtccctaga gggcttacta gagagcccat cgcctgggac 301 ctcctggacc accagaagcc aactagccaa cacagagccc accaagggcc ttccagacca 361 tccatccaga agcatgtgat aagacctcct tccatactgg ccatattttg gaacactgac 421 ctagacatgt ccagatggga gtcccattcc tagcagacaa gctgagcacc gttgtaacca 481 gagaactatt actaggcctt gaagaacctg tctaactgga tgctcattgc ctgggcaagg 541 cctgtttagg ccggttgcgg tggctcatgc ctgtaatcct agcactttgg gaggctgagg 601 tgggtggatc acctgaggtc aggagttcga gaccagcctc gccaacatgg cgaaacccca 661 tctctactaa aaatacaaaa gttagctggg tgtggtggca gaggcctgta atcccagctc 721 cttgggaggc tgaggcggga gaattgcttg aacccgggga cggaggttgc agtgagccga 781 gatcgcactg ctgtacccag cctgggccac agtgcaagac tccatctcaa aaaaaaaaaa 841 aaaaaaaaaa aaaaaaaaa Human No.13 protein sequence (h13; SEQ ID NO: 25)
MKHVLNLYLLGVVLTLLSIFVRVMESLEGLLESPSPGTSWTTRSQLANTE

PTKGLPDHPSRSM

Other Embodiments

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. The choice of nucleic acid starting material, clone of interest, or library type is believed to be a matter of routine for a person of ordinary skill in the art with knowledge of the embodiments described herein.

Other aspects, advantages, and modifications considered to be within the scope of the following claims.

What is claimed is:

1. A method of reducing cardiac infarct size after myocardial infarction comprising contacting cardiac tissue with a full-length or mature Secreted Frizzled Related Protein 2 (Sfpr2) polypeptide, wherein cardiac infarct size is reduced following contact of said tissue with said polypeptide.

2. The method of claim 1, wherein said full-length Sfpr2 polypeptide comprises the amino acid sequence of SEQ ID NO: 7 and said mature Sfrp2 polypeptide comprises the mature amino acid sequence of SEQ ID NO: 7.

3. The method of claim 1, wherein said full-length or mature Sfrp2 polypeptide is encoded by the nucleotide sequence of SEQ ID NO: 6.

4. A method of reducing cardiac infarct size after myocardial infarction comprising contacting cardiac tissue with a Secreted Frizzled Related Protein 2 (Sfpr2) polypeptide fragment wherein said fragment binds to Wnt3a and wherein cardiac infarct size is reduced following contact of said tissue with said fragment.

* * * * *

SEQUENCE LISTING

<160> NUMBER OF SEQ ID NOS: 25

<210> SEQ ID NO 1
<211> LENGTH: 2610
<212> TYPE: DNA
<213> ORGANISM: Homo sapiens

<400> SEQUENCE: 1

```
atcctgggac agggcacagg gccatctgtc accaggggct tagggaaggc cgagccagcc     60
tgggtcaaag aagtcaaagg ggctgcctgg aggaggcagc ctgtcagctg gtgcatcaga    120
ggctgtggcc aggccagctg ggctcgggga gcgccagcct gagaggagcg cgtgagcgtc    180
gcgggagcct cgggcaccat gagcgacgtg gctattgtga aggagggttg gctgcacaaa    240
cgaggggagt acatcaagac ctggcggcca cgctacttcc tcctcaagaa tgatggcacc    300
ttcattggct acaaggagcg gccgcaggat gtggaccaac gtgaggctcc cctcaacaac    360
ttctctgtgg cgcagtgcca gctgatgaag acggagcggc cccggcccaa caccttcatc    420
atccgctgcc tgcagtggac cactgtcatc gaacgcacct tccatgtgga gactcctgag    480
gagcgggagg agtggacaac cgccatccag actgtggctg acggcctcaa gaagcaggag    540
gaggaggaga tggacttccg gtcgggctca cccagtgaca actcaggggc tgaagagatg    600
gaggtgtccc tggccaagcc caagcaccgc gtgaccatga acgagtttga gtacctgaag    660
ctgctgggca agggcacttt cggcaaggtg atcctggtga aggagaaggc cacaggccgc    720
tactacgcca tgaagatcct caagaaggaa gtcatcgtgg ccaaggacga ggtggcccac    780
acactcaccg agaaccgcgt cctgcagaac tccaggcacc ccttcctcac agccctgaag    840
tactctttcc agacccacga ccgcctctgc tttgtcatgg agtacgccaa cgggggcgag    900
ctgttcttcc acctgtcccg ggaacgtgtg ttctccgagg accgggcccg cttctatggc    960
gctgagattg tgtcagccct ggactacctg cactcggaga agaacgtggt gtaccgggac   1020
ctcaagctgg agaacctcat gctggacaag gacgggcaca ttaagatcac agacttcggg   1080
ctgtgcaagg aggggatcaa ggacggtgcc accatgaaga ccttttgcgg cacacctgag   1140
tacctggccc ccgaggtgct ggaggacaat gactacggcc gtgcagtgga ctggtggggg   1200
ctgggcgtgg tcatgtacga gatgatgtgc ggtcgcctgc ccttctacaa ccaggaccat   1260
gagaagcttt ttgagctcat cctcatggag gagatccgct tcccgcgcac gcttggtccc   1320
gaggccaagt ccttgctttc agggctgctc aagaaggacc ccaagcagag gcttggcggg   1380
ggctccgagg acgccaagga gatcatgcag catcgcttct ttgccggtat cgtgtggcag   1440
cacgtgtacg agaagaagct cagcccaccc ttcaagcccc aggtcacgtc ggagactgac   1500
accaggtatt ttgatgagga gttcacggcc cagatgatca ccatcacacc acctgaccaa   1560
```

-continued gatgacagca tggagtgtgt ggacagcgag cgcaggcccc acttccccca gttctcctac 1620
tcggccagca gcacggcctg aggcggcggt ggactgcgct ggacgatagc ttggagggat 1680
ggagaggcgg cctcgtgcca tgatctgtat ttaatggttt ttatttctcg ggtgcatttg 1740
agagaagcca cgctgtcctc tcgagcccag atggaaagac gtttttgtgc tgtgggcagc 1800
accctccccc gcagcggggt agggaagaaa actatcctgc gggttttaat ttatttcatc 1860
cagtttgttc tccgggtgtg gcctcagccc tcagaacaat ccgattcacg tagggaaatg 1920
ttaaggactt ctacagctat gcgcaatgtg gcattggggg gccgggcagg tcctgcccat 1980
gtgtcccctc actctgtcag ccagccgccc tgggctgtct gtcaccagct atctgtcatc 2040
tctctggggc cctgggcctc agttcaacct ggtggcacca gatgcaacct cactatggta 2100
tgctggccag caccctctcc tgggggtggc aggcacacag cagcccccca gcactaaggc 2160
cgtgtctctg aggacgtcat cggaggctgg gcccctggga tgggaccagg gatgggggat 2220
gggccagggt ttacccagtg ggacagagga gcaaggttta aatttgttat tgtgtattat 2280
gttgttcaaa tgcattttgg gggtttttaa tctttgtgac aggaaagccc tccccccttcc 2340 ccttctgtgt cacagttctt ggtgactgtc ccaccggagc ctccccctca gatgatctct 2400
ccacggtagc acttgacctt ttcgacgctt aacctttccg ctgtcgcccc aggccctccc 2460
tgactccctg tgggggtggc catccctggg cccctccacg cctcctggcc agacgctgcc 2520
gctgccgctg caccacggcg tttttttaca acattcaact ttagtatttt tactattata 2580
atataatatg gaaccttccc tccaaattct 2610

<210> SEQ ID NO 2
<211> LENGTH: 1715
<212> TYPE: DNA
<213> ORGANISM: Homo sapiens

<400> SEQUENCE: 2
gaattccagc ggcggcgccg ttgccgctgc cgggaaacac aaggaaaggg aaccagcgca 60
gcgtggcgat gggcgggggt agagccccgc cggagaggct gggcggctgc cggtgacaga 120
ctgtgccctg tccacggtgc ctcctgcatg tcctgctgcc ctgagctgtc ccgagctagg 180
tgacagcgta ccacgctgcc accatgaatg aggtgtctgt catcaaagaa ggctggctcc 240
acaagcgtgg tgaatacatc aagacctgga ggccacggta cttcctgctg aagagcgacg 300
gctccttcat tgggtacaag gagaggcccg aggcccctga tcagactcta cccccccttaa 360 acaacttctc cgtagcagaa tgccagctga tgaagaccga gaggccgcga cccaacacct 420
ttgtcatacg ctgcctgcag tggaccacag tcatcgagag gaccttccac gtggattctc 480
cagacgagag ggaggagtgg atgcgggcca tccagatggt cgccaacagc ctcaagcagc 540
gggccccagg cgaggacccc atggactaca agtgtggctc cccccagtgac tcctccacga 600 ctgaggagat ggaagtggcg gtcagcaagg cacgggctaa agtgaccatg aatgacttcg 660
actatctcaa actccttggc aagggaacct ttggcaaagt catcctggtg cgggagaagg 720
ccactggccg ctactacgcc atgaagatcc tgcgaaagga agtcatcatt gccaaggatg 780
aagtcgctca cacagtcacc gagagccggg tcctccagaa caccaggcac ccgttcctca 840
ctgcgctgaa gtatgccttc cagacccacg accgcctgtg ctttgtgatg gagtatgcca 900
acgggggtga gctgttcttc cacctgtccc gggagcgtgt cttcacagag gagcgggccc 960
ggttttatgg tgcagagatt gtctcggctc ttgagtactt gcactcgcgg gacgtggtat 1020

-continued

```
accgcgacat caagctggaa aacctcatgc tggacaaaga tggccacatc aagatcactg   1080

actttggcct ctgcaaagag ggcatcagtg acggggccac catgaaaacc ttctgtggga   1140

ccccggagta cctggcgcct gaggtgctgg aggacaatga ctatggccgg gccgtggact   1200

ggtgggggct gggtgtggtc atgtacgaga tgatgtgcgg ccgcctgccc ttctacaacc   1260

aggaccacga gcgcctcttc gagctcatcc tcatggaaga gatccgcttc ccgcgcacgc   1320

tcagccccga ggccaagtcc ctgcttgctg ggctgcttaa gaaggacccc aagcagaggc   1380

ttggtggggg gcccagcgat gccaaggagg tcatggagca caggttcttc ctcagcatca   1440

actggcagga cgtggtccag aagaagctcc tgccaccctt caaacctcag gtcacgtccg   1500

aggtcgacac aaggtacttc gatgatgaat ttaccgccca gtccatcaca atcacacccc   1560

ctgaccgcta tgacagcctg ggcttactgg agctggacca gcggacccac ttcccccagt   1620

tctcctactc ggccagcatc cgcgagtgag cagtctgccc acgcagagga cgcacgctcg   1680

ctgccatcac cgctgggtgg ttttttaccc ctgcc                              1715
```

```
<210> SEQ ID NO 3
<211> LENGTH: 1547
<212> TYPE: DNA
<213> ORGANISM: Homo sapiens

<400> SEQUENCE: 3

gggagtcatc atgagcgatg ttaccattgt gaaagaaggt tgggttcaga agaggggaga     60

atatataaaa aactggaggc caagatactt ccttttgaag acagatggct cattcatagg    120

atataaagag aaacctcaag atgtggattt accttatccc ctcaacaact tttcagtggc    180

aaaatgccag ttaatgaaaa cagaacgacc aaagccaaac acatttataa tcagatgtct    240

ccagtggact actgttatag agagaacatt tcatgtagat actccagagg aaagggaaga    300

atggacagaa gctatccagg ctgtagcaga cagactgcag aggcaagaag aggagagaat    360

gaattgtagt ccaacttcac aaattgataa tataggagag gaagagatgg atgcctctac    420

aacccatcat aaaagaaaga caatgaatga ttttgactat ttgaaactac taggtaaagg    480

cacttttggg aaagttattt tggttcgaga gaaggcaagt ggaaaatact atgctatgaa    540

gattctgaag aaagaagtca ttattgcaaa ggatgaagtg gcacacactc taactgaaag    600

cagagtatta aagaacacta gacatccctt tttaacatcc ttgaaatatt ccttccagac    660

aaaagaccgt ttgtgttttg tgatggaata tgttaatggg ggcgagctgt tttccattt    720

gtcgagagag cgggtgttct ctgaggaccg cacacgtttc tatggtgcag aaattgtctc    780

tgccttggac tatctacatt ccggaaagat tgtgtaccgt gatctcaagt tggagaatct    840

aatgctggac aaagatggcc acataaaaat tacagatttt ggactttgca aagaagggat    900

cacagatgca gccaccatga agacattctg tggcactcca gaatatctgg caccagaggt    960

gttagaagat aatgactatg gccgagcagt agactggtgg ggcctagggg ttgtcatgta   1020

tgaaatgatg tgtgggaggt tacctttcta caaccaggac catgagaaac tttttgaatt   1080

aatattaatg gaagacatta aatttcctcg aacactctct tcagatgcaa aatcattgct   1140

ttcagggctc ttgataaagg atccaaataa acgccttggt ggaggaccag atgatgcaaa   1200

agaaattatg agacacagtt tcttctctgg agtaaactgg caagatgtat atgataaaaa   1260

gcttgtacct ccttttaaac ctcaagtaac atctgagaca gatactagat attttgatga   1320

agaatttaca gctcagacta ttacaataac accacctgaa aaatatgatg aggatggtat   1380

ggactgcatg gacaatgaga ggcggccgca tttccctcaa ttttcctact ctgcaagtgg   1440
```

-continued acgagaataa gtctctttca ttctgctact tcactgtcat cttcaattta ttactgaaaa 1500
tgattcctgg acatcaccag tcctagctct tacacatagc aggggca 1547

<210> SEQ ID NO 4
<211> LENGTH: 4465
<212> TYPE: DNA
<213> ORGANISM: Homo sapiens

<400> SEQUENCE: 4
cctgcagcct ccggagtcag tgccgcgcgc ccgccgcccc gcgccttcct gctcgccgca 60
cctccgggag ccggggcgca cccagcccgc agcgccgcct ccccgcccgc gccgcctccg 120
accgcaggcc gagggccgcc actggccggg gggaccgggc agcagcttgc ggccgcggag 180
ccgggcaacg ctggggactg cgccttttgt ccccggaggt ccctggaagt ttgcggcagg 240
acgcgcgcgg ggaggcggcg gaggcagccc cgacgtcgcg gagaacaggg cgcagagccg 300
gcatgggcat cgggcgcagc gaggggggcc gccgcggggc agccctgggc gtgctgctgg 360
cgctgggcgc ggcgcttctg gccgtgggct cggccagcga gtacgactac gtgagcttcc 420
agtcggacat cggcccgtac cagagcgggc gcttctacac caagccacct cagtgcgtgg 480
acatccccgc ggacctgcgg ctgtgccaca acgtgggcta caagaagatg gtgctgccca 540
acctgctgga gcacgagacc atggcggagg tgaagcagca ggccagcagc tgggtgcccc 600
tgctcaacaa gaactgccac gccggcaccc aggtcttcct ctgctcgctc ttcgcgcccg 660
tctgcctgga ccggcccatc tacccgtgtc gctggctctg cgaggccgtg cgcgactcgt 720
gcgagccggt catgcagttc ttcggcttct actggcccga gatgcttaag tgtgacaagt 780
tccccgaggg ggacgtctgc atcgccatga cgccgcccaa tgccaccgaa gcctccaagc 840
cccaaggcac aacggtgtgt cctccctgtg acaacgagtt gaaatctgag gccatcattg 900
aacatctctg tgccagcgag tttgcactga ggatgaaaat aaaagaagtg aaaaaagaaa 960
atggcgacaa gaagattgtc cccaagaaga agaagcccct gaagttgggg cccatcaaga 1020
agaaggacct gaagaagctt gtgctgtacc tgaagaatgg ggctgactgt ccctgccacc 1080
agctggacaa cctcagccac cacttcctca tcatgggccg caaggtgaag agccagtact 1140
tgctgacggc catccacaag tgggacaaga aaaacaagga gttcaaaaac ttcatgaaga 1200
aaatgaaaaa ccatgagtgc cccacctttc agtccgtgtt taagtgattc tcccgggggc 1260
agggtgggga gggagcctcg ggtggggtgg gagcgggggg gacagtgccc cgggaacccg 1320
gtgggtcaca cacacgcact gcgcctgtca gtagtggaca ttgtaatcca gtcggcttgt 1380
tcttgcagca ttcccgctcc cttccctcca tagccacgct ccaaacccca gggtagccat 1440
ggccgggtaa agcaagggcc atttagatta ggaaggtttt taagatccgc aatgtggagc 1500
agcagccact gcacaggagg aggtgacaaa ccatttccaa cagcaacaca gccactaaaa 1560
cacaaaaagg gggattgggc ggaaagtgag agccagcagc aaaaactaca ttttgcaact 1620
tgttggtgtg gatctattgg ctgatctatg cctttcaact agaaaattct aatgattggc 1680
aagtcacgtt gttttcaggt ccagagtagt ttctttctgt ctgctttaaa tggaaacaga 1740
ctcataccac acttacaatt aaggtcaagc ccagaaagtg ataagtgcag ggaggaaaag 1800
tgcaagtcca ttatgtaata gtgacagcaa agggaccagg ggagaggcat tgccttctct 1860
gcccacagtc tttccgtgtg attgtctttg aatctgaatc agccagtctc agatgcccca 1920
aagtttcggt tcctatgagc ccggggcatg atctgatccc caagacatgt ggaggggcag 1980

-continued

```
cctgtgcctg cctttgtgtc agaaaaagga aaccacagtg agcctgagag agacggcgat   2040
tttcgggctg agaaggcagt agttttcaaa acacatagtt aaaaaagaaa caaatgaaaa   2100
aaattttaga acagtccagc aaattgctag tcagggtgaa ttgtgaaatt gggtgaagag   2160
cttaggattc taatctcatg tttttccttt ttcacatttt taaaagaaca atgacaaaca   2220
cccacttatt tttcaaggtt ttaaaacagt ctacattgag catttgaaag gtgtgctaga   2280
acaaggtctc ctgatccgtc cgaggctgct tcccagagga gcagctctcc ccaggcattt   2340
gccaagggag gcggatttcc ctggtagtgt agctgtgtgg ctttccttcc tgaagagtcc   2400
gtggttgccc tagaacctaa cacccctag caaaactcac agagctttcc gtttttttct   2460
ttcctgtaaa gaaacatttc ctttgaactt gattgcctat ggatcaaaga aattcagaac   2520
agcctgcctg tccccccgca ctttttacat atatttgttt catttctgca gatggaaagt   2580
tgacatgggt ggggtgtccc catccagcga gagagtttca aaagcaaaac atctctgcag   2640
tttttcccaa gtaccctgag atacttccca aagcccttat gtttaatcag cgatgtatat   2700
aagccagttc acttagacaa ctttaccctt cttgtccaat gtacaggaag tagttctaaa   2760
aaaaatgcat attaatttct tcccccaaag ccggattctt aattctctgc aacactttga   2820
ggacatttat gattgtccct ctgggccaat gcttataccc agtgaggatg ctgcagtgag   2880
gctgtaaagt ggcccctgc ggccctagcc tgacccggag gaaaggatgg tagattctgt   2940
taactcttga agactccagt atgaaaatca gcatgcccgc ctagttacct accggagagt   3000
tatcctgata aattaacctc tcacagttag tgatcctgtc cttttaacac ctttttgtg   3060
gggttctctc tgacctttca tcgtaaagtg ctggggacct taagtgattt gcctgtaatt   3120
ttggatgatt aaaaaatgtg tatatatatt agctaattag aaatattcta cttctctgtt   3180
gtcaaactga aattcagagc aagttcctga gtgcgtggat ctgggtctta gttctggttg   3240
attcactcaa gagttcagtg ctcatacgta tctgctcatt ttgacaaagt gcctcatgca   3300
accgggccct ctctctgcgg cagagtcctt agtggagggg tttacctgga acattagtag   3360
ttaccacaga atacggaaga gcaggtgact gtgctgtgca gctctctaaa tgggaattct   3420
caggtaggaa gcaacagctt cagaaagagc tcaaaataaa ttggaaatgt gaatcgcagc   3480
tgtgggtttt accaccgtct gtctcagagt cccaggacct tgagtgtcat tagttacttt   3540
attgaaggtt ttagacccat agcagctttg tctctgtcac atcagcaatt tcagaaccaa   3600
aagggaggct ctctgtaggc acagagctgc actatcacga gcctttgttt ttctccacaa   3660
agtatctaac aaaaccaatg tgcagactga ttggcctggt cattggtctc cgagagagga   3720
ggtttgcctg tgatttccta attatcgcta gggccaaggt gggatttgta aagctttaca   3780
ataatcattc tggatagagt cctgggaggt ccttggcaga actcagttaa atctttgaag   3840
aatatttgta gttatcttag aagatagcat gggaggtgag gattccaaaa acattttatt   3900
tttaaaatat cctgtgtaac acttggctct tggtacctgt gggttagcat caagttctcc   3960
ccagggtaga attcaatcag agctccagtt tgcatttgga tgtgtaaatt acagtaatcc   4020
catttcccaa acctaaaatc tgtttttctc atcagactct gagtaactgg ttgctgtgtc   4080
ataacttcat agatgcagga ggctcaggtg atctgtttga ggagagcacc ctaggcagcc   4140
tgcagggaat aacatactgg ccgttctgac ctgttgccag cagatacaca ggacatggat   4200
gaaattcccg tttcctctag tttcttcctg tagtactcct cttttagatc ctaagtctct   4260
tacaaaagct ttgaatactg tgaaaatgtt ttacattcca tttcatttgt gttgtttttt   4320
taactgcatt ttaccagatg ttttgatgtt atcgcttatg ttaatagtaa ttcccgtacg   4380
```

-continued

```
tgttcatttt attttcatgc tttttcagcc atgtatcaat attcacttga ctaaaatcac   4440

tcaattaatc aatgaaaaaa aaaaa                                          4465


<210> SEQ ID NO 5
<211> LENGTH: 314
<212> TYPE: PRT
<213> ORGANISM: Homo sapiens

<400> SEQUENCE: 5

Met Gly Ile Gly Arg Ser Glu Gly Gly Arg Arg Gly Ala Ala Leu Gly
1               5                   10                  15

Val Leu Leu Ala Leu Gly Ala Ala Leu Leu Ala Val Gly Ser Ala Ser
            20                  25                  30

Glu Tyr Asp Tyr Val Ser Phe Gln Ser Asp Ile Gly Pro Tyr Gln Ser
        35                  40                  45

Gly Arg Phe Tyr Thr Lys Pro Pro Gln Cys Val Asp Ile Pro Ala Asp
    50                  55                  60

Leu Arg Leu Cys His Asn Val Gly Tyr Lys Lys Met Val Leu Pro Asn
65                  70                  75                  80

Leu Leu Glu His Glu Thr Met Ala Glu Val Lys Gln Gln Ala Ser Ser
                85                  90                  95

Trp Val Pro Leu Leu Asn Lys Asn Cys His Ala Gly Thr Gln Val Phe
            100                 105                 110

Leu Cys Ser Leu Phe Ala Pro Val Cys Leu Asp Arg Pro Ile Tyr Pro
        115                 120                 125

Cys Arg Trp Leu Cys Glu Ala Val Arg Asp Ser Cys Glu Pro Val Met
    130                 135                 140

Gln Phe Phe Gly Phe Tyr Trp Pro Glu Met Leu Lys Cys Asp Lys Phe
145                 150                 155                 160

Pro Glu Gly Asp Val Cys Ile Ala Met Thr Pro Pro Asn Ala Thr Glu
                165                 170                 175

Ala Ser Lys Pro Gln Gly Thr Thr Val Cys Pro Pro Cys Asp Asn Glu
            180                 185                 190

Leu Lys Ser Glu Ala Ile Ile Glu His Leu Cys Ala Ser Glu Phe Ala
        195                 200                 205

Leu Arg Met Lys Ile Lys Glu Val Lys Lys Glu Asn Gly Asp Lys Lys
    210                 215                 220

Ile Val Pro Lys Lys Lys Lys Pro Leu Lys Leu Gly Pro Ile Lys Lys
225                 230                 235                 240

Lys Asp Leu Lys Lys Leu Val Leu Tyr Leu Lys Asn Gly Ala Asp Cys
                245                 250                 255

Pro Cys His Gln Leu Asp Asn Leu Ser His His Phe Leu Ile Met Gly
            260                 265                 270

Arg Lys Val Lys Ser Gln Tyr Leu Leu Thr Ala Ile His Lys Trp Asp
        275                 280                 285

Lys Lys Asn Lys Glu Phe Lys Asn Phe Met Lys Lys Met Lys Asn His
    290                 295                 300

Glu Cys Pro Thr Phe Gln Ser Val Phe Lys
305                 310


<210> SEQ ID NO 6
<211> LENGTH: 2005
<212> TYPE: DNA
<213> ORGANISM: Homo sapiens
```

-continued

<400> SEQUENCE: 6

```
caacggctca ttctgctccc ccgggtcgga gccccccgga gctgcgcgcg ggcttgcagc     60
gcctcgcccg cgctgtcctc ccggtgtccc gcttctccgc gccccagccg ccggctgcca    120
gcttttcggg gccccgagtc gcacccagcg aagagagcgg gcccgggaca agctcgaact    180
ccggccgcct cgcccttccc cggctccgct ccctctgccc cctcggggtc gcgcgcccac    240
gatgctgcag ggccctggct cgctgctgct gctcttcctc gcctcgcact gctgcctggg    300
ctcggcgcgc gggctcttcc tctttggcca gcccgacttc tcctacaagc gcagcaattg    360
caagcccatc cctgccaacc tgcagctgtg ccacggcatc gaataccaga acatgcggct    420
gcccaacctg ctgggccacg agaccatgaa ggaggtgctg gagcaggccg gcgcttggat    480
cccgctggtc atgaagcagt gccacccgga caccaagaag ttcctgtgct cgctcttcgc    540
ccccgtctgc ctcgatgacc tagacgagac catccagcca tgccactcgc tctgcgtgca    600
ggtgaaggac cgctgcgccc cggtcatgtc cgccttcggc ttcccctggc ccgacatgct    660
tgagtgcgac cgtttccccc aggacaacga cctttgcatc cccctcgcta gcagcgacca    720
cctcctgcca gccaccgagg aagctccaaa ggtatgtgaa gcctgcaaaa ataaaaatga    780
tgatgacaac gacataatgg aaacgctttg taaaaatgat tttgcactga aaataaaagt    840
gaaggagata acctacatca accgagatac caaaatcatc ctggagacca agagcaagac    900
catttacaag ctgaacggtg tgtccgaaag ggacctgaag aaatcggtgc tgtggctcaa    960
agacagcttg cagtgcacct gtgaggagat gaacgacatc aacgcgccct atctggtcat   1020
gggacagaaa cagggtgggg agctggtgat cacctcggtg aagcggtggc agaaggggca   1080
gagagagttc aagcgcatct cccgcagcat ccgcaagctg cagtgctagt cccggcatcc   1140
tgatggctcc gacaggcctg ctccagagca cggctgacca tttctgctcc gggatctcag   1200
ctcccgttcc ccaagcacac tcctagctgc tccagtctca gcctgggcag cttccccctg   1260
ccttttgcac gtttgcatcc ccagcatttc ctgagttata aggccacagg agtggatagc   1320
tgttttcacc taaaggaaaa gcccacccga atcttgtaga aatattcaaa ctaataaaat   1380
catgaatatt tttatgaagt ttaaaaatag ctcactttaa agctagtttt gaataggtgc   1440
aactgtgact tgggtctggt tggttgttgt ttgttgtttt gagtcagctg attttcactt   1500
cccactgagg ttgtcataac atgcaaattg cttcaatttt ctctgtggcc caaacttgtg   1560
ggtcacaaac cctgttgaga taaagctggc tgttatctca acatcttcat cagctccaga   1620
ctgagactca gtgtctaagt cttacaacaa ttcatcattt tataccttca atgggaactt   1680
aaactgttac atgtatcaca ttccagctac aatacttcca tttattagaa gcacattaac   1740
catttctata gcatgatttc ttcaagtaaa aggcaaaaga tataaatttt ataattgact   1800
tgagtacttt aagccttgtt taaaacattt cttacttaac ttttgcaaat taaacccatt   1860
gtagcttacc tgtaatatac atagtagttt acctttaaaa gttgtaaaaa tattgcttta   1920
accaacactg taaatatttc agataaacat tatattcttg tatataaact ttacatcctg   1980
ttttacctat aaaaaaaaaa aaaaa                                         2005
```

<210> SEQ ID NO 7
<211> LENGTH: 295
<212> TYPE: PRT
<213> ORGANISM: Homo sapiens

<400> SEQUENCE: 7

Met Leu Gln Gly Pro Gly Ser Leu Leu Leu Leu Phe Leu Ala Ser His

-continued

```
1               5                   10                  15

Cys Cys Leu Gly Ser Ala Arg Gly Leu Phe Leu Phe Gly Gln Pro Asp
            20                  25                  30

Phe Ser Tyr Lys Arg Ser Asn Cys Lys Pro Ile Pro Ala Asn Leu Gln
        35                  40                  45

Leu Cys His Gly Ile Glu Tyr Gln Asn Met Arg Leu Pro Asn Leu Leu
    50                  55                  60

Gly His Glu Thr Met Lys Glu Val Leu Glu Gln Ala Gly Ala Trp Ile
65                  70                  75                  80

Pro Leu Val Met Lys Gln Cys His Pro Asp Thr Lys Lys Phe Leu Cys
                85                  90                  95

Ser Leu Phe Ala Pro Val Cys Leu Asp Asp Leu Asp Glu Thr Ile Gln
            100                 105                 110

Pro Cys His Ser Leu Cys Val Gln Val Lys Asp Arg Cys Ala Pro Val
        115                 120                 125

Met Ser Ala Phe Gly Phe Pro Trp Pro Asp Met Leu Glu Cys Asp Arg
    130                 135                 140

Phe Pro Gln Asp Asn Asp Leu Cys Ile Pro Leu Ala Ser Ser Asp His
145                 150                 155                 160

Leu Leu Pro Ala Thr Glu Glu Ala Pro Lys Val Cys Glu Ala Cys Lys
                165                 170                 175

Asn Lys Asn Asp Asp Asp Asn Asp Ile Met Glu Thr Leu Cys Lys Asn
            180                 185                 190

Asp Phe Ala Leu Lys Ile Lys Val Lys Glu Ile Thr Tyr Ile Asn Arg
        195                 200                 205

Asp Thr Lys Ile Ile Leu Glu Thr Lys Ser Lys Thr Ile Tyr Lys Leu
    210                 215                 220

Asn Gly Val Ser Glu Arg Asp Leu Lys Lys Ser Val Leu Trp Leu Lys
225                 230                 235                 240

Asp Ser Leu Gln Cys Thr Cys Glu Glu Met Asn Asp Ile Asn Ala Pro
                245                 250                 255

Tyr Leu Val Met Gly Gln Lys Gln Gly Gly Glu Leu Val Ile Thr Ser
            260                 265                 270

Val Lys Arg Trp Gln Lys Gly Gln Arg Glu Phe Lys Arg Ile Ser Arg
        275                 280                 285

Ser Ile Arg Lys Leu Gln Cys
    290                 295


<210> SEQ ID NO 8
<211> LENGTH: 2058
<212> TYPE: DNA
<213> ORGANISM: Homo sapiens

<400> SEQUENCE: 8

gttgggaaag agcagcctgg gcggcagggg cggtggctgg agctcggtaa agctcgtggg      60

accccattgg gggaatttga tccaaggaag cggtgattgc cgggggagga gaagctccca     120

gatccttgtg tccacttgca gcgggggagg cggagacggc ggagcgggcc ttttggcgtc     180

cactgcgcgg ctgcaccctg ccccatcctg ccgggatcat ggtctgcggc agcccgggag     240

ggatgctgct gctgcgggcc gggctgcttg ccctggctgc tctctgcctg ctccgggtgc     300

ccggggctcg ggctgcagcc tgtgagcccg tccgcatccc cctgtgcaag tccctgccct     360

ggaacatgac taagatgccc aaccacctgc accacagcac tcaggccaac gccatcctgg     420

ccatcgagca gttcgaaggt ctgctgggca cccactgcag ccccgatctg ctcttcttcc     480
```

-continued

```
tctgtgccat gtacgcgccc atctgcacca ttgacttcca gcacgagccc atcaagccct    540

gtaagtctgt gtgcgagcgg gcccggcagg gctgtgagcc catactcatc aagtaccgcc    600

actcgtggcc ggagaacctg gcctgcgagg agctgccagt gtacgacagg ggcgtgtgca    660

tctctcccga ggccatcgtt actgcggacg gagctgattt tcctatggat tctagtaacg    720

gaaactgtag aggggcaagc agtgaacgct gtaaatgtaa gcctattaga gctacacaga    780

agacctattt ccggaacaat tacaactatg tcattcgggc taaagttaaa gagataaaga    840

ctaagtgcca tgatgtgact gcagtagtgg aggtgaagga gattctaaag tcctctctgg    900

taaacattcc acgggacact gtcaacctct ataccagctc tggctgcctc tgccctccac    960

ttaatgttaa tgaggaatat atcatcatgg gctatgaaga tgaggaacgt tccagattac   1020

tcttggtgga aggctctata gctgagaagt ggaaggatcg actcggtaaa aaagttaagc   1080

gctgggatat gaagcttcgt catcttggac tcagtaaaag tgattctagc aatagtgatt   1140

ccactcagag tcagaagtct ggcaggaact cgaacccccg gcaagcacgc aactaaatcc   1200

cgaaatacaa aaagtaacac agtggacttc ctattaagac ttacttgcat tgctggacta   1260

gcaaaggaaa attgcactat tgcacatcat attctattgt ttactataaa aatcatgtga   1320

taactgatta ttacttctgt ttctcttttg gtttctgctt ctctcttctc tcaacccctt   1380

tgtaatggtt tgggggcaga ctcttaagta tattgtgagt tttctatttc actaatcatg   1440

agaaaaactg ttcttttgca ataataataa attaaacatg ctgttaccag agcctctttg   1500

ctggagtctc cagatgttaa tttactttct gcaccccaat tgggaatgca atattggatg   1560

aaaagagagg tttctggtat tcacagaaag ctagatatgc cttaaaacat actctgccga   1620

tctaattaca gccttatttt tgtatgcctt ttgggcattc tcctcatgct tagaaagttc   1680

caaatgttta taaaggtaaa atggcagttt gaagtcaaat gtcacatagg caaagcaatc   1740

aagcaccagg aagtgtttat gaggaaacaa cacccaagat gaattatttt tgagactgtc   1800

aggaagtaaa ataaatagga gcttaagaaa gaacattttg cctgattgag aagcacaact   1860

gaaaccagta gccgctgggg tgttaatggt agcattcttc ttttggcaat acatttgatt   1920

tgttcatgaa tatattaatc agcattagag aaatgaatta taactagaca tctgctgtta   1980

tcaccatagt tttgtttaat ttgcttcctt ttaaataaac ccattggtga aagtcccaaa   2040

aaaaaaaaaa aaaaaaaa                                                 2058
```

```
<210> SEQ ID NO 9
<211> LENGTH: 325
<212> TYPE: PRT
<213> ORGANISM: Homo sapiens

<400> SEQUENCE: 9

Met Val Cys Gly Ser Pro Gly Gly Met Leu Leu Leu Arg Ala Gly Leu
1               5                   10                  15

Leu Ala Leu Ala Ala Leu Cys Leu Leu Arg Val Pro Gly Ala Arg Ala
            20                  25                  30

Ala Ala Cys Glu Pro Val Arg Ile Pro Leu Cys Lys Ser Leu Pro Trp
        35                  40                  45

Asn Met Thr Lys Met Pro Asn His Leu His His Ser Thr Gln Ala Asn
    50                  55                  60

Ala Ile Leu Ala Ile Glu Gln Phe Glu Gly Leu Leu Gly Thr His Cys
65                  70                  75                  80

Ser Pro Asp Leu Leu Phe Phe Leu Cys Ala Met Tyr Ala Pro Ile Cys
```

-continued

```
                85                  90                  95

Thr Ile Asp Phe Gln His Glu Pro Ile Lys Pro Cys Lys Ser Val Cys
            100                 105                 110

Glu Arg Ala Arg Gln Gly Cys Glu Pro Ile Leu Ile Lys Tyr Arg His
        115                 120                 125

Ser Trp Pro Glu Asn Leu Ala Cys Glu Glu Leu Pro Val Tyr Asp Arg
    130                 135                 140

Gly Val Cys Ile Ser Pro Glu Ala Ile Val Thr Ala Asp Gly Ala Asp
145                 150                 155                 160

Phe Pro Met Asp Ser Ser Asn Gly Asn Cys Arg Gly Ala Ser Ser Glu
                165                 170                 175

Arg Cys Lys Cys Lys Pro Ile Arg Ala Thr Gln Lys Thr Tyr Phe Arg
            180                 185                 190

Asn Asn Tyr Asn Tyr Val Ile Arg Ala Lys Val Lys Glu Ile Lys Thr
        195                 200                 205

Lys Cys His Asp Val Thr Ala Val Val Glu Val Lys Glu Ile Leu Lys
    210                 215                 220

Ser Ser Leu Val Asn Ile Pro Arg Asp Thr Val Asn Leu Tyr Thr Ser
225                 230                 235                 240

Ser Gly Cys Leu Cys Pro Pro Leu Asn Val Asn Glu Glu Tyr Ile Ile
                245                 250                 255

Met Gly Tyr Glu Asp Glu Glu Arg Ser Arg Leu Leu Leu Val Glu Gly
            260                 265                 270

Ser Ile Ala Glu Lys Trp Lys Asp Arg Leu Gly Lys Lys Val Lys Arg
        275                 280                 285

Trp Asp Met Lys Leu Arg His Leu Gly Leu Ser Lys Ser Asp Ser Ser
    290                 295                 300

Asn Ser Asp Ser Thr Gln Ser Gln Lys Ser Gly Arg Asn Ser Asn Pro
305                 310                 315                 320

Arg Gln Ala Arg Asn
                325
```

<210> SEQ ID NO 10
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 10
cggauuguaa agaacugcat t 21

<210> SEQ ID NO 11
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 11
ugcaguucuu uacaauccgt t 21

<210> SEQ ID NO 12
<211> LENGTH: 21
<212> TYPE: DNA
<213> ORGANISM: Artificial Sequence
<220> FEATURE:
<223> OTHER INFORMATION: Chemically synthesized primer -continued

<400> SEQUENCE: 12
ggacgacaac gacaucaugt t 21

<210> SEQ ID NO 13
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 13
caugaugucg uugucgucct c 21

<210> SEQ ID NO 14
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 14
ccgucaaucu uuauaccact t 21

<210> SEQ ID NO 15
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 15
gugguauaaa gauugacggt g 21

<210> SEQ ID NO 16
<211> LENGTH: 4091
<212> TYPE: DNA
<213> ORGANISM: Homo sapiens

<400> SEQUENCE: 16
gccggagtcg gagggcgggg agctaggagg agggagctcg agagttgtgg agactagtga 60
ctgggagaag tcgcagcccg ctcaggcccg cgccttcccg ctccccgtct tcctctctca 120
cacacctact ccgccctccg ccccagcccg cgcgctagct ccttctctcg cccggggttc 180
ctgccggtag ctctccgggt cttggcgcgg cgggggcgcc ccgggggtgc cctcgccctc 240
ccgttgcggg cgggcgggcg gtatgtggcg cctggtgccc ccgaagctgg gccgcctgtc 300
ccgctcgctg aagctggcgg cgctgggcag cctgttggtg ctgatggtgc tgcactcgcc 360
gtcgctgctc gcctcttggc agcgcaacga actgaccgac cggcgcttcc tgcagctcaa 420
taagtgcccg gcgtgcttcg gcacgagctg gtgccgccgc ttcctcaacg ggcaggtggt 480
attcgaggcg tggggccgct tgcgcctgct ggacttcctc aacgtgaaga acgtgtactt 540
cgcgcagtac ggcgagcccc gcgagggcgg ccgccgccga gtggtgctca agcgcctcgg 600
ctcgcagcgc gagctggcgc agctcgacca gagcatctgc aagcgggcca ccggccggcc 660
ccgctgcgac ctgctgcagg ccatgccccg gaccgagttc gcgcgcctca acggcgacgt 720
gcgtctgctc acgcccgagg cggtggaggg ctggtcggac ctggtgcact gcccctcgca 780
gcgccttctc gaccgcctgg tgcgccgcta cgcggagacc aaggactcgg gcagcttcct 840
gcttcgcaac ctcaaggact cggagcgcat gcagctgctg ctgaccctgg ccttcaaccc 900
cgagccgctg gtgctacaga gttttccgtc tgatgaaggt tggccatttg caaagtatct 960

-continued

```
tggagcttgt ggaagaatgg tggctgtaaa ttatgttgga gaagaactgt ggagttactt   1020
taatgcgcca tgggaaaaac gagttgacct cgcttggcaa ttaatggaaa tagcagaaca   1080
gcttacaaac aatgactttg aatttgcact ctacctcctg gacgtcagct ttgacaattt   1140
tgcagttggt cctagagatg ggaaggtaat cattgtggat gctgaaaatg ttttggttgc   1200
tgacaaaaga ttaattagac aaaataaacc tgaaaattgg gatgtatggt atgaaagcaa   1260
gtttgatgac tgtgataagg aggcttgctt atcattttca aaagaaattc tttgtgctcg   1320
tgccactgtg gaccacaatt actatgctgt ttgtcagaac ctcttatcca gacatgccac   1380
ctggcgtggc acttctggag gactccttca tgatccacca agtgaaattg ccaaagatgg   1440
ccggctcgag gccttgctgg atgagtgtgc caacccaaag aagcgctatg gcagattcca   1500
ggctgcaaaa gaactgcgtg aatacctagc acaattaagt aacaacgtga ggtagtctat   1560
ggtgaacttt tcttttttc tccatttaaa cagcactggc taaaactaaa ccaccaaaaa   1620
acgatctgaa aaaatgaaat ttggaagtgt tacattcaga ggatgataaa cttgcactga   1680
tagatcttaa tgttaacatc catcaaaata agacattact tcaaaaatca catgatgctt   1740
ctgcaaataa gtatgttctt atactttgga ggcttgagct gtcatcagct gctcccact   1800
accccggaat gcttgagtgg attaatgaat attgttaagc tattggaaat gagtctgata   1860
gtacattggc ttgtgtatca aagggtactt ggtacttagt ttgcatttac tatcatgatt   1920
ttgtgaatct cttgcattta ctttgaatgt caagtcagat tggtctgttt tataggccgc   1980
tttttccttc tgatgtgtag ggttttttcc cccttttttt ttttaattaa attttgaaaa   2040
ttcaggttac tgtaggtgtt catttaaatt tttaatagtt gtcattcagt gctatttggt   2100
acatatttac tgttagggca ggattcccag gtttactgtg ttttttttt ttttttttta   2160
aagaaagcta aatattacat tatgtaaata cttcttttca ccaacttctg tagtttcacc   2220
attgcatggt gtcatttcag gttatttaac agttatatcc ctctatgcca ataattagaa   2280
gtgtacacta aacatgaagt ttggcatatg ttgcaaaatg tcattttatc tttctaaagg   2340
ctttaagaag aatatactag aatctatata ttgatgttaa ttttgattca gaaaaaaaat   2400
acaacccagt atctaaaaag tgttaactag tccaagatag taatgcatat gccaaagaaa   2460
tattacacct aatctcatgt ttagaattta aaatagaatt ggtcagctac ttattcttac   2520
caccctactt ccagtatttt agctctgtca ttattaaatt cagatcttcc tgattatttt   2580
ttctgttgaa agttaaacta ctgctttcaa gtaatttaaa gttatcctac cttttattca   2640
tgggtagttt tgcaaaatta acatggtagc cattgtttga atttaatcgg gcatcataac   2700
ttttcattta ttgaggaact aatcattatt actataaagc atacaaatta gccagtcagc   2760
acactttggt cttctttacc taagggttaa acatcagaac atcaaattta attatttgca   2820
tagaaatgtg tgggctcttt atataagttg actatcacta acaggtaata tttttctgtt   2880
tgaagttgtt acttttgttt acagcaaagt ttgatgtagt gtgcagtagt gagctctaga   2940
ctgatctttt tctaaatcag aaagtgatta aagtatgcac aaccaaaggc aggtttttct   3000
ttttcattta ttcagcaact atttattaag catcaactct gtgccaggca cgttactagc   3060
tgctacatac tgtctgaaca tgacatacgg ttaagtaact ttacaattat tatcaaatac   3120
ttcaatgtag atatttctta agttgaaata gcattaacta ggataatgct ttcatgttat   3180
tttattgtct tgtgatagaa attcaacttg taccatctaa aactaggttg ctataaaaat   3240
aggaggatga agtcaataaa gtttatgcca gtttaaaaac tggaaggaaa aggtaagagc   3300
```

-continued

```
tctccattat aaaatagttg cattcggtta atttttacac attagtgcat tgcgtatatc   3360

aactggccct caatgaagca tttaagtgct tggaatttta ctaaactgac ttttttgcaa   3420

ctttgggaga tttttgaggg gagtgttgaa aattgccaaa cactcacctc ttactcaaaa   3480

cttcaaataa aatacacatt ttcaagaggg agcacctttt atatttgata agttttcatt   3540

ataaacctta taataccagt cacaaagagg ttgtctgtct atggtttagc aaacatttgc   3600

ttttcttttt ggaagtgtga ttgcaattgc agaacagaaa gtgagaaaac actgccagcg   3660

gtgattgcta cttgaggtag ttttttacaa ctaccatttc ccctccatga aattatgtga   3720

aatttatttt atctttggga aaagttgaga agatagtaaa agaattagga atttaaaatt   3780

acagggaaaa atatgtaagt gaaaagcaat aaatattttg ttcactttgc tatcaagatg   3840

ttcactatca gatatttatt atatggcagc aatttatatt tttaatcatt gcccattaat   3900

agacgcagta aaatattttt gaatcagaca tttggggttt gtatgtgcat taaaattgtc   3960

ttttgtactg taagttactg ttaatttgaa tattttattg aactgtctcc ctgtgccttt   4020

ataatataaa gttgtttcta caacttttaa tgatcttaat aaagaatact ttaggaaaaa   4080

aaaaaaaaaa a                                                        4091


<210> SEQ ID NO 17
<211> LENGTH: 430
<212> TYPE: PRT
<213> ORGANISM: Homo sapiens

<400> SEQUENCE: 17

Met Trp Arg Leu Val Pro Pro Lys Leu Gly Arg Leu Ser Arg Ser Leu
1               5                   10                  15

Lys Leu Ala Ala Leu Gly Ser Leu Leu Val Leu Met Val Leu His Ser
            20                  25                  30

Pro Ser Leu Leu Ala Ser Trp Gln Arg Asn Glu Leu Thr Asp Arg Arg
        35                  40                  45

Phe Leu Gln Leu Asn Lys Cys Pro Ala Cys Phe Gly Thr Ser Trp Cys
    50                  55                  60

Arg Arg Phe Leu Asn Gly Gln Val Val Phe Glu Ala Trp Gly Arg Leu
65                  70                  75                  80

Arg Leu Leu Asp Phe Leu Asn Val Lys Asn Val Tyr Phe Ala Gln Tyr
                85                  90                  95

Gly Glu Pro Arg Glu Gly Gly Arg Arg Arg Val Val Leu Lys Arg Leu
            100                 105                 110

Gly Ser Gln Arg Glu Leu Ala Gln Leu Asp Gln Ser Ile Cys Lys Arg
        115                 120                 125

Ala Thr Gly Arg Pro Arg Cys Asp Leu Leu Gln Ala Met Pro Arg Thr
    130                 135                 140

Glu Phe Ala Arg Leu Asn Gly Asp Val Arg Leu Leu Thr Pro Glu Ala
145                 150                 155                 160

Val Glu Gly Trp Ser Asp Leu Val His Cys Pro Ser Gln Arg Leu Leu
                165                 170                 175

Asp Arg Leu Val Arg Arg Tyr Ala Glu Thr Lys Asp Ser Gly Ser Phe
            180                 185                 190

Leu Leu Arg Asn Leu Lys Asp Ser Glu Arg Met Gln Leu Leu Leu Thr
        195                 200                 205

Leu Ala Phe Asn Pro Glu Pro Leu Val Leu Gln Ser Phe Pro Ser Asp
    210                 215                 220

Glu Gly Trp Pro Phe Ala Lys Tyr Leu Gly Ala Cys Gly Arg Met Val
```

-continued

```
225                 230                 235                 240

Ala Val Asn Tyr Val Gly Glu Glu Leu Trp Ser Tyr Phe Asn Ala Pro
                245                 250                 255

Trp Glu Lys Arg Val Asp Leu Ala Trp Gln Leu Met Glu Ile Ala Glu
            260                 265                 270

Gln Leu Thr Asn Asn Asp Phe Glu Phe Ala Leu Tyr Leu Leu Asp Val
        275                 280                 285

Ser Phe Asp Asn Phe Ala Val Gly Pro Arg Asp Gly Lys Val Ile Ile
    290                 295                 300

Val Asp Ala Glu Asn Val Leu Val Ala Asp Lys Arg Leu Ile Arg Gln
305                 310                 315                 320

Asn Lys Pro Glu Asn Trp Asp Val Trp Tyr Glu Ser Lys Phe Asp Asp
                325                 330                 335

Cys Asp Lys Glu Ala Cys Leu Ser Phe Ser Lys Glu Ile Leu Cys Ala
            340                 345                 350

Arg Ala Thr Val Asp His Asn Tyr Tyr Ala Val Cys Gln Asn Leu Leu
        355                 360                 365

Ser Arg His Ala Thr Trp Arg Gly Thr Ser Gly Gly Leu Leu His Asp
    370                 375                 380

Pro Pro Ser Glu Ile Ala Lys Asp Gly Arg Leu Glu Ala Leu Leu Asp
385                 390                 395                 400

Glu Cys Ala Asn Pro Lys Lys Arg Tyr Gly Arg Phe Gln Ala Ala Lys
                405                 410                 415

Glu Leu Arg Glu Tyr Leu Ala Gln Leu Ser Asn Asn Val Arg
            420                 425                 430
```

<210> SEQ ID NO 18
<211> LENGTH: 2437
<212> TYPE: DNA
<213> ORGANISM: Homo sapiens

<400> SEQUENCE: 18

```
gcatcttggc agggtccggg gacgtggact atttcgcaca ccacaccacg gggagggatt     60

tttttctatt ttccctacga aaaacagatc tttttaagga tggtgctgct ccactggtgc    120

ctgctgtggc tcctgtttcc actcagctca aggacccaga agttacccac ccgggatgag    180

gaactttttc agatgcagat ccgggacaag gcatttttc atgattcgtc agtaattcca     240

gatggagctg aaattagcag ttatctcttt agagatacac ctaaaaggta tttctttgtg    300

gttgaagaag acaatactcc attatcagtc acagtgacgc cctgtgatgc gcctttggag    360

tggaagctga gcctccagga gctgccagag gacaggagcg gggaaggctc aggtgatctg    420

gaacctcttg agcagcagaa gcagcagatc attaatgagg aaggcactga gttattctcc    480

tacaaaggca atgatgttga gtattttata tcgtctagtt ccccatccgg tttgtatcag    540

ttggatcttc tttcaacaga gaaagacaca catttcaaag tatatgccac cacaactcca    600

gaatctgatc agccataccc tgagttaccc tatgacccaa gagtagatgt gacctcactg    660

gggcgcacca cggtcacttt ggcctggaaa ccaagcccca ctgcctcttt gctgaaacaa    720

cccattcagt actgtgtggt catcaacaaa gagcacaatt tcaaaagtct ctgtgcagtg    780

gaagcaaaac tgagtgcaga tgatgctttt atgatggcac cgaaacctgg tctggacttc    840

agccccttg actttgccca ctttggattt ccttctgata attcaggtaa agaacgcagt     900

ttccaggcaa agccttctcc aaaactgggg cgtcatgtct actccaggcc caaggttgat    960

attcagaaaa tctgcatagg aaacaagaac atcttcaccg tctctgatct gaaacccgac   1020
```

-continued

```
acgcagtact actttgatgt atttgtggtc aacatcaaca gcaacatgag caccgcttat   1080

gtaggtacct ttgccaggac caaggaagaa gccaaacaga agacagtcga gctaaaagat   1140

gggaagataa cagatgtatt tgttaaaagg aagggagcaa agtttctacg gtttgctcca   1200

gtctcttctc accaaaaagt caccttcttt attcactctt gtctggatgc tgtccaaatc   1260

caagtgagaa gagatgggaa acttcttctg tctcagaatg tggaaggcat tcagcagttt   1320

cagcttagag gaaaacctaa agctaaatac ctcgttcgac tgaaaggaaa caagaaagga   1380

gcatctatgt tgaaaattct agctaccaca aggcctacta agcagtcatt tccctctctt   1440

cctgaagaca caagaatcaa agcctttgac aagctccgta cctgttcctc ggccaccgtg   1500

gcttggctag gcactcagga aaggaacaag ttttgcatct acaaaaaaga agtggatgat   1560

aactacaatg aagaccagaa gaaaagagag caaaaccaat gtctaggacc agatataagg   1620

aagaagtcag aaaaggtcct ctgtaaatat ttccacagtc aaaacttgca gaaagcagtg   1680

accacagaaa caattaaagg tcttcagcct ggcaaatctt acctgctgga tgtttatgtc   1740

ataggacatg gggggcactc tgtaaagtat cagagtaagg ttgtgaaaac tagaaagttc   1800

tgttagttac cttcttatag agatatatta tgtagaactc caggagggac attaaatcac   1860

tttaagtata aactgactac tcccacagtt gagagaagtt gtgacctgta cttgtactat   1920

ggaaggaagg atatcaacgt gtgtatattg atgtttatat aagtaactct tgaaggagac   1980

ttgttctagc gtgccccatg gtacctagtg tgtgtctgat gccggttggt gtcaaagata   2040

gagggcttct tgaaggaact tgccattcct tgctttgacc actgcatgaa ctgcttctaa   2100

attattttat tacctaaaaa tttaaaatat gccattcatt gcacacaccc acaaatgcaa   2160

atcattcctc tctatagatg ctaggatata tataaattat tttataaatt cttgttttaa   2220

atgtcagtgt ttctatgatt gtaaactatt aaattctttt cctattaaag tacagatcta   2280

atctaagtat tattaagttg atagccctct agtcagttat attgctattg taaattcttg   2340

tttgttgagt aaaatgttta aatactatat gtatctcatg tacaaagttg acatacatta   2400

tattcatgta cataaaatta aagagattag attataa                            2437
```

<210> SEQ ID NO 19
<211> LENGTH: 568
<212> TYPE: PRT
<213> ORGANISM: Homo sapiens

<400> SEQUENCE: 19

```
Met Val Leu Leu His Trp Cys Leu Leu Trp Leu Leu Phe Pro Leu Ser
1               5                   10                  15

Ser Arg Thr Gln Lys Leu Pro Thr Arg Asp Glu Glu Leu Phe Gln Met
            20                  25                  30

Gln Ile Arg Asp Lys Ala Phe Phe His Asp Ser Ser Val Ile Pro Asp
        35                  40                  45

Gly Ala Glu Ile Ser Ser Tyr Leu Phe Arg Asp Thr Pro Lys Arg Tyr
    50                  55                  60

Phe Phe Val Val Glu Glu Asp Asn Thr Pro Leu Ser Val Thr Val Thr
65                  70                  75                  80

Pro Cys Asp Ala Pro Leu Glu Trp Lys Leu Ser Leu Gln Glu Leu Pro
                85                  90                  95

Glu Asp Arg Ser Gly Glu Gly Ser Gly Asp Leu Glu Pro Leu Glu Gln
            100                 105                 110

Gln Lys Gln Gln Ile Ile Asn Glu Glu Gly Thr Glu Leu Phe Ser Tyr
```

-continued

```
        115                 120                 125

Lys Gly Asn Asp Val Glu Tyr Phe Ile Ser Ser Ser Ser Pro Ser Gly
    130                 135                 140

Leu Tyr Gln Leu Asp Leu Leu Ser Thr Glu Lys Asp Thr His Phe Lys
145                 150                 155                 160

Val Tyr Ala Thr Thr Thr Pro Glu Ser Asp Gln Pro Tyr Pro Glu Leu
                165                 170                 175

Pro Tyr Asp Pro Arg Val Asp Val Thr Ser Leu Gly Arg Thr Thr Val
            180                 185                 190

Thr Leu Ala Trp Lys Pro Ser Pro Thr Ala Ser Leu Leu Lys Gln Pro
        195                 200                 205

Ile Gln Tyr Cys Val Val Ile Asn Lys Glu His Asn Phe Lys Ser Leu
    210                 215                 220

Cys Ala Val Glu Ala Lys Leu Ser Ala Asp Asp Ala Phe Met Met Ala
225                 230                 235                 240

Pro Lys Pro Gly Leu Asp Phe Ser Pro Phe Asp Phe Ala His Phe Gly
                245                 250                 255

Phe Pro Ser Asp Asn Ser Gly Lys Glu Arg Ser Phe Gln Ala Lys Pro
            260                 265                 270

Ser Pro Lys Leu Gly Arg His Val Tyr Ser Arg Pro Lys Val Asp Ile
        275                 280                 285

Gln Lys Ile Cys Ile Gly Asn Lys Asn Ile Phe Thr Val Ser Asp Leu
    290                 295                 300

Lys Pro Asp Thr Gln Tyr Tyr Phe Asp Val Phe Val Val Asn Ile Asn
305                 310                 315                 320

Ser Asn Met Ser Thr Ala Tyr Val Gly Thr Phe Ala Arg Thr Lys Glu
                325                 330                 335

Glu Ala Lys Gln Lys Thr Val Glu Leu Lys Asp Gly Lys Ile Thr Asp
            340                 345                 350

Val Phe Val Lys Arg Lys Gly Ala Lys Phe Leu Arg Phe Ala Pro Val
        355                 360                 365

Ser Ser His Gln Lys Val Thr Phe Phe Ile His Ser Cys Leu Asp Ala
    370                 375                 380

Val Gln Ile Gln Val Arg Arg Asp Gly Lys Leu Leu Leu Ser Gln Asn
385                 390                 395                 400

Val Glu Gly Ile Gln Gln Phe Gln Leu Arg Gly Lys Pro Lys Ala Lys
                405                 410                 415

Tyr Leu Val Arg Leu Lys Gly Asn Lys Lys Gly Ala Ser Met Leu Lys
            420                 425                 430

Ile Leu Ala Thr Thr Arg Pro Thr Lys Gln Ser Phe Pro Ser Leu Pro
        435                 440                 445

Glu Asp Thr Arg Ile Lys Ala Phe Asp Lys Leu Arg Thr Cys Ser Ser
    450                 455                 460

Ala Thr Val Ala Trp Leu Gly Thr Gln Glu Arg Asn Lys Phe Cys Ile
465                 470                 475                 480

Tyr Lys Lys Glu Val Asp Asp Asn Tyr Asn Glu Asp Gln Lys Lys Arg
                485                 490                 495

Glu Gln Asn Gln Cys Leu Gly Pro Asp Ile Arg Lys Lys Ser Glu Lys
            500                 505                 510

Val Leu Cys Lys Tyr Phe His Ser Gln Asn Leu Gln Lys Ala Val Thr
        515                 520                 525

Thr Glu Thr Ile Lys Gly Leu Gln Pro Gly Lys Ser Tyr Leu Leu Asp
    530                 535                 540
```

-continued

Val Tyr Val Ile Gly His Gly Gly His Ser Val Lys Tyr Gln Ser Lys
545 550 555 560

Val Val Lys Thr Arg Lys Phe Cys
565

<210> SEQ ID NO 20
<211> LENGTH: 800
<212> TYPE: DNA
<213> ORGANISM: Homo sapiens

<400> SEQUENCE: 20
agcgggatag cccgcggccg cgcctgcccg ctcgcacccc tctcccgcgc ccggttctcc 60
ctcgcagcac ctcgaagtgc gcccctcgcc ctcctgctcg cgccccgccg ccatggctgc 120
ctcccccgcg cggcctgctg tcctggccct gaccgggctg gcgctgctcc tgctcctgtg 180
ctggggccca ggtggcataa gtggaaataa actcaagctg atgcttcaaa aacgagaagc 240
acctgttcca actaagacta aagtggccgt tgatgagaat aaagccaaag aattccttgg 300
cagcctgaag cgccagaagc ggcagctgtg ggaccggact cggcccgagg tgcagcagtg 360
gtaccagcag tttctctaca tgggctttga cgaagcgaaa tttgaagatg acatcaccta 420
ttggcttaac agagatcgaa atggacatga atactatggc gattactacc aacgtcacta 480
tgatgaagac tctgcaattg gtccccggag cccctacggc tttaggcatg gagccagcgt 540
caactacgat gactactaac catgacttgc cacacgctgt acaagaagca aatagcgatt 600
ctcttcatgt atctcctaat gccttacact acttggtttc tgatttgctc tatttcagca 660
gatcttttct acctactttg tgtgatcaaa aaagaagagt taaaacaaca catgtaaatg 720
ccttttgata tttcatggga atgcctctca tttaaaaata gaaataaagc attttgttaa 780
aaagaaaaaa aaaaaaaaaa 800

<210> SEQ ID NO 21
<211> LENGTH: 148
<212> TYPE: PRT
<213> ORGANISM: Homo sapiens

<400> SEQUENCE: 21

Met Ala Ala Ser Pro Ala Arg Pro Ala Val Leu Ala Leu Thr Gly Leu
1 5 10 15

Ala Leu Leu Leu Leu Leu Cys Trp Gly Pro Gly Gly Ile Ser Gly Asn
20 25 30

Lys Leu Lys Leu Met Leu Gln Lys Arg Glu Ala Pro Val Pro Thr Lys
35 40 45

Thr Lys Val Ala Val Asp Glu Asn Lys Ala Lys Glu Phe Leu Gly Ser
50 55 60

Leu Lys Arg Gln Lys Arg Gln Leu Trp Asp Arg Thr Arg Pro Glu Val
65 70 75 80

Gln Gln Trp Tyr Gln Gln Phe Leu Tyr Met Gly Phe Asp Glu Ala Lys
85 90 95

Phe Glu Asp Asp Ile Thr Tyr Trp Leu Asn Arg Asp Arg Asn Gly His
100 105 110

Glu Tyr Tyr Gly Asp Tyr Tyr Gln Arg His Tyr Asp Glu Asp Ser Ala
115 120 125

Ile Gly Pro Arg Ser Pro Tyr Gly Phe Arg His Gly Ala Ser Val Asn
130 135 140

Tyr Asp Asp Tyr

-continued

145

<210> SEQ ID NO 22
<211> LENGTH: 4533
<212> TYPE: DNA
<213> ORGANISM: Homo sapiens

<400> SEQUENCE: 22
cactgggaga cagtccactt aaatgcagct ccagggttgc gaggcaccca ccagcatcat 60
tccccatgcg aggtggcaaa tgcaacatgc tctccagttt ggggtgtcta cttctctgtg 120
gaagtattac actagccctg ggaaatgcac agaaattgcc aaaaggtaaa aggccaaacc 180
tcaaagtcca catcaatacc acaagtgact ccatcctctt gaagttcttg cgtccaagtc 240
caaatgtaaa gcttgaaggt cttctcctgg gatatggcag caatgtatca ccaaaccagt 300
acttccctct tcccgctgaa gggaaattca cagaagctat agttgatgca gagccgaaat 360
atctgatagt tgtgcgacct gctccacctc caagtcaaaa gaagtcatgt tcaggtaaaa 420
ctcgttctcg caaacctctg cagctggtgg ttggcactct gacaccgagc tcagtcttcc 480
tgtcctgggg tttcctcatc aacccacacc atgactggac attgccaagt cactgtccca 540
atgacagatt ttatacaatt cgctatcgag aaaaggataa agaaaagaag tggatttttc 600
aaatctgtcc agccactgaa acaattgtgg aaaacctaaa gcccaacaca gtttatgaat 660
ttggagtgaa agacaatgtg gaaggtggaa tttggagtaa gattttcaat cacaagactg 720
ttgttggaag taaaaaagta aatgggaaaa tccaaagtac ctatgaccaa gaccacacag 780
tgccagcata tgtcccaagg aaactaatcc caataacaat catcaagcaa gtgattcaga 840
atgttactca caaggattca gctaaatccc cagaaaaagc tccactggga ggagtgatac 900
tagtccacct tattattcca ggtcttaatg aaactactgt aaaacttcct gcatccctaa 960
tgtttgagat ttcagatgca ctcaagacac aattagctaa gaatgaaacc ttggcattac 1020
ctgccgaatc taaaacacca gaggttgaaa aaatctcagc acgacccaca acagtgactc 1080
ctgaaacagt tccaagaagc actaaaccca ctacgtctag tgcattagat gtttcagaaa 1140
caacactggc ttcaagtgaa aagccatgga ttgtgcctac agctaaaata tctgaagatt 1200
ccaaagttct gcagcctcaa actgcaactt atgatgtttt ctcaagccct acaacatcag 1260
atgagcctga gatatcagat tcctacacag caacaagtga tcgtattctg gattctatcc 1320
cacctaaaac ttctagaact cttgaacagc caagggcaac actggctcca agtgaaacac 1380
catttgttcc tcaaaaactg gaaatcttta ccagtccaga aatgcagcct acgacacctg 1440
ctccccagca aactacatct atcccttcta cacctaaacg acgcccccgg cccaaaccgc 1500
caagaaccaa acctgaaaga accacaagtg ccggaacaat tacacctaaa atttctaaaa 1560
gccctgaacc tacatggaca acaccggctc ccggtaaaac acaatttatt tctctgaaac 1620
ctaaaatccc tctcagccca gaagtgacac acaccaaacc tgctcccaag cagacaccac 1680
gtgctcctcc taagccaaaa acatcaccac gcccaagaat cccacaaaca caaccagttc 1740
ctaaggtgcc ccagcgtgtt actgcaaaac caaaaacgtc accaagtcca gaagtgtcat 1800
acaccacacc tgctccaaaa gatgtgctcc ttcctcataa accataccct gaggtctctc 1860
agagcgaacc tgctcctcta gagacacgag gcatcccttt tatacccatg atttccccaa 1920
gtcctagtca agaggaacta cagaccactc tggaagaaac agaccaatcc acccaagaac 1980
ctttcacaac taagattcca cgaacaactg aactagcaaa gacaactcag gcgccacaca 2040
gattttatac tactgtgagg cccagaacat ctgacaagcc acacatcaga cctggggtca 2100

-continued

```
agcaagcacc caggccatca ggtgctgata gaaatgtatc agtggactct acccacccca   2160
ctaaaaagcc agggactcgc cgcccaccct tgccacccag acctacacac ccacgaagaa   2220
aacctttacc accaaataat gtcactggaa agccaggaag tgcaggaatc atttcatcag   2280
gcccaataac tacaccaccc ctgaggtcaa cacccaggcc tactggaact cccttggaga   2340
gaatagagac agatataaag caaccaacag ttcctgcctc tggagaagaa ctggaaaata   2400
taactgactt tagctcaagc ccaacaagag aaactgatcc tcttgggaag ccaagattca   2460
aaggacctca tgtgcgatac atccaaaagc ctgacaacag tccctgctcc attactgact   2520
ctgtcaaacg gttccccaaa gaggaggcca cagaggggaa tgccaccagc ccaccacaga   2580
acccacccac caacctcact gtggtcaccg tggaagggtg cccctcattt gtcatcttgg   2640
actgggaaaa gccactaaat gacactgtca ctgaatatga agttatatcc agagaaaatg   2700
ggtcattcag tgggaagaac aagtccattc aaatgacaaa tcagacattt tccacagtag   2760
aaaatctgaa accaaacacg agttatgaat tccaggtgaa acccaaaaac ccgcttggtg   2820
aaggcccggt cagcaacaca gtggcattca gtactgaatc agcggaccca agagtgagtg   2880
agccagtttc tgcaggaaga gatgccatct ggactgaaag accctttaat tcagactctt   2940
actcagagtg taagggcaaa caatatgtca aaaggacatg gtataaaaaa tttgtaggag   3000
tgcagctgtg caactctctc agatacaaga tttacttgag cgactccctc acaggaaaat   3060
tttataacat aggtgatcag aggggccatg gagaagatca ctgccagttt gtggattcat   3120
ttttagatgg acgcactggg cagcaactca cttctgacca gttaccaatc aaagaaggtt   3180
atttcagagc agttcgccag gaacctgtcc aatttggaga aataggtggt cacacccaaa   3240
tcaattatgt tcagtggtat gaatgtggga ctacaattcc tggaaaatgg tagatgctgc   3300
acaaagttac cttctgtttc atcattgcaa acaaaaatca ttgaaaatac tatgccgcat   3360
tcatttaaag ctattttgtt tactatgtat aaaagtctac aatctaatta atagcaatac   3420
tagatgttta ttattagaaa agattgctga gagtatttat caggttttac aaagtcattt   3480
taagaaagca agatactgat gttaacagaa taacattttt ggggaagctg gctccctatt   3540
catggtattt taagagatca tttgtatatt atttatcaca ctgttgtaat gatgttttga   3600
gatactttta taacaaaatt aacatcaaaa aggtatatac tttttaaaaa aaatttactt   3660
ttattgatgt gtactcttcc tattgatgag ttaattccat aaatctctac ttagtttaac   3720
ttattggatc aaattatctt cagcatgtat atctggggaa aaaaggtccg aattttcaca   3780
tttatattta aacttcaatt ttttatattt aaacttcaat tttttagcaa cagctgaata   3840
gctttgcgga ggagtttaat agttacacat tcatgctaat atacatttcc tttaaacatc   3900
cacaaattct taaaaagatt gaatcagtaa atttcatttc agctaaaaat ggagtctaat   3960
atattgtttc aaaagataca tttttaccca ccataaatgt tacaatatct gaatatgctt   4020
tgtcaaacta tccctttatg caatcgtctt catattgttt ttatgattct aatcaagctg   4080
tatgtagaga ctgaatgtga agtcaagtct gagcacaaaa agataatgca caatgagatt   4140
gcctaccatt ttataggata tttactatgt atttatacgt taagacctct atgaatgaat   4200
gtatcagaga atgtctttgt aactaactgt ttaattcaat ctgtaataaa aatctaacta   4260
actaactcat ttatttctat taaaaaggta ttgtccttta ggcggggaat gggaatcctt   4320
gctgcactgt tgcagtcatt ctgaaaggac ctttccctgt acttaccttt caacatgctt   4380
caatcttatc aacgctacat tttgtatttt tcaaacaggt ataaattctg caataaagag   4440
```

-continued

```
atgtagtttt tttttaaaaa aaaaaaaaaa aaaaaaaaaa aaaaaaaaaa aaaaaaaaaa   4500

aaaaaaaaaa aaaaaaaaaa aaaaaaaaaa aaa                                 4533


<210> SEQ ID NO 23
<211> LENGTH: 1075
<212> TYPE: PRT
<213> ORGANISM: Homo sapiens

<400> SEQUENCE: 23

Met Arg Gly Gly Lys Cys Asn Met Leu Ser Ser Leu Gly Cys Leu Leu
1               5                   10                  15

Leu Cys Gly Ser Ile Thr Leu Ala Leu Gly Asn Ala Gln Lys Leu Pro
            20                  25                  30

Lys Gly Lys Arg Pro Asn Leu Lys Val His Ile Asn Thr Thr Ser Asp
        35                  40                  45

Ser Ile Leu Leu Lys Phe Leu Arg Pro Ser Pro Asn Val Lys Leu Glu
    50                  55                  60

Gly Leu Leu Leu Gly Tyr Gly Ser Asn Val Ser Pro Asn Gln Tyr Phe
65                  70                  75                  80

Pro Leu Pro Ala Glu Gly Lys Phe Thr Glu Ala Ile Val Asp Ala Glu
                85                  90                  95

Pro Lys Tyr Leu Ile Val Val Arg Pro Ala Pro Pro Pro Ser Gln Lys
            100                 105                 110

Lys Ser Cys Ser Gly Lys Thr Arg Ser Arg Lys Pro Leu Gln Leu Val
        115                 120                 125

Val Gly Thr Leu Thr Pro Ser Ser Val Phe Leu Ser Trp Gly Phe Leu
    130                 135                 140

Ile Asn Pro His His Asp Trp Thr Leu Pro Ser His Cys Pro Asn Asp
145                 150                 155                 160

Arg Phe Tyr Thr Ile Arg Tyr Arg Glu Lys Asp Lys Glu Lys Lys Trp
                165                 170                 175

Ile Phe Gln Ile Cys Pro Ala Thr Glu Thr Ile Val Glu Asn Leu Lys
            180                 185                 190

Pro Asn Thr Val Tyr Glu Phe Gly Val Lys Asp Asn Val Glu Gly Gly
        195                 200                 205

Ile Trp Ser Lys Ile Phe Asn His Lys Thr Val Val Gly Ser Lys Lys
    210                 215                 220

Val Asn Gly Lys Ile Gln Ser Thr Tyr Asp Gln Asp His Thr Val Pro
225                 230                 235                 240

Ala Tyr Val Pro Arg Lys Leu Ile Pro Ile Thr Ile Ile Lys Gln Val
                245                 250                 255

Ile Gln Asn Val Thr His Lys Asp Ser Ala Lys Ser Pro Glu Lys Ala
            260                 265                 270

Pro Leu Gly Gly Val Ile Leu Val His Leu Ile Ile Pro Gly Leu Asn
        275                 280                 285

Glu Thr Thr Val Lys Leu Pro Ala Ser Leu Met Phe Glu Ile Ser Asp
    290                 295                 300

Ala Leu Lys Thr Gln Leu Ala Lys Asn Glu Thr Leu Ala Leu Pro Ala
305                 310                 315                 320

Glu Ser Lys Thr Pro Glu Val Glu Lys Ile Ser Ala Arg Pro Thr Thr
                325                 330                 335

Val Thr Pro Glu Thr Val Pro Arg Ser Thr Lys Pro Thr Thr Ser Ser
            340                 345                 350

Ala Leu Asp Val Ser Glu Thr Thr Leu Ala Ser Ser Glu Lys Pro Trp
```

-continued

```
        355                 360                 365

Ile Val Pro Thr Ala Lys Ile Ser Glu Asp Ser Lys Val Leu Gln Pro
    370                 375                 380

Gln Thr Ala Thr Tyr Asp Val Phe Ser Ser Pro Thr Thr Ser Asp Glu
385                 390                 395                 400

Pro Glu Ile Ser Asp Ser Tyr Thr Ala Thr Ser Asp Arg Ile Leu Asp
                405                 410                 415

Ser Ile Pro Pro Lys Thr Ser Arg Thr Leu Glu Gln Pro Arg Ala Thr
            420                 425                 430

Leu Ala Pro Ser Glu Thr Pro Phe Val Pro Gln Lys Leu Glu Ile Phe
        435                 440                 445

Thr Ser Pro Glu Met Gln Pro Thr Thr Pro Ala Pro Gln Gln Thr Thr
    450                 455                 460

Ser Ile Pro Ser Thr Pro Lys Arg Arg Pro Arg Pro Lys Pro Pro Arg
465                 470                 475                 480

Thr Lys Pro Glu Arg Thr Thr Ser Ala Gly Thr Ile Thr Pro Lys Ile
                485                 490                 495

Ser Lys Ser Pro Glu Pro Thr Trp Thr Thr Pro Ala Pro Gly Lys Thr
            500                 505                 510

Gln Phe Ile Ser Leu Lys Pro Lys Ile Pro Leu Ser Pro Glu Val Thr
        515                 520                 525

His Thr Lys Pro Ala Pro Lys Gln Thr Pro Arg Ala Pro Pro Lys Pro
    530                 535                 540

Lys Thr Ser Pro Arg Pro Arg Ile Pro Gln Thr Gln Pro Val Pro Lys
545                 550                 555                 560

Val Pro Gln Arg Val Thr Ala Lys Pro Lys Thr Ser Pro Ser Pro Glu
                565                 570                 575

Val Ser Tyr Thr Thr Pro Ala Pro Lys Asp Val Leu Leu Pro His Lys
            580                 585                 590

Pro Tyr Pro Glu Val Ser Gln Ser Glu Pro Ala Pro Leu Glu Thr Arg
        595                 600                 605

Gly Ile Pro Phe Ile Pro Met Ile Ser Pro Ser Pro Ser Gln Glu Glu
    610                 615                 620

Leu Gln Thr Thr Leu Glu Glu Thr Asp Gln Ser Thr Gln Glu Pro Phe
625                 630                 635                 640

Thr Thr Lys Ile Pro Arg Thr Thr Glu Leu Ala Lys Thr Thr Gln Ala
                645                 650                 655

Pro His Arg Phe Tyr Thr Thr Val Arg Pro Arg Thr Ser Asp Lys Pro
            660                 665                 670

His Ile Arg Pro Gly Val Lys Gln Ala Pro Arg Pro Ser Gly Ala Asp
        675                 680                 685

Arg Asn Val Ser Val Asp Ser Thr His Pro Thr Lys Lys Pro Gly Thr
    690                 695                 700

Arg Arg Pro Pro Leu Pro Pro Arg Pro Thr His Pro Arg Arg Lys Pro
705                 710                 715                 720

Leu Pro Pro Asn Asn Val Thr Gly Lys Pro Gly Ser Ala Gly Ile Ile
                725                 730                 735

Ser Ser Gly Pro Ile Thr Thr Pro Pro Leu Arg Ser Thr Pro Arg Pro
            740                 745                 750

Thr Gly Thr Pro Leu Glu Arg Ile Glu Thr Asp Ile Lys Gln Pro Thr
        755                 760                 765

Val Pro Ala Ser Gly Glu Glu Leu Glu Asn Ile Thr Asp Phe Ser Ser
    770                 775                 780
```

-continued

```
Ser Pro Thr Arg Glu Thr Asp Pro Leu Gly Lys Pro Arg Phe Lys Gly
785                 790                 795                 800

Pro His Val Arg Tyr Ile Gln Lys Pro Asp Asn Ser Pro Cys Ser Ile
                805                 810                 815

Thr Asp Ser Val Lys Arg Phe Pro Lys Glu Glu Ala Thr Glu Gly Asn
            820                 825                 830

Ala Thr Ser Pro Pro Gln Asn Pro Pro Thr Asn Leu Thr Val Val Thr
        835                 840                 845

Val Glu Gly Cys Pro Ser Phe Val Ile Leu Asp Trp Glu Lys Pro Leu
    850                 855                 860

Asn Asp Thr Val Thr Glu Tyr Glu Val Ile Ser Arg Glu Asn Gly Ser
865                 870                 875                 880

Phe Ser Gly Lys Asn Lys Ser Ile Gln Met Thr Asn Gln Thr Phe Ser
                885                 890                 895

Thr Val Glu Asn Leu Lys Pro Asn Thr Ser Tyr Glu Phe Gln Val Lys
            900                 905                 910

Pro Lys Asn Pro Leu Gly Glu Gly Pro Val Ser Asn Thr Val Ala Phe
        915                 920                 925

Ser Thr Glu Ser Ala Asp Pro Arg Val Ser Glu Pro Val Ser Ala Gly
    930                 935                 940

Arg Asp Ala Ile Trp Thr Glu Arg Pro Phe Asn Ser Asp Ser Tyr Ser
945                 950                 955                 960

Glu Cys Lys Gly Lys Gln Tyr Val Lys Arg Thr Trp Tyr Lys Lys Phe
                965                 970                 975

Val Gly Val Gln Leu Cys Asn Ser Leu Arg Tyr Lys Ile Tyr Leu Ser
            980                 985                 990

Asp Ser Leu Thr Gly Lys Phe Tyr  Asn Ile Gly Asp Gln  Arg Gly His
        995                 1000                1005

Gly Glu  Asp His Cys Gln Phe  Val Asp Ser Phe Leu  Asp Gly Arg
    1010                1015                1020

Thr Gly  Gln Gln Leu Thr Ser  Asp Gln Leu Pro Ile  Lys Glu Gly
    1025                1030                1035

Tyr Phe  Arg Ala Val Arg Gln  Glu Pro Val Gln Phe  Gly Glu Ile
    1040                1045                1050

Gly Gly  His Thr Gln Ile Asn  Tyr Val Gln Trp Tyr  Glu Cys Gly
    1055                1060                1065

Thr Thr  Ile Pro Gly Lys Trp
    1070                1075
```

<210> SEQ ID NO 24
<211> LENGTH: 859
<212> TYPE: DNA
<213> ORGANISM: Homo sapiens

<400> SEQUENCE: 24

```
ctccggtgag ttttgtggcg ggaagcttct gcgctggtgc ttagtaaccg actttcctcc      60

ggactcctgc acgacctgct cctacagccg gcgatccact cccggctgtt cccccggagg     120

gtccagaggc ctttcagaag gagaaggcag ctctgtttct ctgcagagga gtagggtcct     180

ttcagccatg aagcatgtgt tgaacctcta cctgttaggt gtggtactga ccctactctc     240

catcttcgtt agagtgatgg agtccctaga gggcttacta gagagcccat cgcctgggac     300

ctcctggacc accagaagcc aactagccaa cacagagccc accaagggcc ttccagacca     360

tccatccaga agcatgtgat aagacctcct tccatactgg ccatattttg gaacactgac     420
```

-continued

```
ctagacatgt ccagatggga gtcccattcc tagcagacaa gctgagcacc gttgtaacca    480

gagaactatt actaggcctt gaagaacctg tctaactgga tgctcattgc ctgggcaagg    540

cctgtttagg ccggttgcgg tggctcatgc ctgtaatcct agcactttgg gaggctgagg    600

tgggtggatc acctgaggtc aggagttcga gaccagcctc gccaacatgg cgaaacccca    660

tctctactaa aaatacaaaa gttagctggg tgtggtggca gaggcctgta atcccagctc    720

cttgggaggc tgaggcggga gaattgcttg aacccgggga cggaggttgc agtgagccga    780

gatcgcactg ctgtacccag cctgggccac agtgcaagac tccatctcaa aaaaaaaaaa    840

aaaaaaaaaa aaaaaaaaa                                                 859


<210> SEQ ID NO 25
<211> LENGTH: 63
<212> TYPE: PRT
<213> ORGANISM: Homo sapiens

<400> SEQUENCE: 25

Met Lys His Val Leu Asn Leu Tyr Leu Leu Gly Val Val Leu Thr Leu
1               5                   10                  15

Leu Ser Ile Phe Val Arg Val Met Glu Ser Leu Glu Gly Leu Leu Glu
            20                  25                  30

Ser Pro Ser Pro Gly Thr Ser Trp Thr Thr Arg Ser Gln Leu Ala Asn
        35                  40                  45

Thr Glu Pro Thr Lys Gly Leu Pro Asp His Pro Ser Arg Ser Met
    50                  55                  60
```